(12) United States Patent
Chen

(10) Patent No.: US 10,684,244 B2
(45) Date of Patent: Jun. 16, 2020

(54) MAKING OF ORGANIC NANOBIOMIMETIC MEMRISTOR AND MEMCAPACITORS AND ITS APPLICATIONS IN DUAL SENSING OF A BIOMARKER IN NEURODEGENERATIVE DISEASES THERETO

(71) Applicant: Ellen T Chen, Rockville, MD (US)

(72) Inventor: Ellen T Chen, Rockville, MD (US)

( * ) Notice: Subject to any disclaimer, the term of this patent is extended or adjusted under 35 U.S.C. 154(b) by 0 days.

(21) Appl. No.: 15/693,435

(22) Filed: Aug. 31, 2017

(65) Prior Publication Data

US 2018/0088069 A1 Mar. 29, 2018

Related U.S. Application Data

(63) Continuation-in-part of application No. 14/919,606, filed on Oct. 21, 2015, now Pat. No. 9,793,503.

(51) Int. Cl.
*G01N 27/27* (2006.01)
*H01L 51/05* (2006.01)
*H01L 51/00* (2006.01)
*G01N 33/487* (2006.01)

(52) U.S. Cl.
CPC ....... *G01N 27/27* (2013.01); *G01N 33/48721* (2013.01); *H01L 51/004* (2013.01); *H01L 51/005* (2013.01); *H01L 51/0043* (2013.01); *H01L 51/0093* (2013.01); *H01L 51/0591* (2013.01); *G01N 2333/4709* (2013.01); *G01N 2800/2821* (2013.01)

(58) Field of Classification Search
CPC ........... G01N 27/3278; G01N 15/1031; G01N 2610/00; G01N 2800/7028; G01N 2015/1006; G01N 27/327; G01N 27/3276; G01N 33/48707; G01N 33/48735; G01N 2800/28–2828; G01N 27/04–041; G01N 27/045; G01N 27/22; G01N 27/227–228; B82Y 30/00; A61B 5/0091; A61B 5/40–4094; A61B 5/1468; H01L 51/0093; H01L 51/005; H01L 51/004; H01L 51/0043; H01L 51/0591
See application file for complete search history.

(56) References Cited

U.S. PATENT DOCUMENTS

| | | | |
|---|---|---|---|
| 7,462,659 B2* | 12/2008 | Rhee | C08B 37/0012 524/48 |
| 8,083,926 B2* | 12/2011 | Chen | C12Q 1/006 204/403.01 |
| 8,510,239 B2* | 8/2013 | Modha | G06N 3/063 706/14 |
| 2004/0072158 A1* | 4/2004 | Henkens | C12Q 1/6825 435/6.11 |

* cited by examiner

*Primary Examiner* — Amar Movva

(57) ABSTRACT

An organic memristor/memcapacitor device comprises a biomimetic membrane attached on the surface of an electrode forming variable size toroidal matrix cross-linked to derivative cyclodextrin polymers forming cross bars, that facilitate a dual functioning biosensor characteristics which enabled to detecting voltage and current changes of a biomarker β-amyloid (Aβ) in pM concentration that direct linked to Alzheimer's disease and other neurodegenerative diseases under reagent-less, tracer-free and antibody-free conditions in biological fluid specimens.

22 Claims, 57 Drawing Sheets

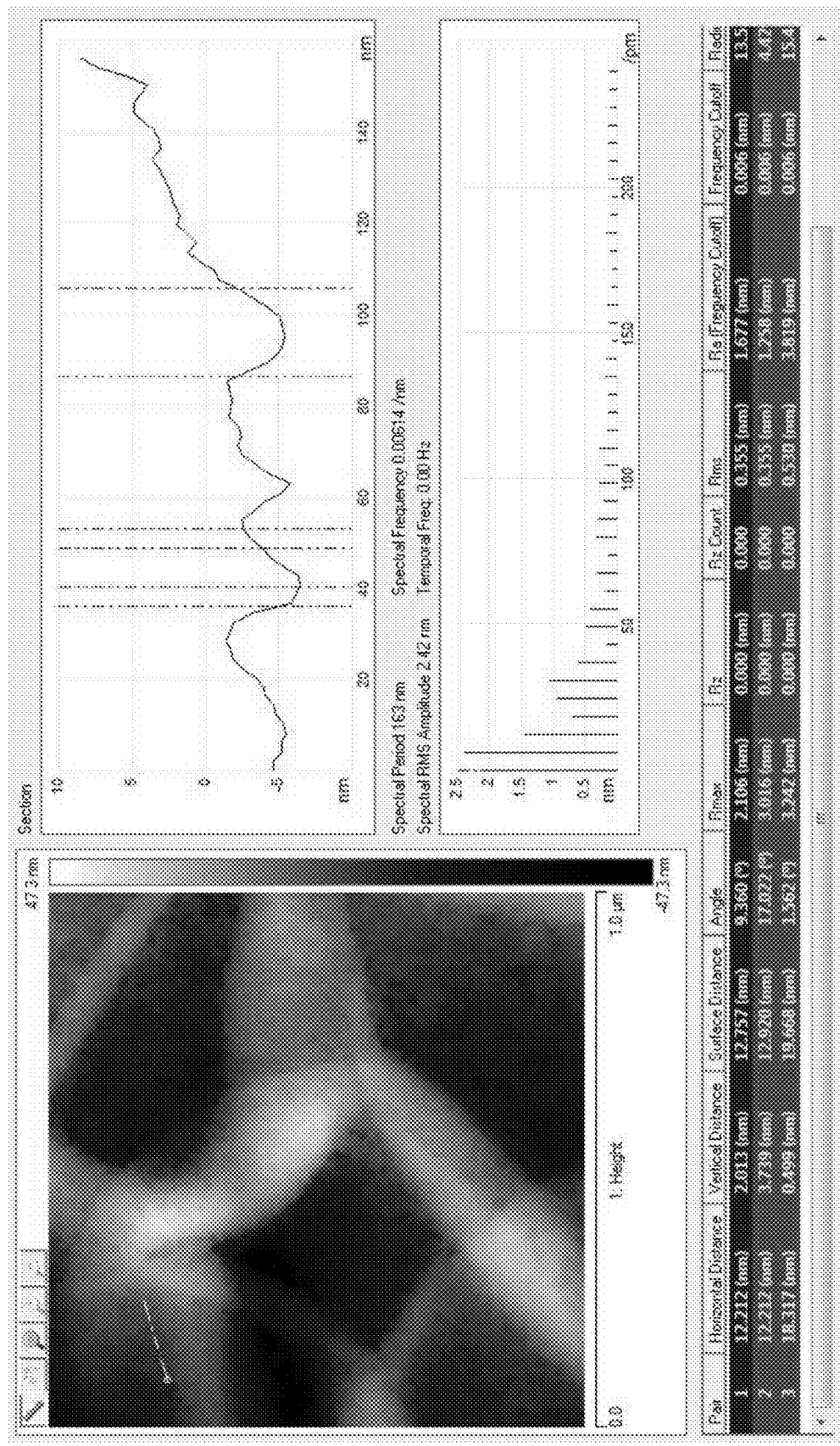
Fig 1A, Cross Section Analysis

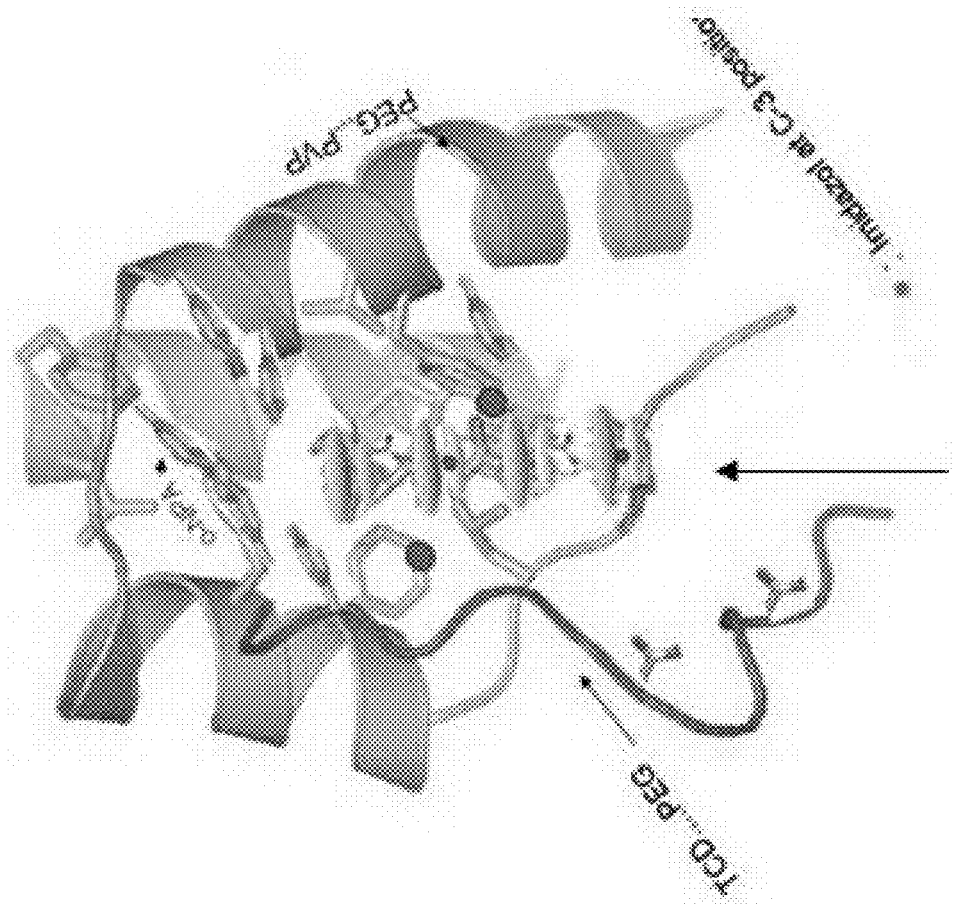

Biomimetic ACHE gorge with a damaged linen

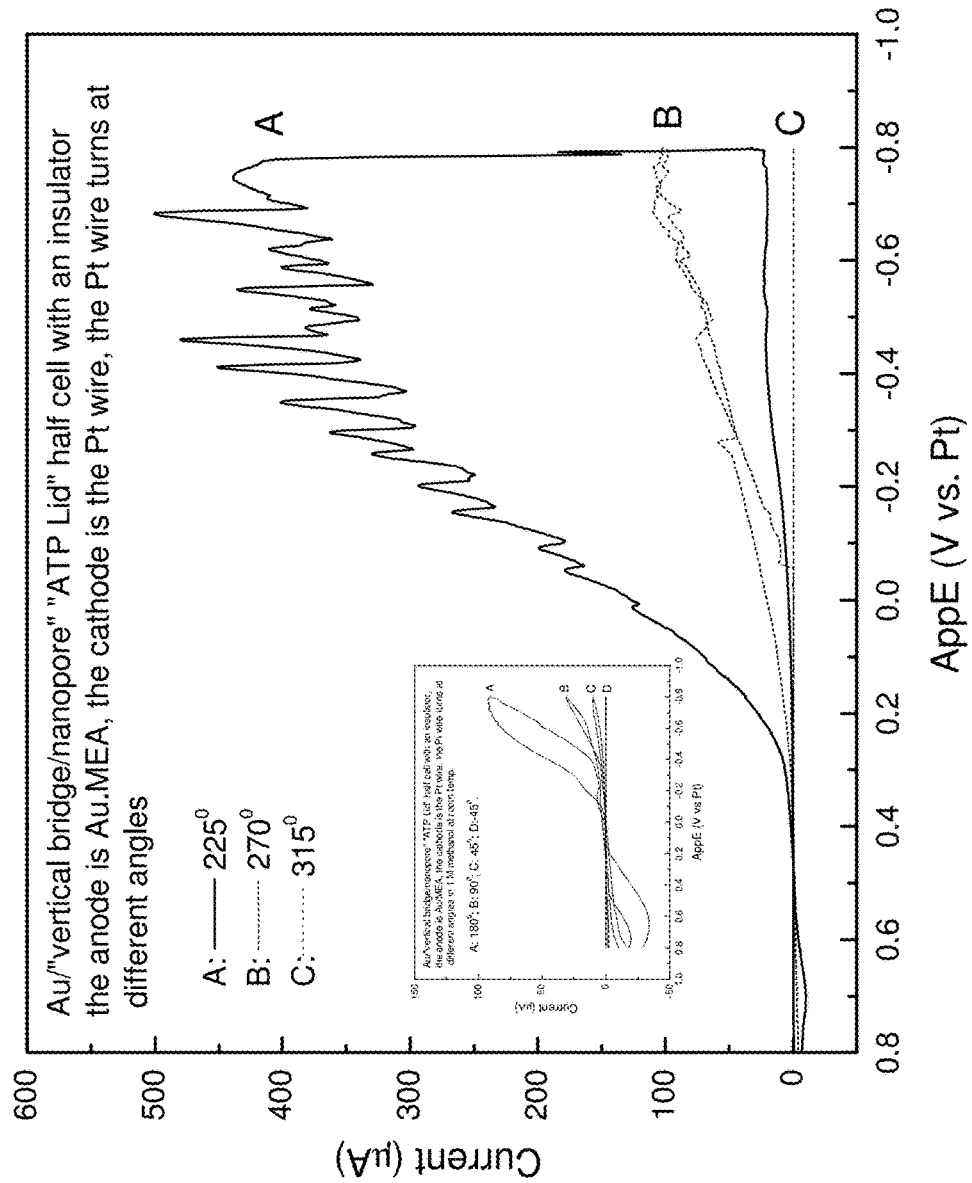

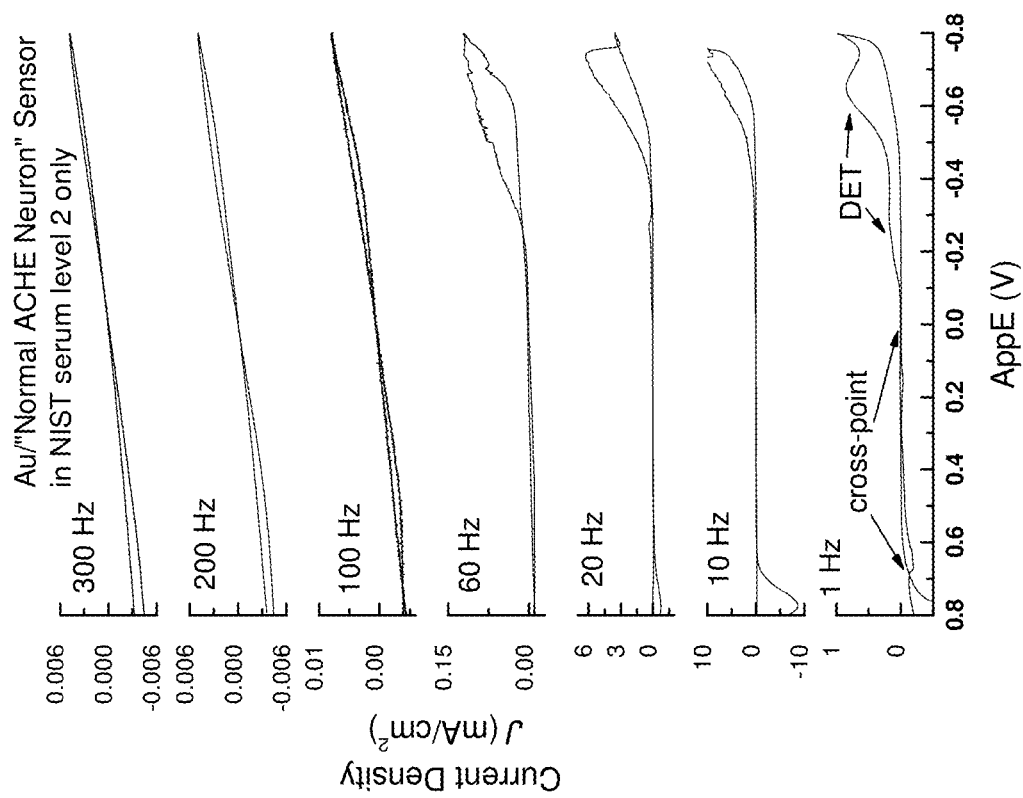

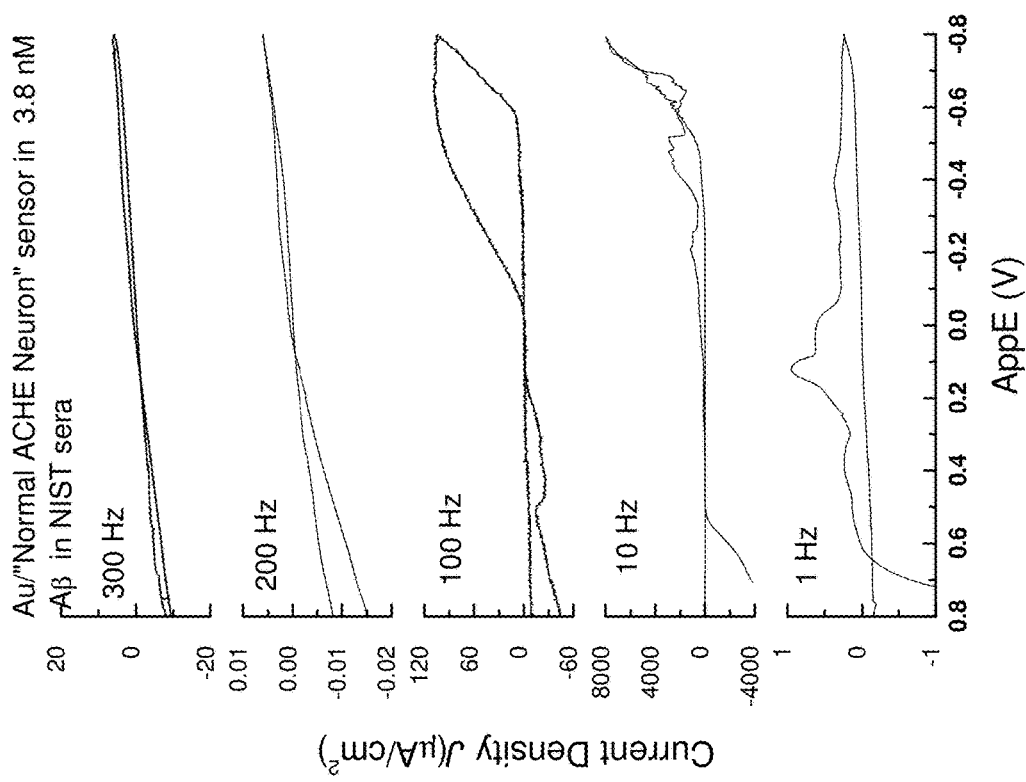

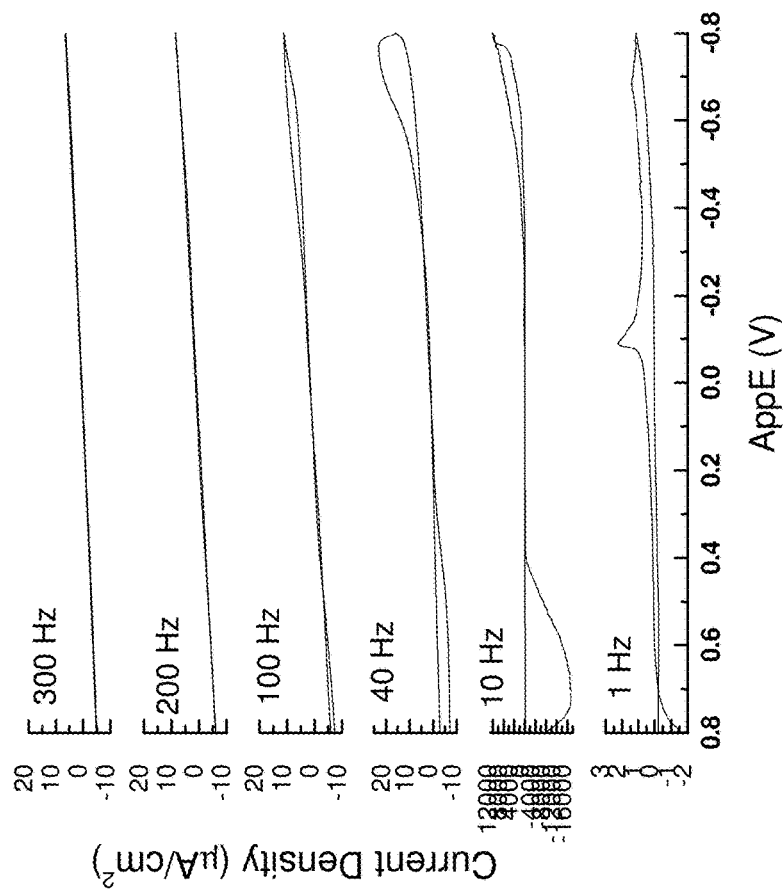

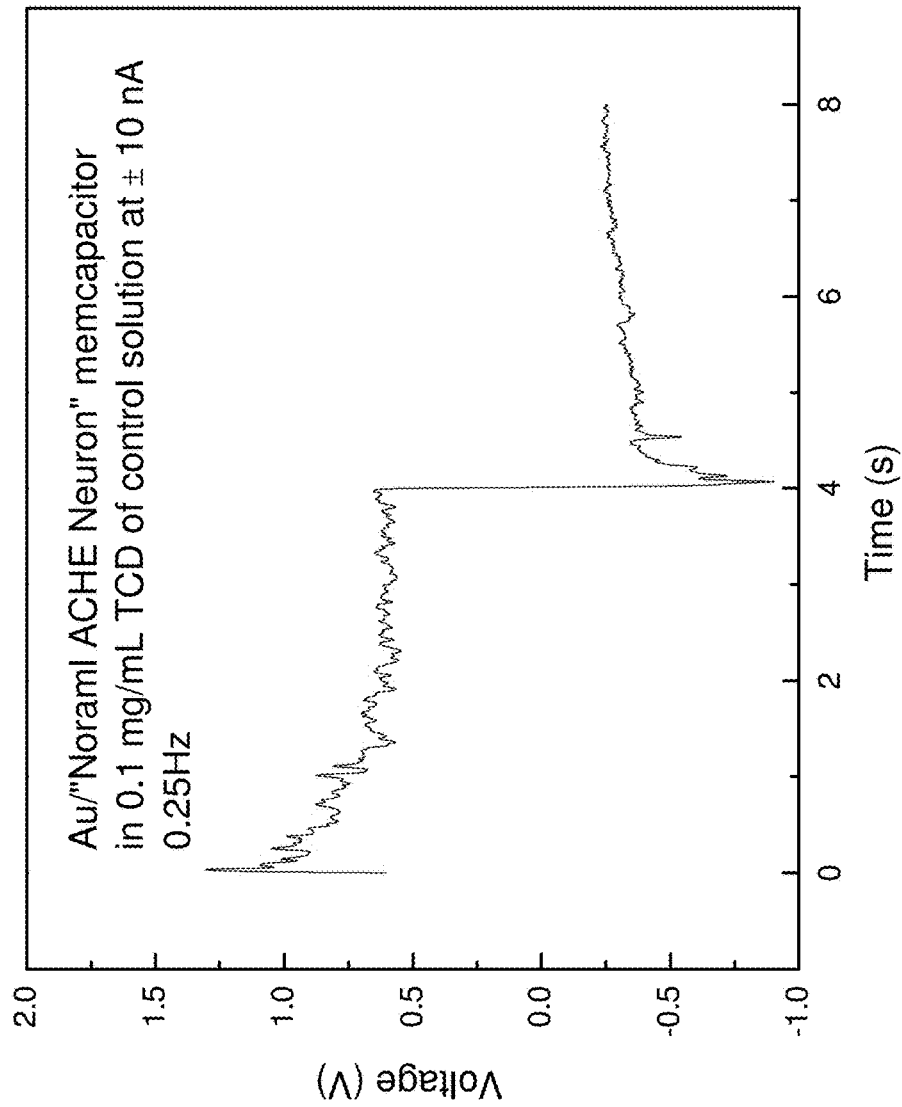
Fig. 32A₁

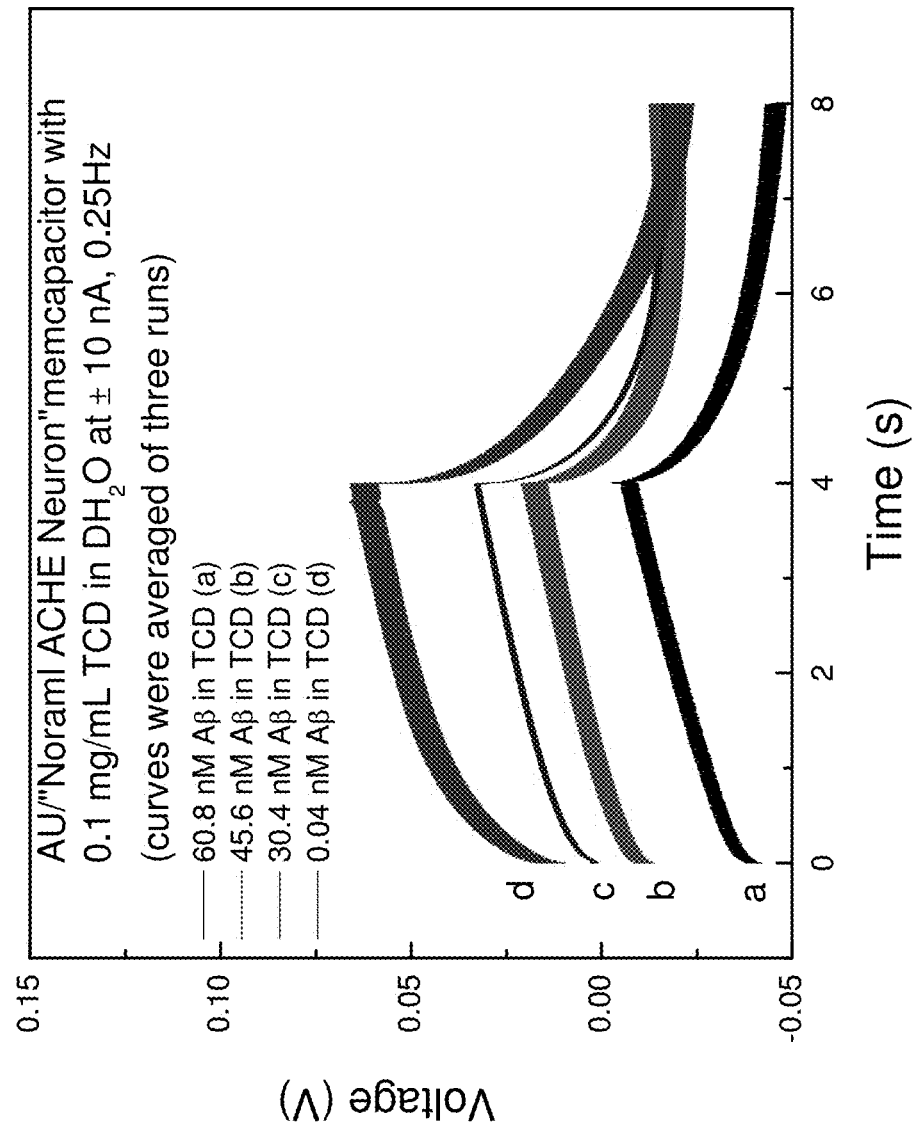
Fig. 32A₂

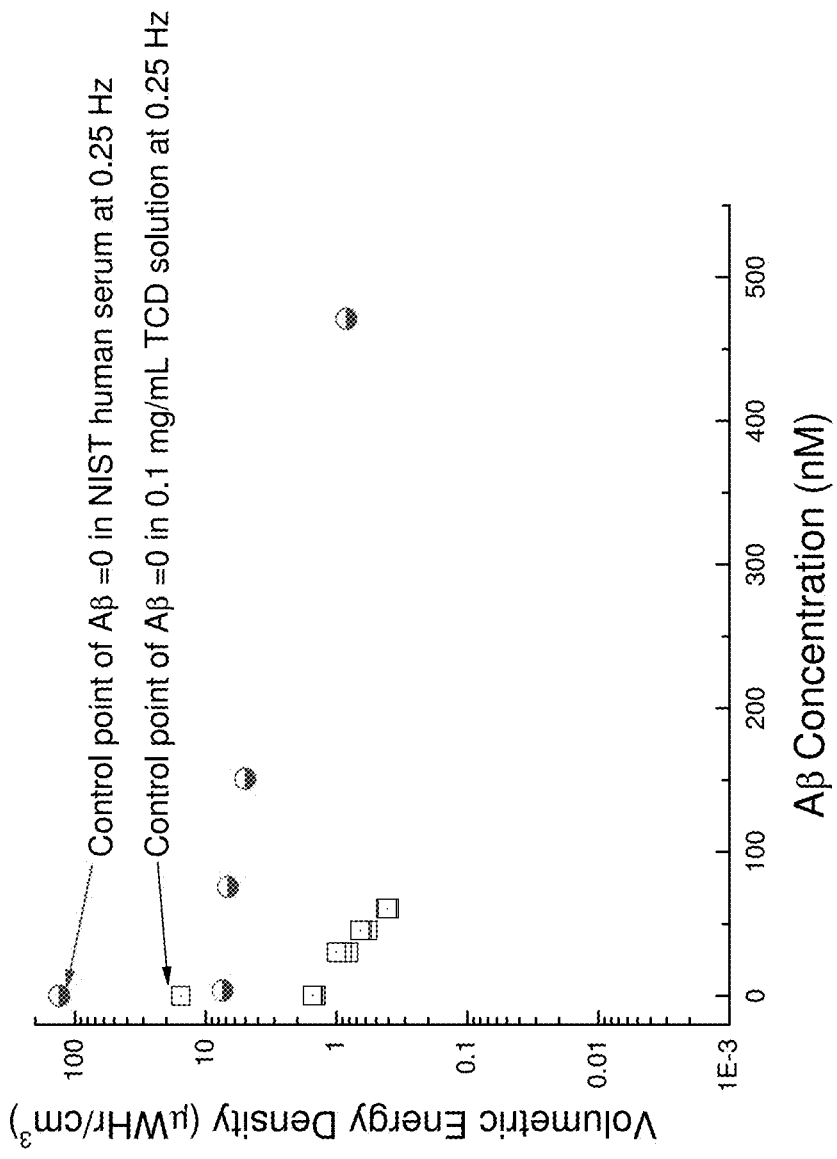
Fig. 32B₁

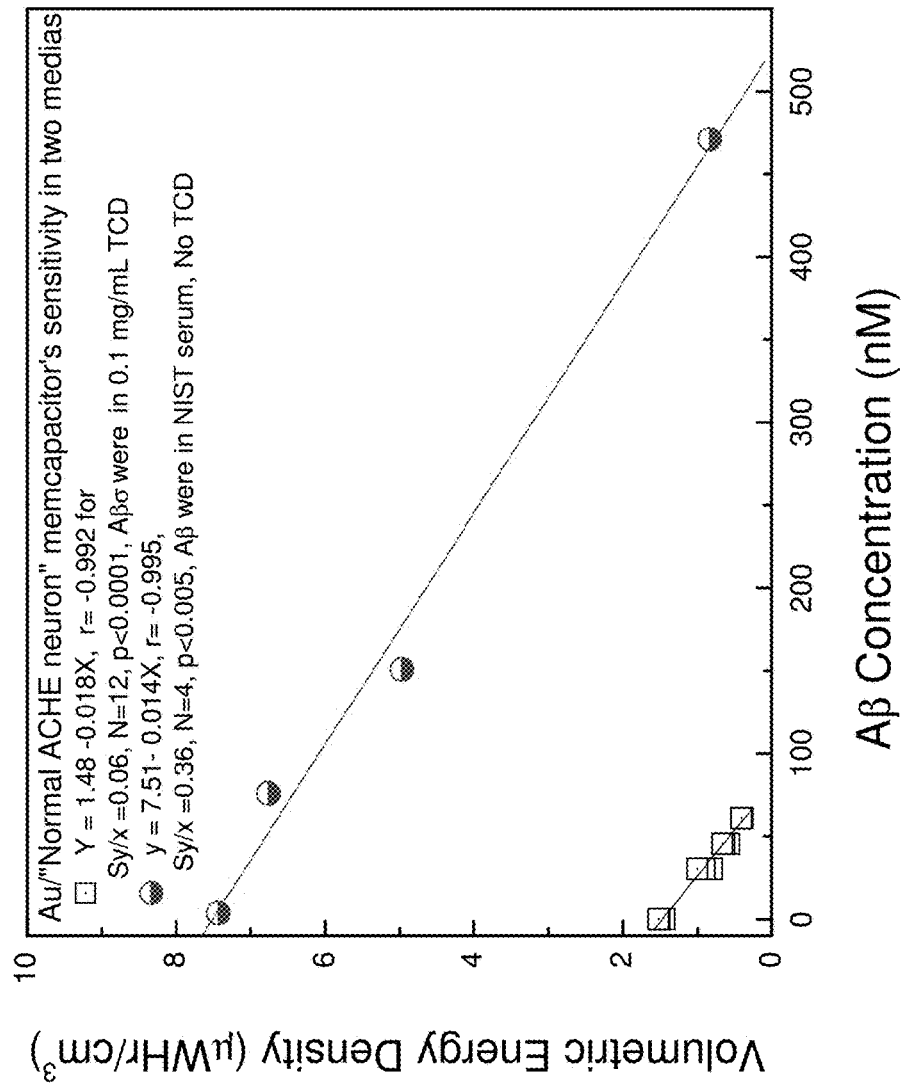
Fig. 32B₂

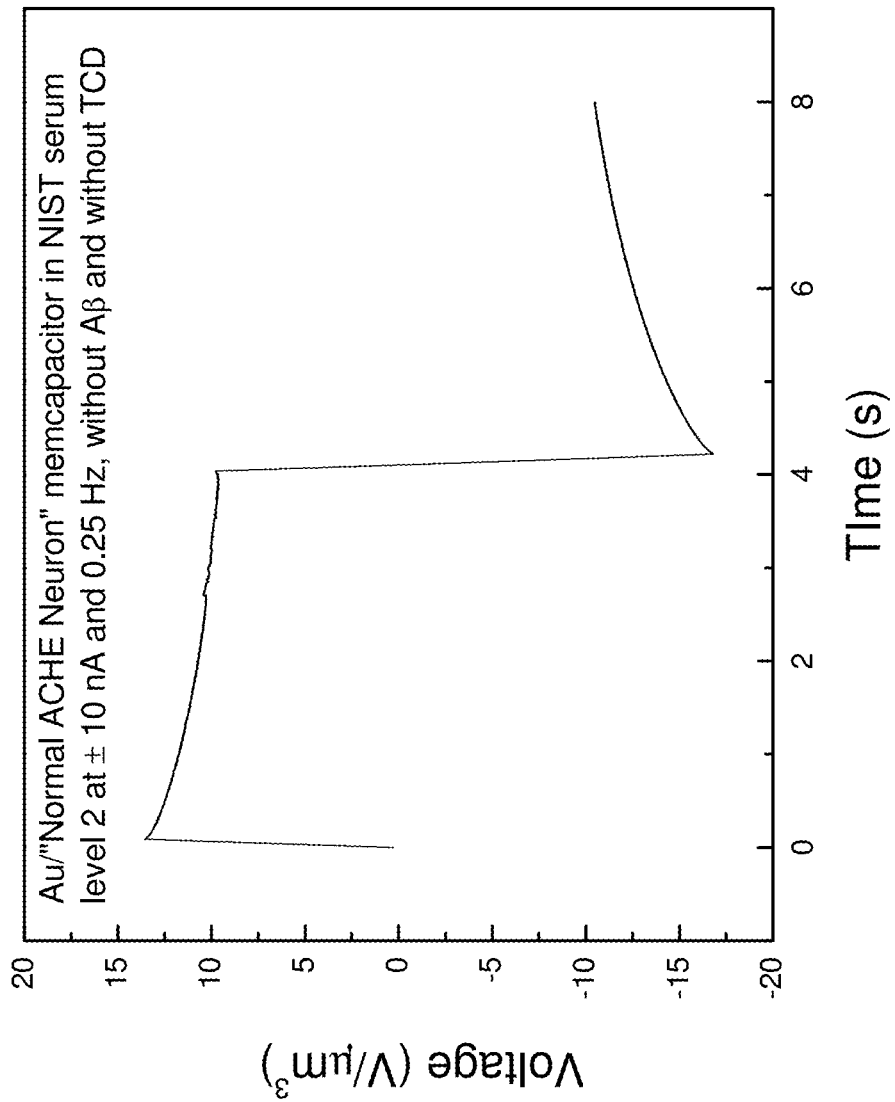

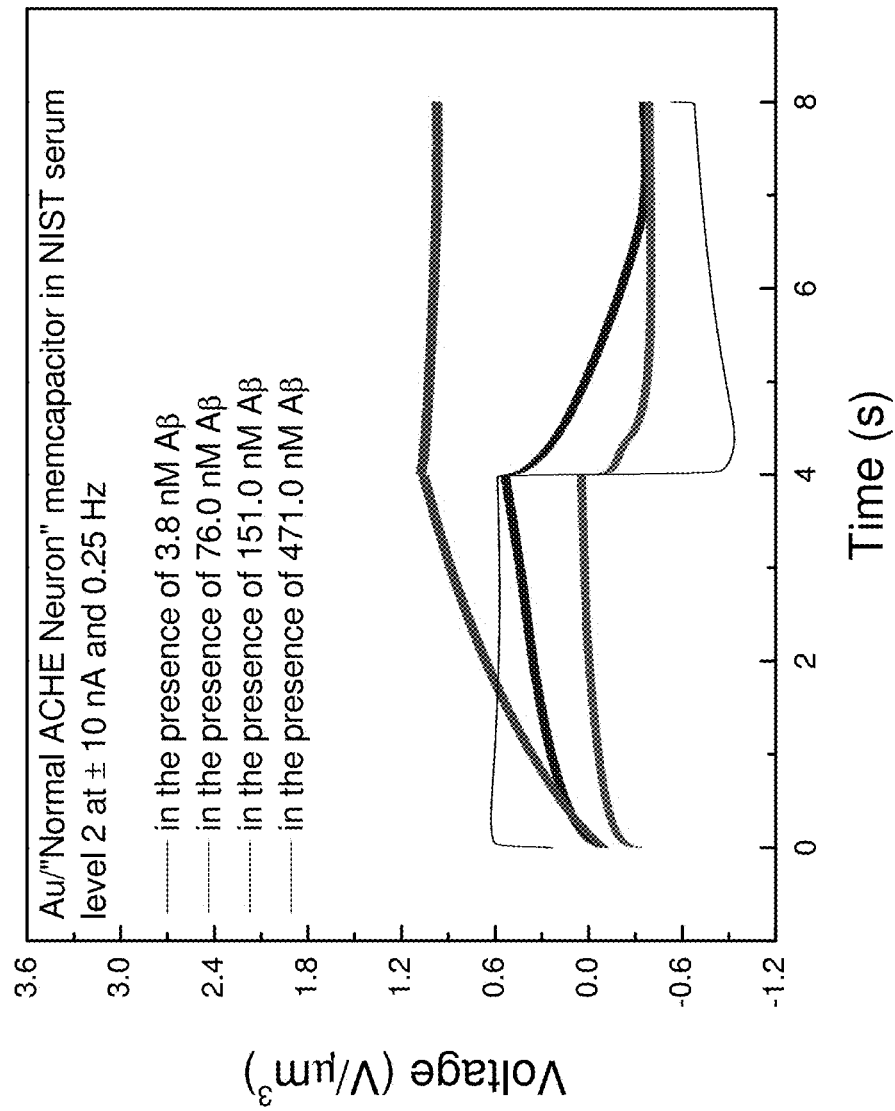
Fig. 32C₂

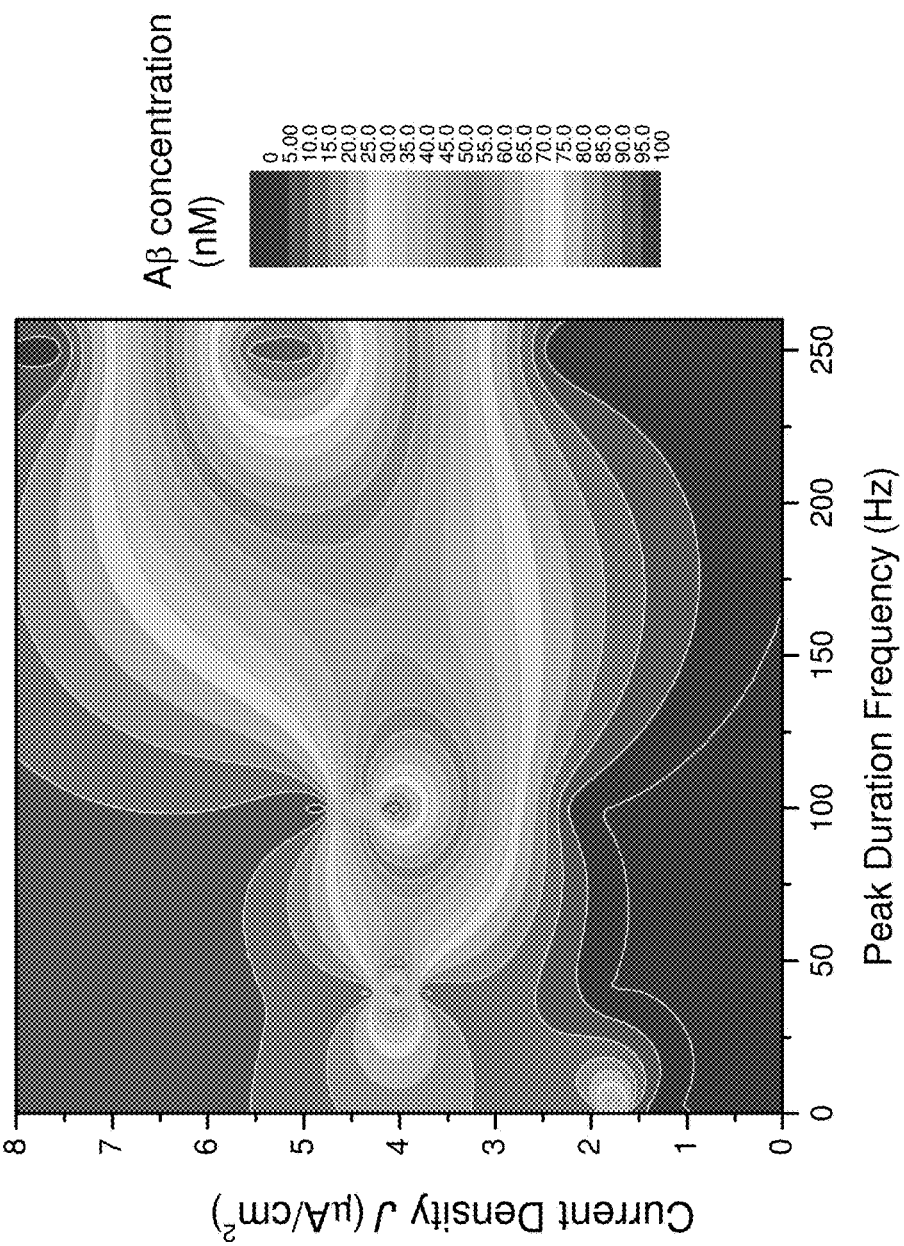

MAKING OF ORGANIC NANOBIOMIMETIC MEMRISTOR AND MEMCAPACITORS AND ITS APPLICATIONS IN DUAL SENSING OF A BIOMARKER IN NEURODEGENERATIVE DISEASES THERETO

CROSS-REFERENCE TO RELATED APPLICATIONS

This patent application claims the benefit of U.S. Provisional Patent Application Ser. No. 62/067,394 filed on Oct. 22, 2014 and Provisional Patent Application Ser. No. 62/067,212 filed on Oct. 22, 2014. The entire disclosures of the prior Patent Application Ser. No. 62/067,394 and 62/067,212 are hereby incorporated by reference, as is set forth herein in its entirety.

This patent application entitled "Making Of Organic Nanobiomimetic Memristors and Memcapacitors And Its Applications In Dual Sensing Of A Biomarker In Neurodegenerative Diseases Thereto" is a Continuation in Part of US patent application that claims the benefit of U.S. Non Provisional patent application Ser. No. 14/919,606 in titled of Nanostructured Organic Memristor/Memcapacitor Of Making With An Embedded Low-To-High Frequency Switch And A Method Of Inducing An Electromagnetic Field Thereto filed on Oct. 21, 2015 and also claim the benefit of the U.S. Non Provisional patent application Ser. No. 15/418,910 filed on Jan. 30, 2017. The entire disclosure of the prior patent application Ser. No. 15/418,910 and 14/919,606 is hereby incorporated by reference, as is set forth herein in its entirety.

FIELD OF THE INVENTION

The present invention related to the field of memristive/memcapacitive device in making to be feasible conducting "head-tail" biphase charge and discharge at wide range of frequencies by embedded the low-to-high frequency switch to effectively save energy and storage energy.

The present invention relates to the field of electrochemical sensors, in particular, to a device having both characteristics in memristor/memcapacitor acting as a dual function biosensor for detecting a biomarker that direct linked to Alzheimer's disease and other neurodegenerative diseases.

BACKGROUND OF THE INVENTION

Brachyhypopomus Electric (BHE) fish is known for its signal-cloaking behavior that allows it to avoid predators by shifting its electroreceptive pulses from low frequency to less detectable high-frequency through a phase-delay "head-tail" Electric Organ Discharge (EOD) with an energy saving consumption [1-3]. The BHE fish signal-cloaking strategy produces broad frequency electric field close to the body, causing its low frequency field to be cancelled by the local field, hence the predators are unable to find them. There is a risk of releasing huge amounts of heat during electrical discharge by the metal oxide thermal memcapacitors. This causes reduction in energy converting efficiency and is not beneficial for energy storage or for computing purposes. Special features of memcapacitors in negative and diverging capacitance received attention in the memristor/mamcapacitor society [16-17]. Martinez-Rincon's group published an article emphasizing the utility of negative and diverging capacitance in computing: "The resulting memcapacitor exhibits not only hysteretic charge-voltage and capacitance-voltage curves but also both negative and diverging capacitance within certain ranges of the field, due to its simplicity and unusual capacitance features. We expect it to find use in both analog and digital applications." [17]. Our group developed the first nanomemcapcitor with negative and diverging capacitance made of non metal oxide materials and reached a superior performance in plasticity, elasticity, stability and high power and energy density without environmental pollution and current leaking [6-7].

Circular current induced by junctions of aromatic molecules of the delocalized molecules has drawn interest from theoretical scientists [18-19]. Scientists have envisioned its future applications. The goal of this research is to develop a memcapacitor device that performs signal-cloaking, which mimics BHE's behavior saving operational energy and enhancing the energy storage under the conditions of electrolyte-free, nature ACHE-free, metal oxide-free and reagent-free.

Following are the Background of the Invention of CIP

Amyloid-beta (Aβ) peptide accumulation and neurofibrillary tangle identified as major pathological biomarkers linked to Alzheimer's disease (AD) has been studied over decades. Besides significant progresses have been made, but lack of effective treatments and preventions addressed an urgent need for early diagnose and detection of Alzheimer's disease. It is estimated the global prevalence of dementia is about 24 million, and will double to 2040, leading to a costly burden disease to the society [1-3].

It would be more attractive to have a less invasive method to use than the CSF fluid method and to have an inexpensive method to use compared to a costly positron emission tomography with radiotracers. Therefore, plasma or human serum would be more desirable as specimens. Several road blocks have been hampered to reach the goals: the instability of Aβ in biological fluid [4-6], protein non-specific bounding caused high imprecision [4,7] and the time consuming procedures of the assay. The human biomarkers for Alzheimer's research are predominantly quantified using enzyme-linked immunosorbent assays (ELISAs) that are associated imprecision of CV % values reported in literature about 20-30% [4,7]. Calls for development of innovative tools and therapeutic approaches for better measuring preclinical and clinical biomarkers and treatment for AD is needed urgently [8-10]. Based on our experiences in development of nanostructured biomimetic sensors used for detection of toxins, blood glucose, cancers and neurotransmitters, such as acetylcholine (ACH) in biological fluid with selectivity, sensitivity and accuracy under the conditions of tracers-free, antibody-free and reagent-less [11-16], overcoming the challenges to developing nanostructured dual devices for precisely measuring preclinical Aβ in clinical useful range is encouraging to us. Providing even more useful information to clinicians and to patients is always beneficial.

Our biomimetic acetylcholinesterase (ACHE) membrane with an ACHE active site gorge deposited on a gold chip could be a best candidate to sense the presence of excess monomer Aβ, because ACHE dysregulation is well known to link to cancer, AD and other diseases [17-18]. However, direct measure Aβ, not ACH, in blood is a challenge, even though we used this "normal ACHE gorge" sensor to quantitatively detect ACHE in fM in amperometric mode [15] against a "mutated ACHE gorge" sensor, which was unable to sense ACH. Furthermore, we found the normal ACHE gorge sensor is able to serve as a memcapacitor type of memory device that clearly distinguishes conformational and neuronal circuitry change due to brain cancer cells' "bio-communicating" to the sensor [16]. Therefore, we hope the dual sensor would be able to sense the presence of Aβ in pM in order to lay a foundation for further study of the role of Aβ.

SUMMARY OF THE INVENTION

It is an object of the present invention to provide a new generation of memristor/memcapacitor that embodiments with characteristics of both types of devices.

It is an object of the present invention to provide a new generation of memristor/memcapacitor that was not made by any metal oxide, but of biomimetic organic cross-linked polymer membrane that mimics a normal cylindrical confined acetylecholenesterase (ACHE) eternal gorge as a "normal brain" prosthesis model with a "biomimetic linen" attached in the gorge thereto.

It is an object of the present invention to provide a new generation of memristor/memcapacitor device with new method of making with an embedded Low-to-high frequency switch for saving energy and effectively storage energy.

It is an object of the present invention to provide a new generation of memristor/memcapacitor device that comprises of an biomimetic organic polymer membrane that mimics a mutated acetylecholenesterase (ACHE) eternal gorge with 14 hydrophobic residues groups knocked out, serves as a "damaged brain" prosthesis model.

It is an object of the present invention to provide a new generation of organic Memristor/Memcapacitor having no hydrophobic reagent o-nitrophenyl acetate applied to the half-cell MEA compared with the o-NPA embedded in the half-cell MEA in order to study whether or not the disturbing circular current formed inducing an electromagnetic field strong enough to affect the Low-to High frequency switch.

Following are the Summary of Invention for the CIP Application

It is an object of the present invention to provide a new generation of organic memristor/memcapacitor compromising the active sites of a biomimetic ACHE gorge in the membrane of the device.

It is an object of the present invention to provide a new generation of organic memristor/memcapacitor with a "biomimetic linen" attached inside of the biomimetic ACHE gorge thereto.

It is an object of the present invention to provide a new generation of organic memristor/memcapacitor with multiple-layers and cross-bars forming a biomimetic neuronal network matrix.

It is an object of the present invention to provide a new generation of organic memristor/memcapacitor that is capable for dual sensing functioning of a biomarker Aβ in Alzheimer's patients in current and voltage change without using antibody, mediator, labels and tracers.

It is a further object of the present invention to provide a new generation organic memristor/memcapacitor to be able to sense sub pM Aβ in biological fluid without instability and the improved sensitivity and accuracy is set forth over a wide useful clinical range.

BRIEF DESCRIPTION OF THE DRAWINGS

FIG. 1A shows three-dimensional atomic force microscopy (AFM) image of the nanostructured biomimetic "Mutated ACHE Gorge" with a vertical bridge and the cross section analysis results were shown in the table listed below.

FIG. 4A depicts the art illustration of the SAM molecular polymer architecture for memristor sensor 1 as the model for a "normal ACHE Gorge".

FIG. 14B depicts the AU/"vertical bridge/nanopore" "Predator" memcapacitor has a synchronized peak at 225°, and the insert is the angles change over 45-180° in 1M methanol at 20 mV/s scan rate.

Followings are the Brief Descriptions of the Drawings for CIP Application

Figure 23:
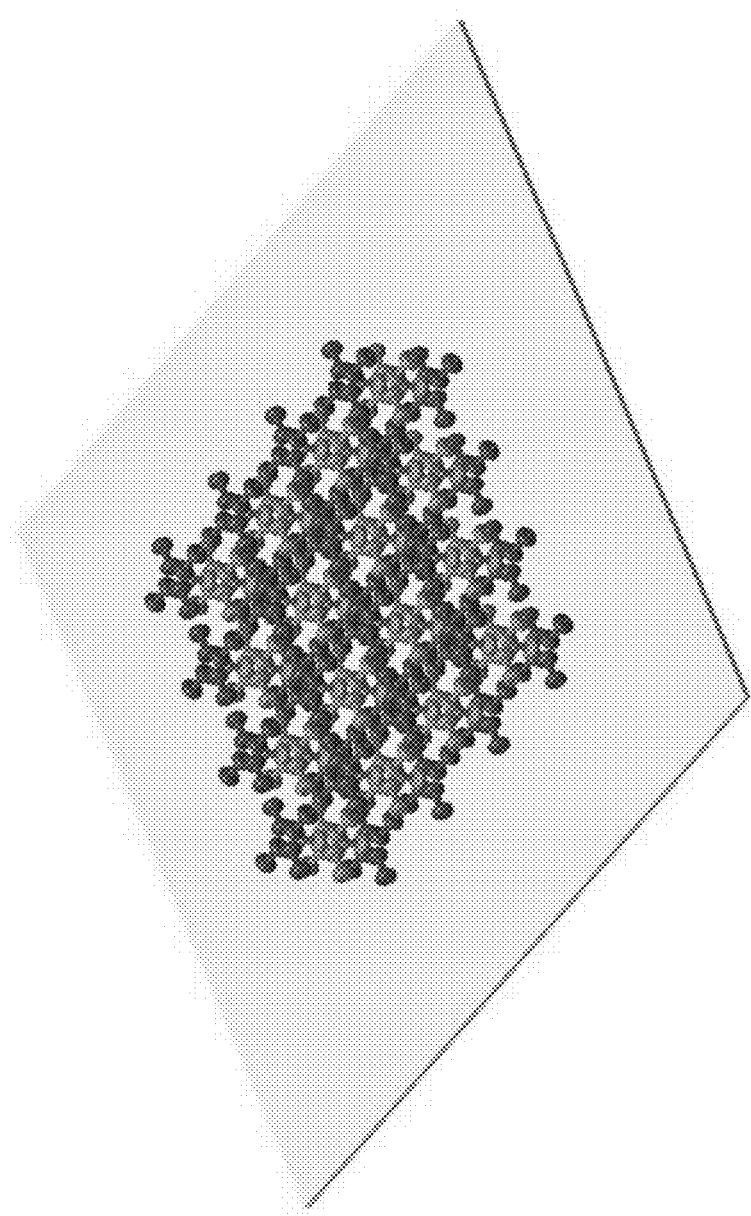

FIG. 23 illustrates the 3D memcapacitor blocks serve as the dual sensor. The light green color substrate is a 50 nm thickness pure gold plate attached onto a flexible plastic plate. The model consists of green balls and sticks in the top and bottom layer covered with conductive cross-linked polymers; The oranges represent the inner "ACHE Gorge" neuronal axons in narrow cylinders connected through the neuronal terminals and dendrites as truncated donuts in a compact flat metrics by forming toroidal matrix.

Figure 24A:
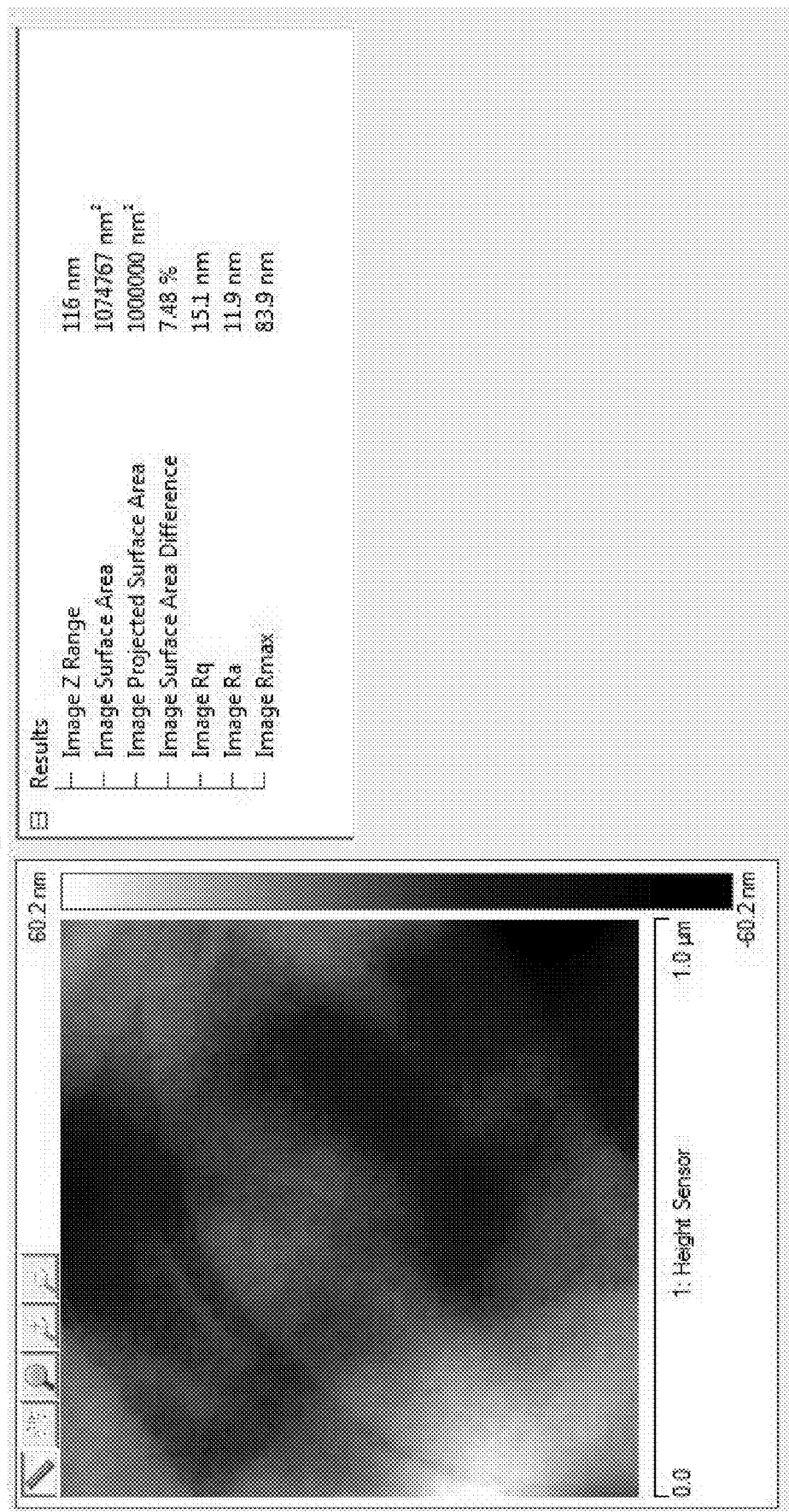
Figure 24B:
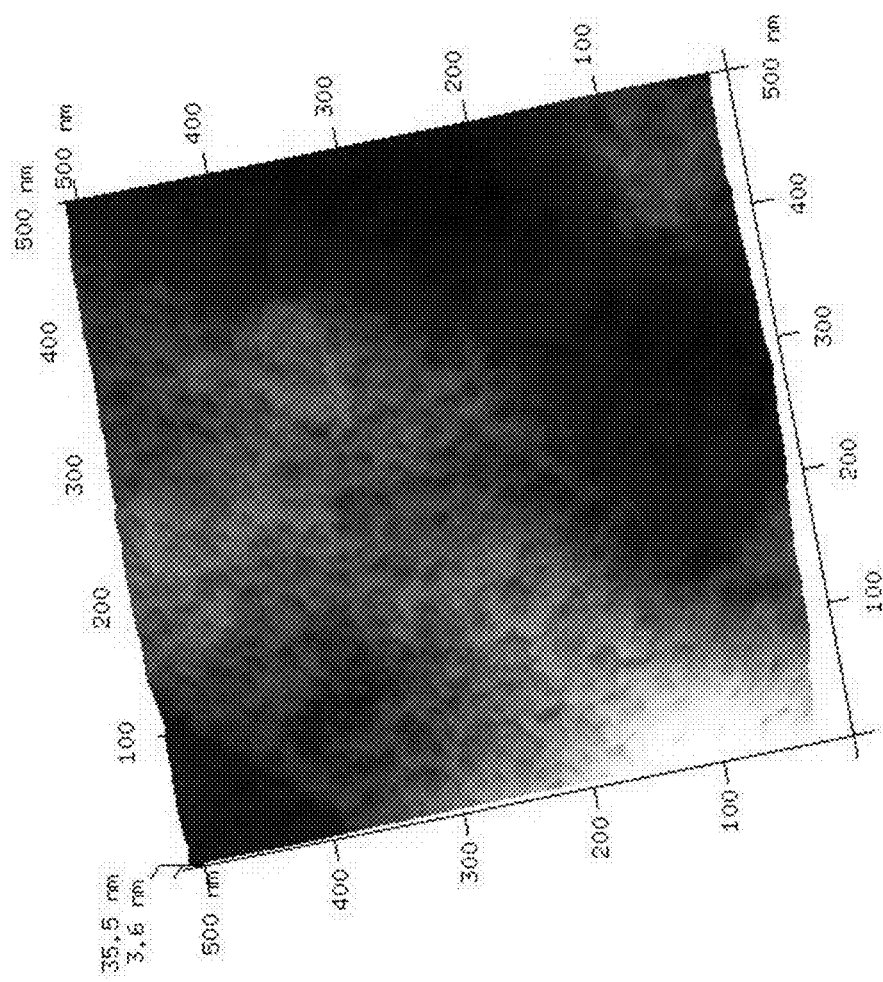

FIG. 24A shows the AFM image of the nanostructured flat horizontal bridge and large nanopores as "breathing-hole" nearby the bridge. FIG. 24B shows the enlarged AFM of the flat bridge/nanopore AFM structure.

Figure 25:
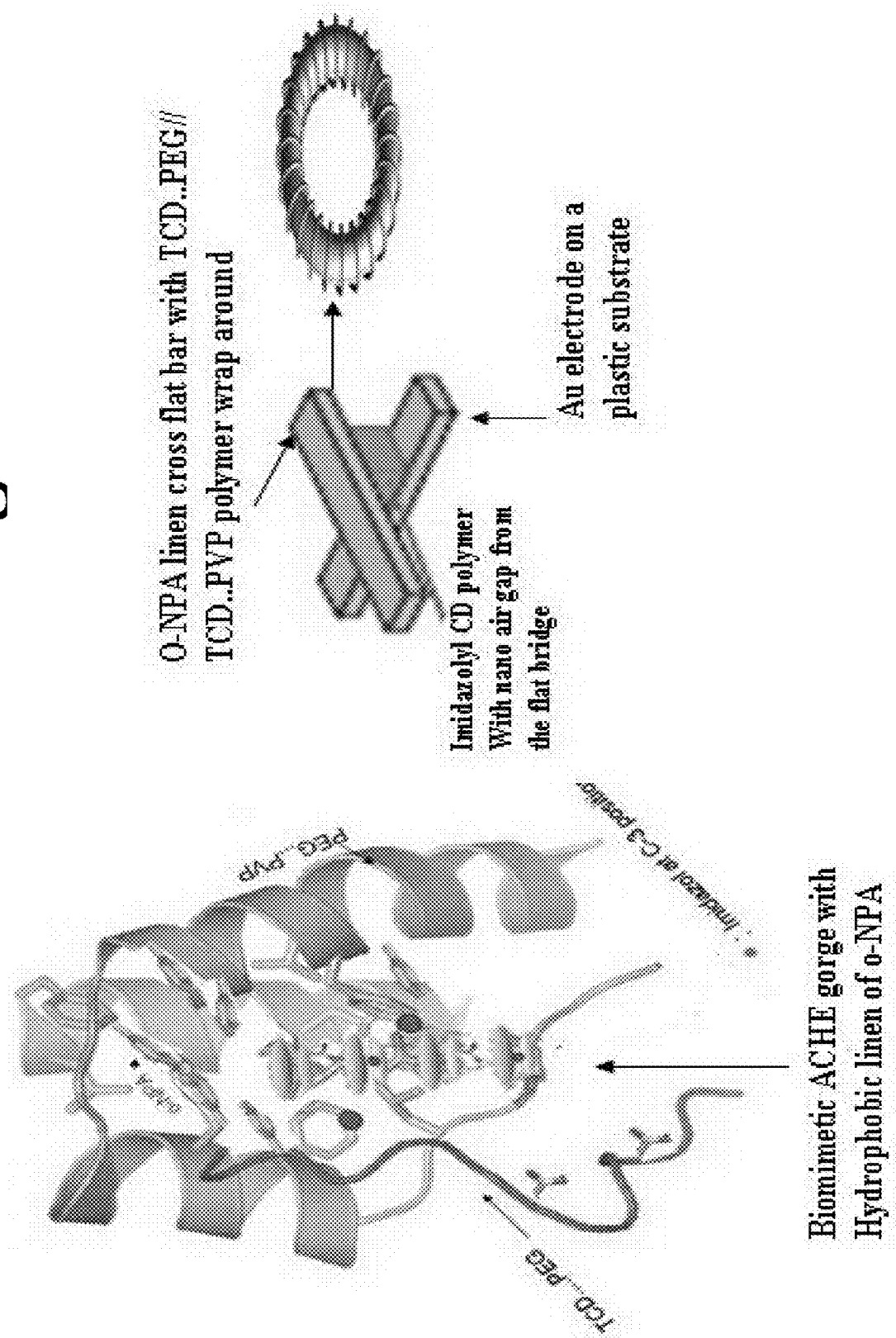

FIG. 25 depicts the art illustration of the SAM molecular polymer architecture for the Biomimetic normal ACHE gorge neuron in the left, and on the right hand side is an illustration of the cross bar layout and led to form the toroidal matrix.

Figure 26:
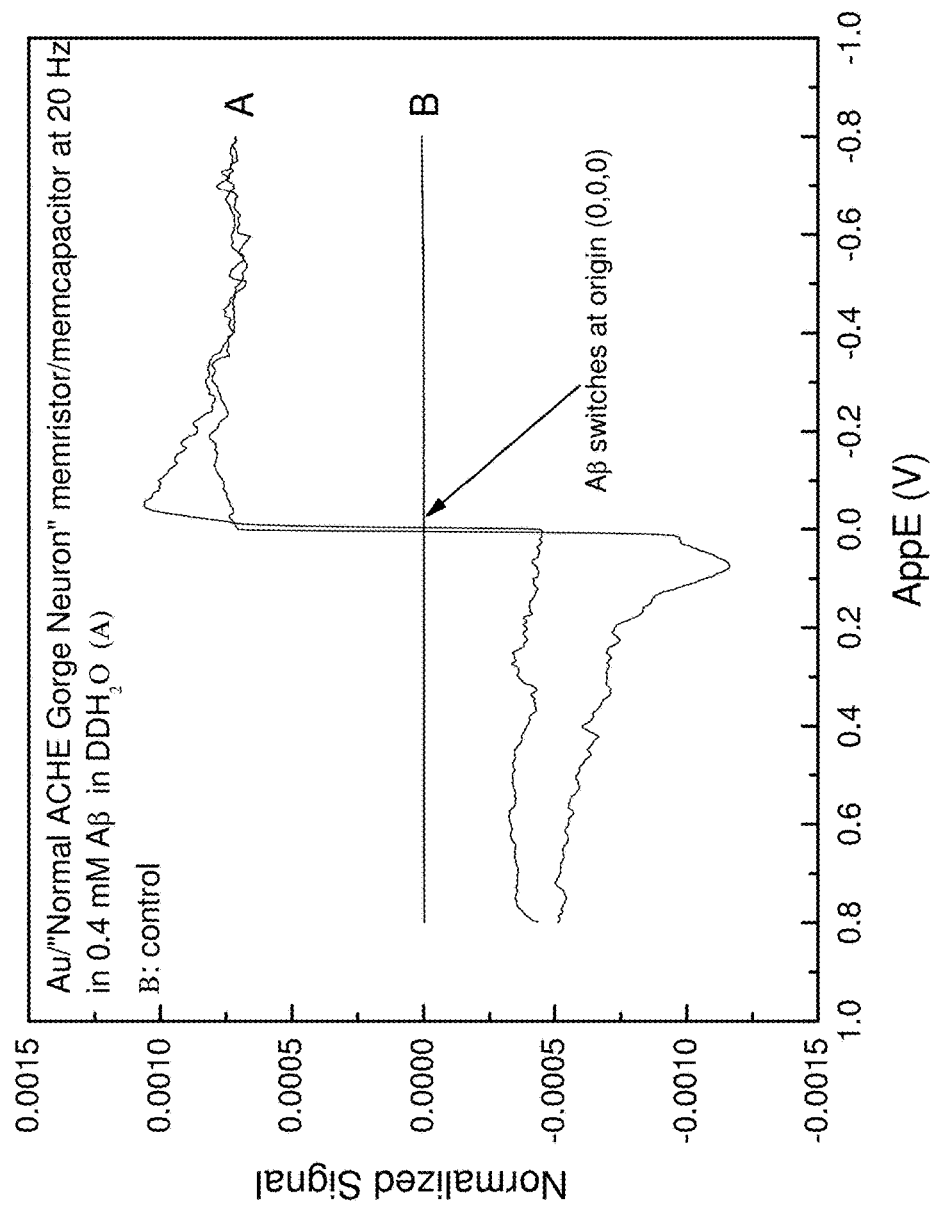

FIG. 26 illustrates the hysteresis of the i-V curve of "A" in 400 µM Aβ in DDH$_2$O with a switch point at origin (0, 0, 0) against the control curve "B".

FIG. 27A depicts frequency affects on CV curves from 1 to 300 Hz in NIST SRM965A human serum with certified blood glucose in level 2 (70 mg/dL) without Aβ.

FIG. 27B depicts frequency affects on CV curves from 1 to 300 Hz in NIST SRM965A human serum with certified blood glucose in level 2 (70 mg/dL) with 3.8 nM Aβ.

FIG. 27C depicts frequency affects on CV curves from 1 to 300 Hz in NIST SRM965A human serum with certified blood glucose in level 2 (70 mg/dL) with 76 nM Aβ.

Figure 28:
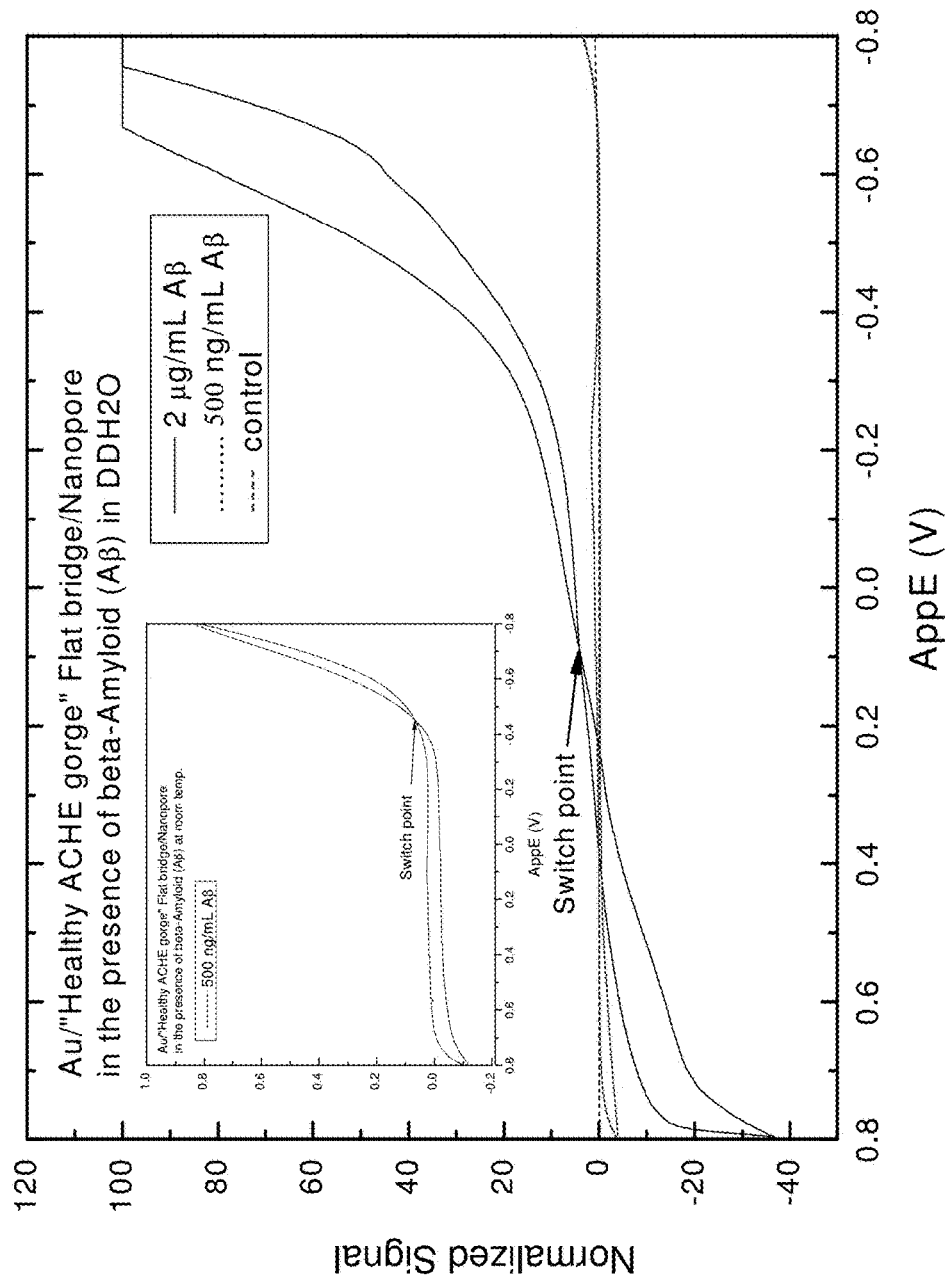

FIG. 28 illustrates the CV profiles without TCD. The control is in red; the insert is 380 nM Aβ; the solid black curve is with 1.52 µM Aβ.

Figure 29:
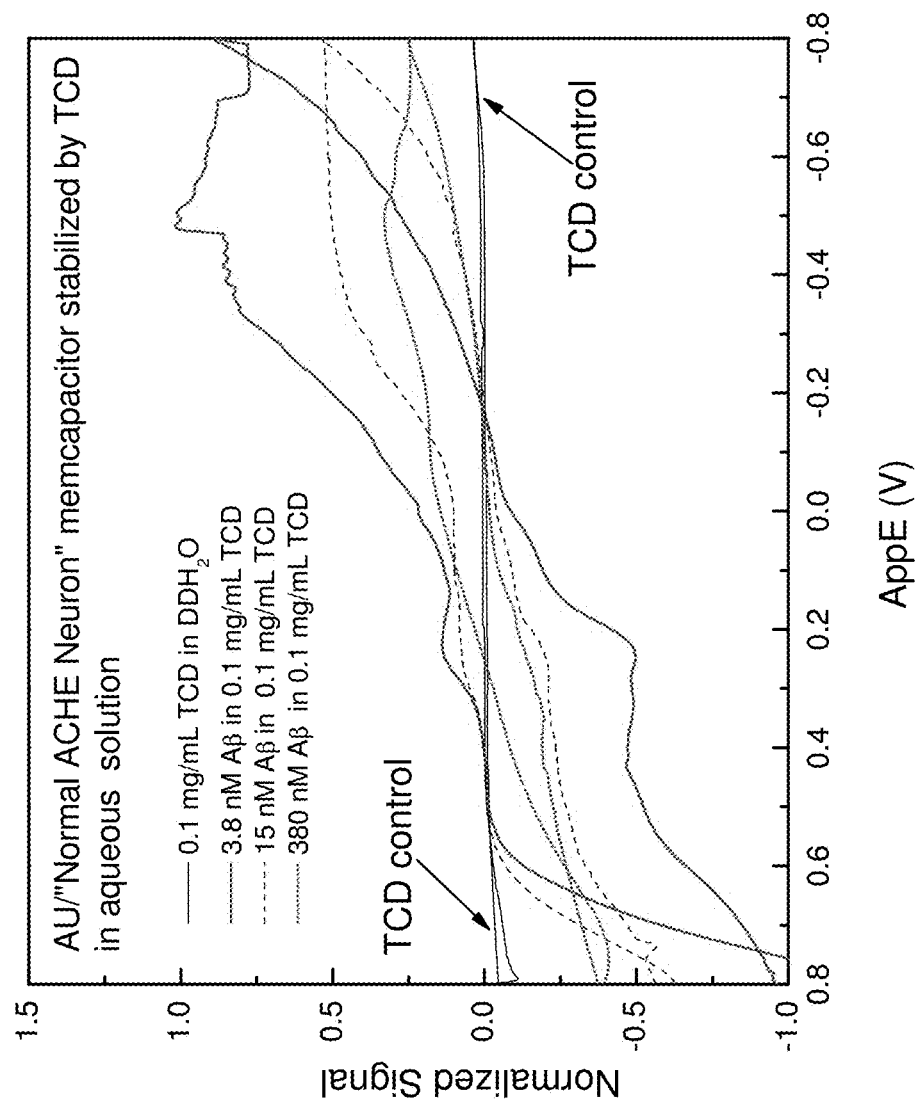

FIG. 29 depicts the i-V behaviors of the sensor in the 0.1 mg/mL stabilizer TCD in DDH$_2$O with Aβ at 0, 3.8, 15, 380 nM, respectively.

Figure 30:
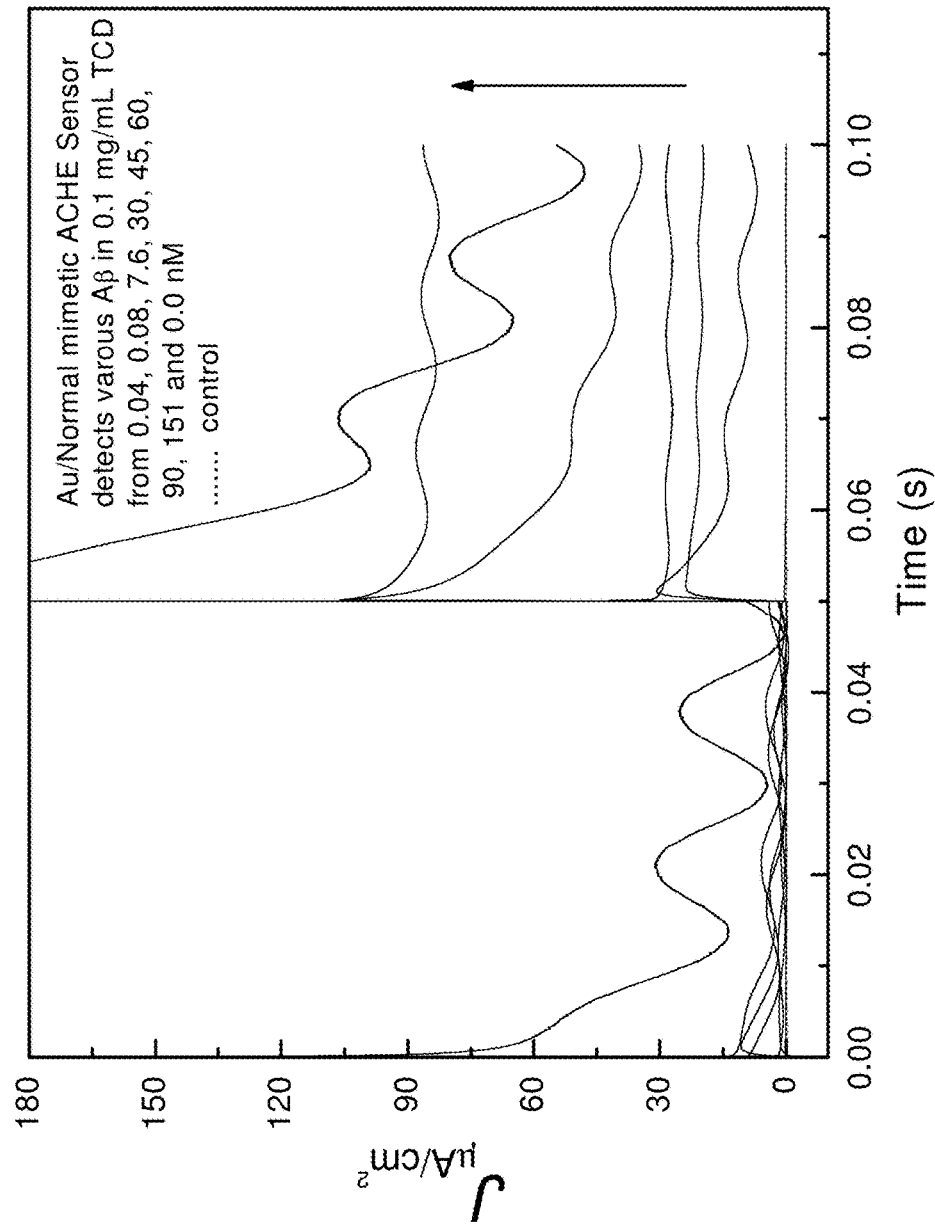

FIG. 30 illustrates CA curve profiles of Aβ affecting of the current intensity over concentration levels from 0.0 to 151 nM at 9 levels in the presence of 0.1 mg/mL TCD stabilizer in DDH$_2$O.

Figure 31:
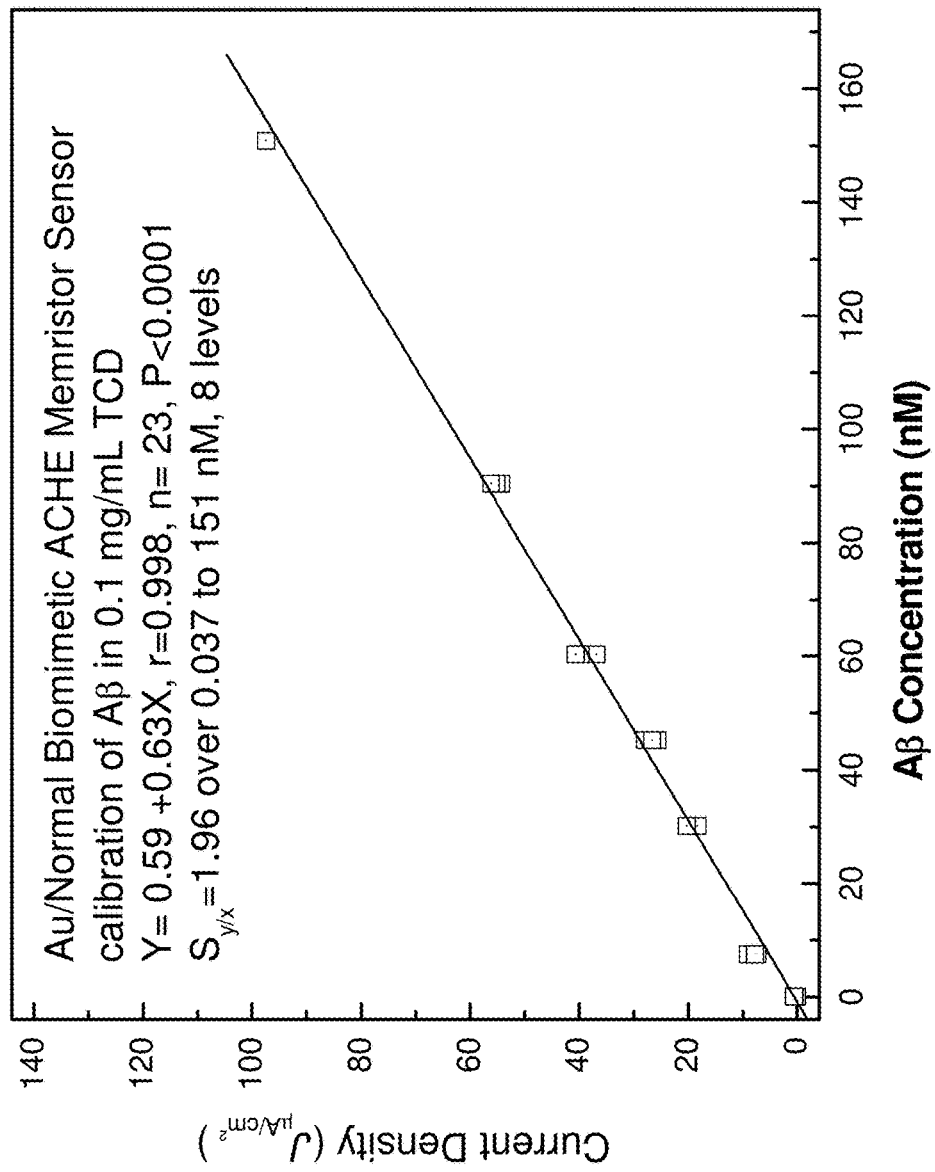

FIG. 31 depicts the calibration plot of current density vs. Aβ concentrations using the CA method.

FIG. 32A$_1$ depicts synapse voltage profile vs. time as shown for without Aβ in aqueous solution. FIG. 32A$_2$ depicts voltage profiles with Aβ in aqueous solution in the presence of 0.1 mg/mL stabilizer TCD with Aβ concentrations change from zero to 0.04 nM, 30.4 nM, 45.6 nM, 60.8 nM at ±10 nA and 0.25 Hz, respectively, and each sample run triplicates at room temperature. FIG. 32B$_1$ illustrates the experimental data points of volumetric energy density vs. Aβ concentration from zero to 471 nM in NIST serum (Red) without a stabilizer TCD, and in water with 0.1 mg/mL stabilizer TCD (black). FIG. 32B$_2$ depicts the calibration curves of volumetric energy density vs. Aβ concentration over 3.8 nM to 471 nM for using NIST serum media and over 0.04 nM to 60.8 nM for using water as media, respectively. FIG. 32C$_1$ depicts synapse voltage profile using DSCPO method in NIST SRM965A serum samples for without spiking Aβ at ±10 nA at 0.25 Hz. FIG. 32C$_2$ depicts synapse voltage profiles using DSCPO method in NIST SRM965A serum samples for with Aβ concentrations from 3.8, 76, 151, to 471 nM, respectively at ±10 nA at 0.25 Hz.

Figure 33:
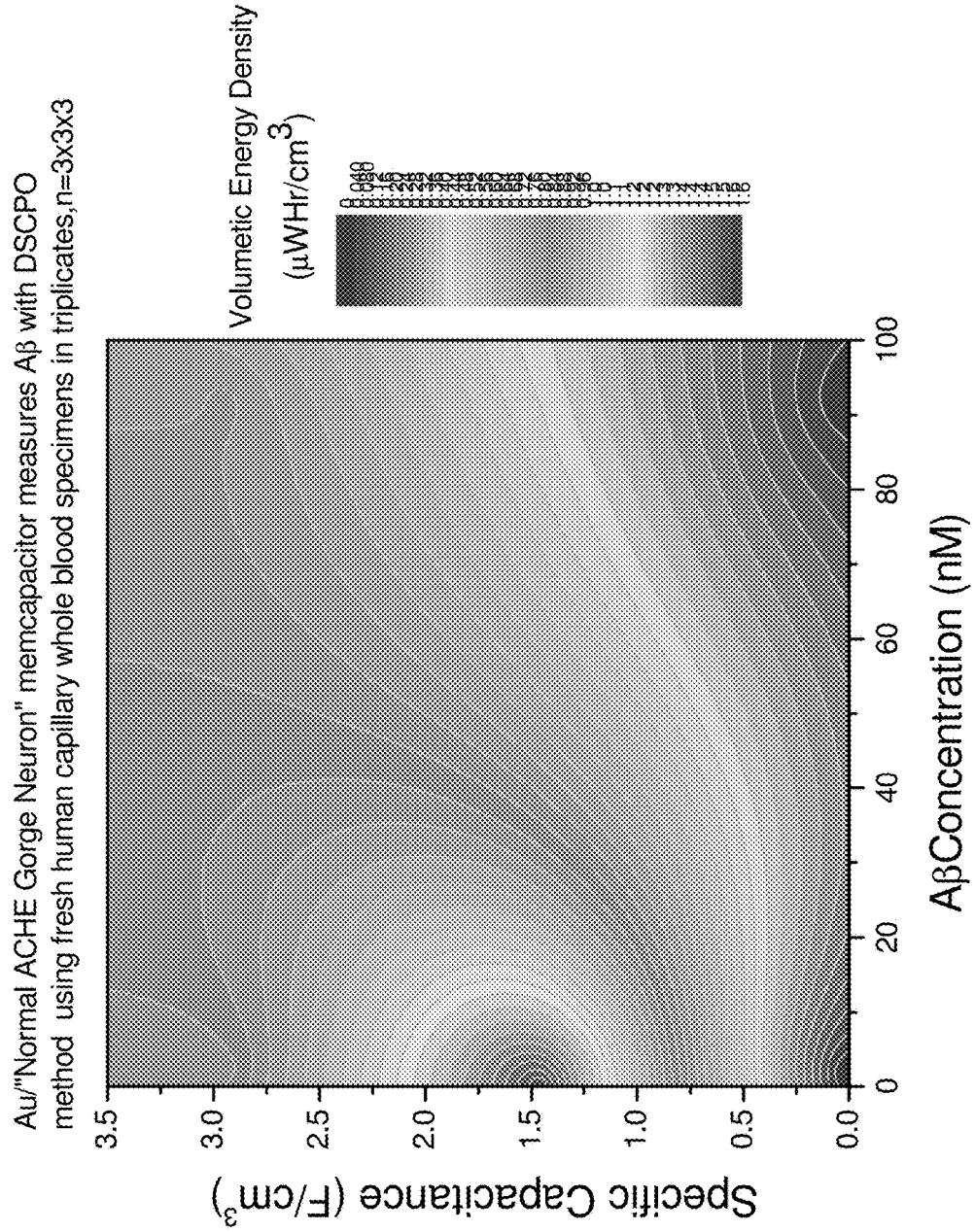

FIG. 33 depicts the voltage sensor's factor map.
FIG. 34 depicts the CA sensor's factor map.

DETAILED DESCRIPTION OF THE INVENTION

Example 1—Fabrication of the Nanostructured Biomimetic Self-Assembling Membranes (SAM) (Literature is Right)

The nanostructured biomimetic ACHE SAM with the vertical bridged conformational "Mutated ACHE Gorge" was freshly prepared. Polyethylene glycol diglycidyl ether (PEG), triacetyl-β-cyclodextrin (T-CD), poly(4-vinylpyridine) (PVP) were purchased from Sigma. PVP was purified before use. The mono derivative dimethyl β-cyclodextrin named as (mM-β-DMCD) was generally synthesized according to the published procedures [20]. The appropriate amount of solutions of individual polymer and reagents were prepared [8]. The mixture solution was made up by mM-β-DMCD (2 g/L to 2.5 g/L, T-CD 2-3 mM, PEG 2 g/L-3 g/L and PVP (40 mg/dL-80 mg/dL), the mixture was incubated in 37 C for 2-3 hrs, then added 0.02M o-NPA with the molar ratio to TCD in the range of (500-1000):1 to the mixture for device 1 with a flat membrane with nanopores. The vertical bridge membrane with nanopores for device 2 did not apply o-NPA. The Au electrode has 50 nm thicknesses and 3 mm in diameter. The mixture solution was injected onto the surface of the electrode and was incubated for 48 hrs at an incubator. After that, the further clean and incubating procedures were followed.

The nanostructured biomimetic "Normal ACHE Gorge" neuronal network SAM with the flat bridged conformation, naopores and lattices was freshly prepared by adding appropriate amount of o-nitrophenyl acetate (o-NPA) into the above described mixture solution for construction of the vertical bridged ACHE SAM.

Example 2—AFM Measurements

Figure 1B:
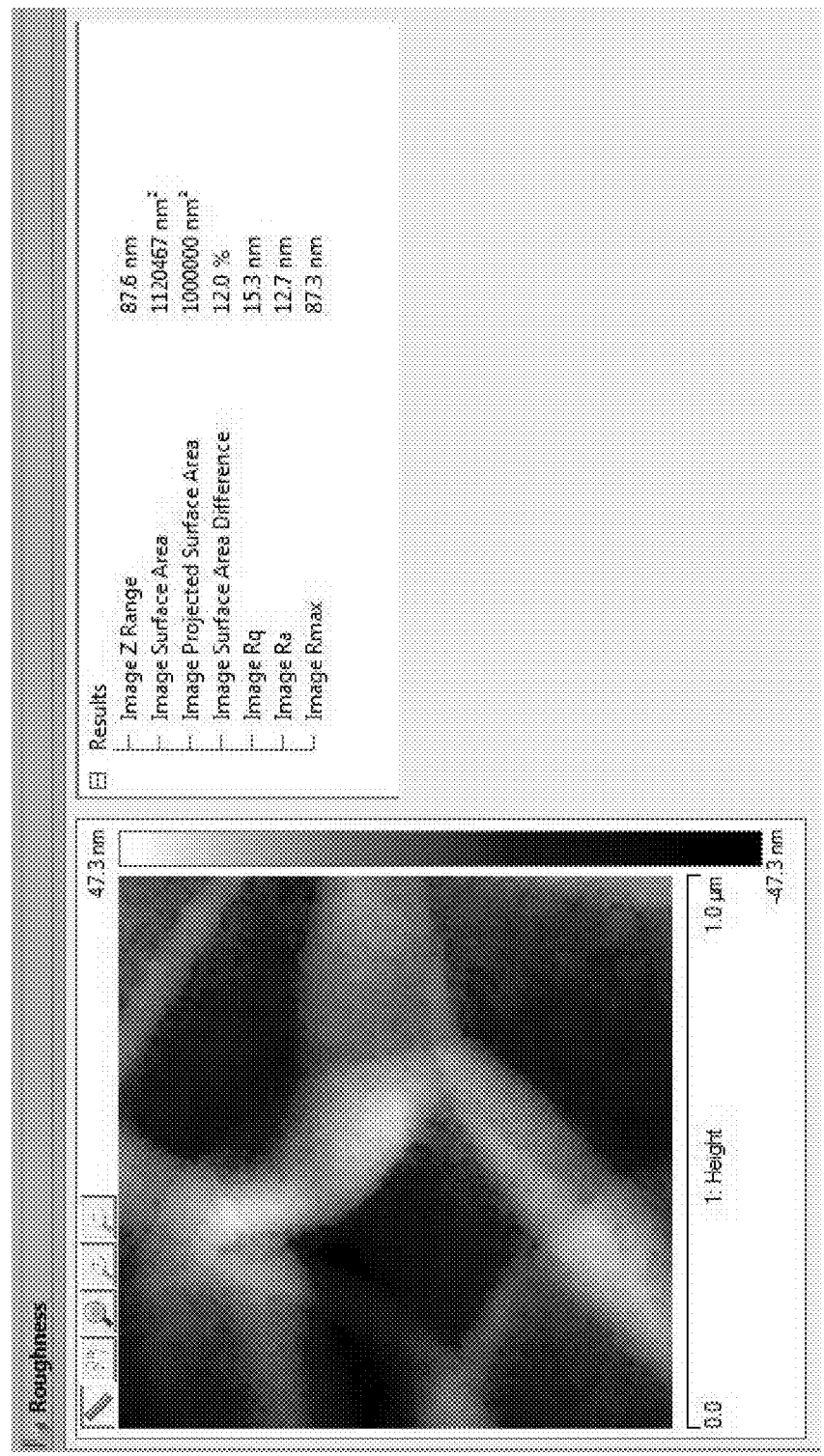
FIG. 1B is the AFM of the Biomimetic "Mutated ACHE Gorge" bridge specifications and the array 3D lattices. The roughness measurements Peak-to-Valley (Z range), and the Root Mean Square (RMS), and Average Roughness ($R_a$) are also shown for this image.
Figure 1C:
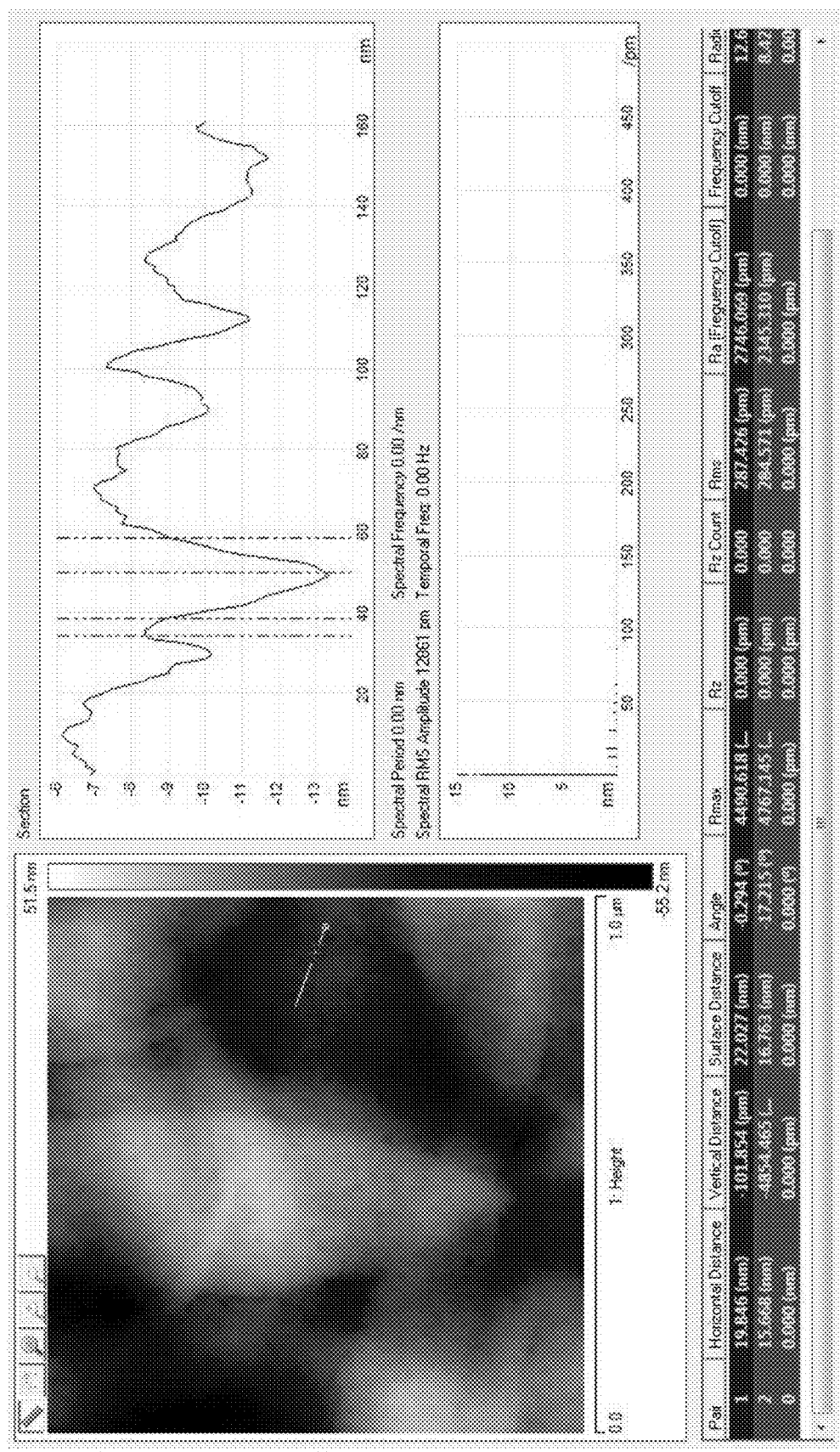
FIG. 1C shows the 2D AFM image of the vertical bridge deepness in cross section analysis.
Figure 1D:
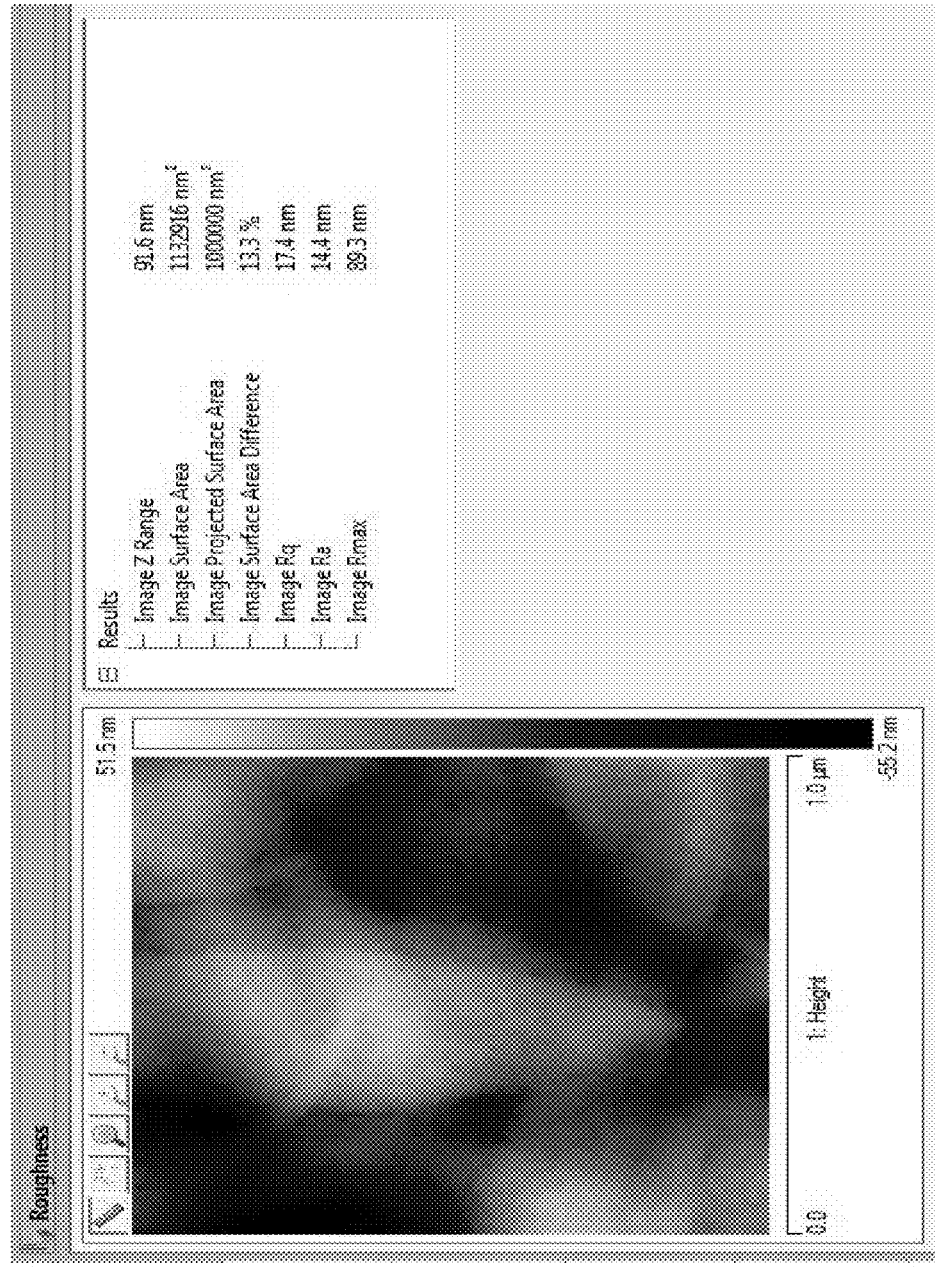
FIG. 1D shows the AFM specification of the surface roughness.
Figure 1E:
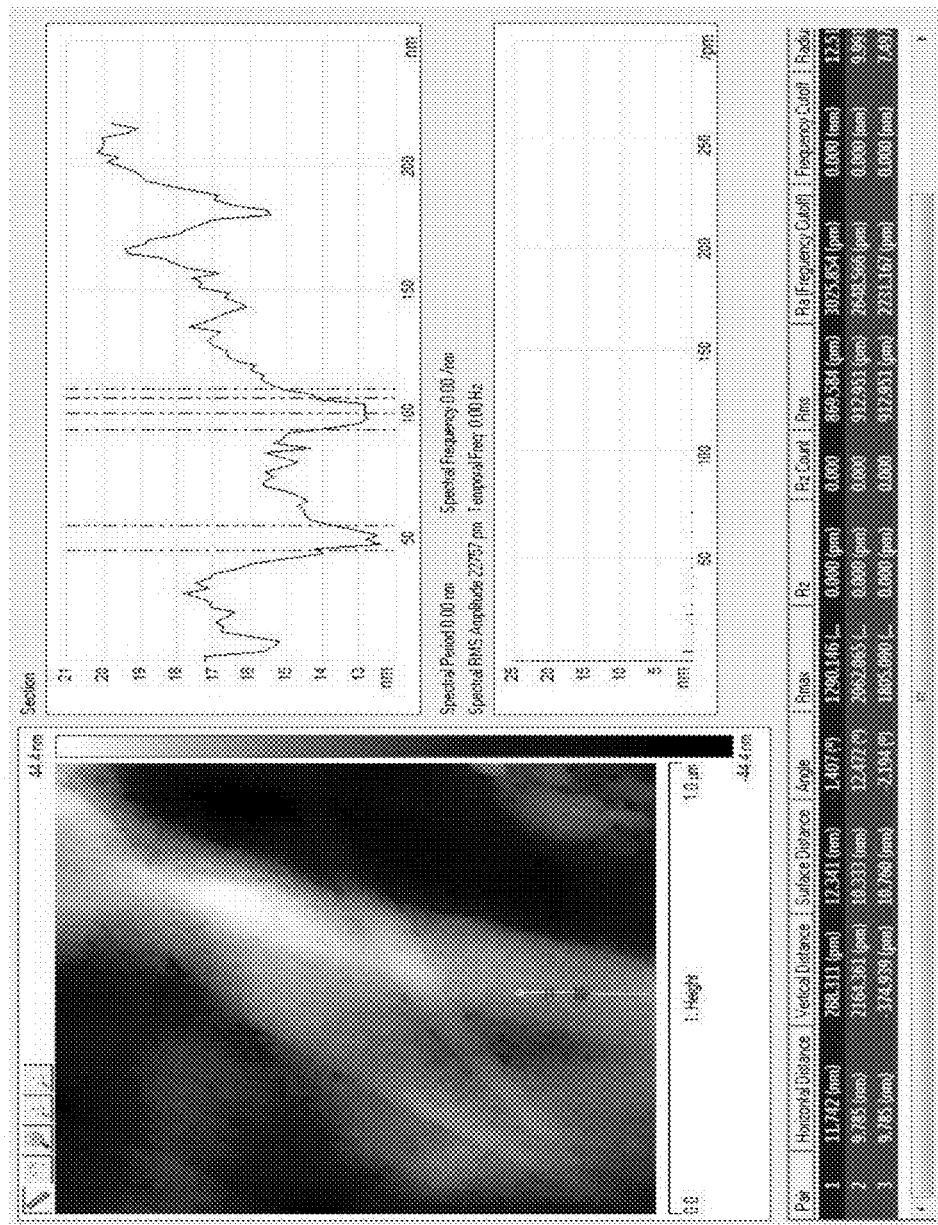
FIG. 1E shows the enlarged AFM of the bridge surface of the cross-section analysis and FIG. 1F is the AFM specifications of the bridge surface.
Figure 1F:
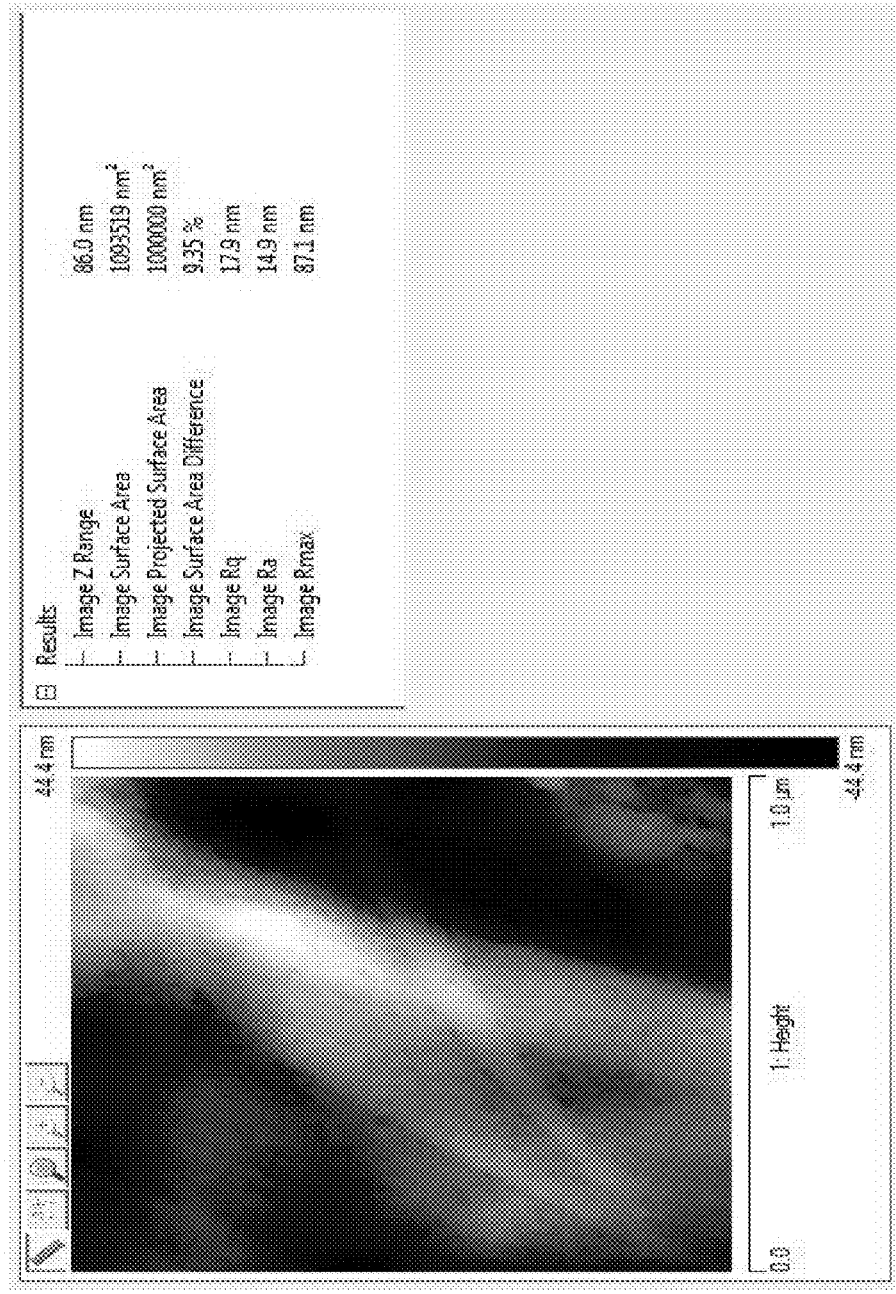
Figure 1G:
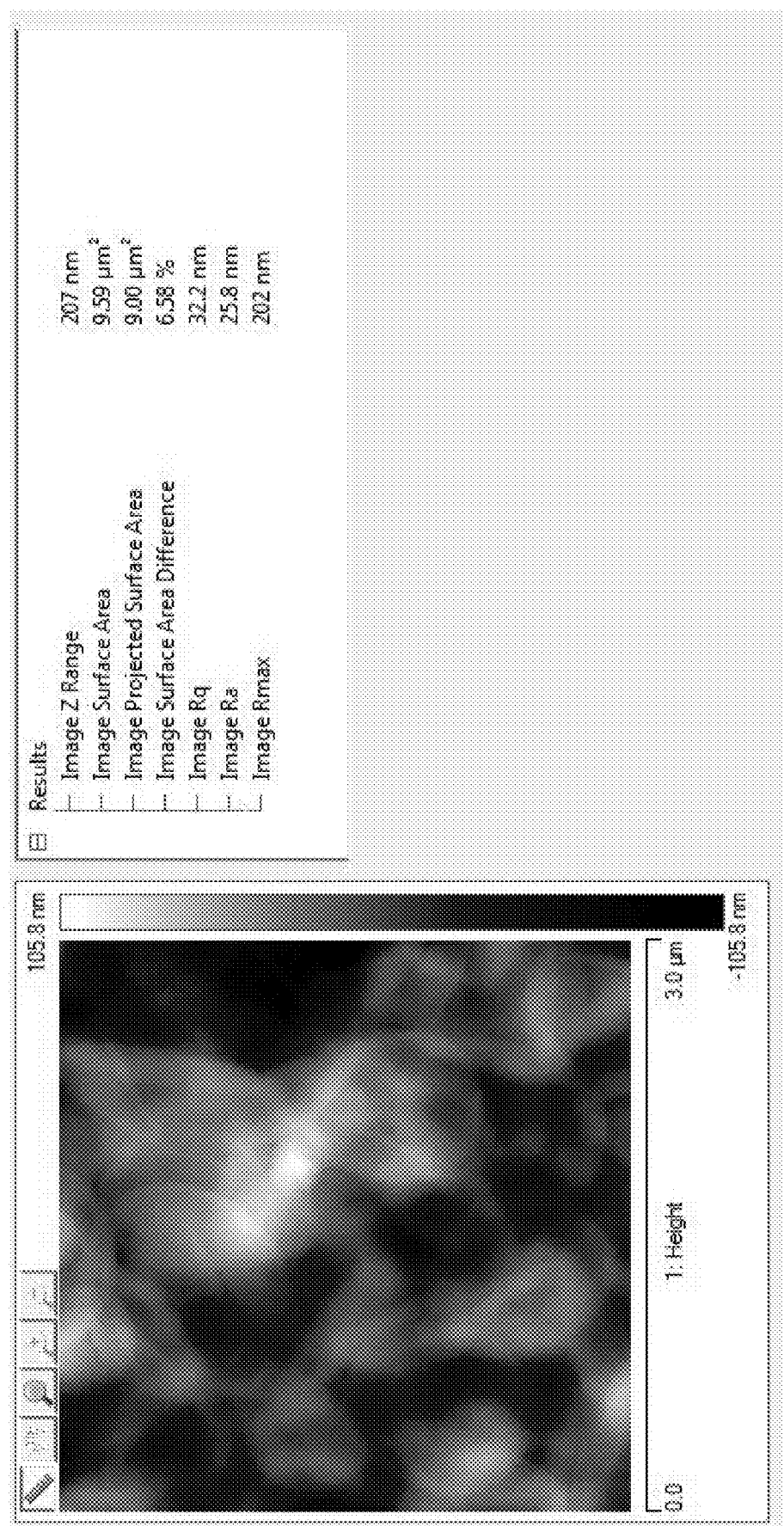
FIG. 1G shows the specifications of the nanoporous existing near the bridge on the surface of the membrane.

The morphology of the three CD-SAMs were characterized by using an instrument (model Multimode 8 ScanAsyst, Bruker, Pa.). Data collected in PeakForce Tapping Mode. Probes used were ScanAsyst-air probes (Bruker, Pa.). The silicon tips on silicon nitride cantilevers have 2-5 nm radius. The nominal spring constant 0.4 N/m was used. NanoScope Analysis v1.40r2 software was used. FIG. 1A illustrates the vertical conformational AFM image of ACHE bridge structure by cross analysis. The average "breathing pore" vertical height by cross section analysis is 3.74 nm with the pore width of 12.2-18 nm and the RMS (surface morphology) is 3.55 nm. The lattice distributed pores can be seen in the image. The bridge vertical height is 47.3 nm with the length of 940 nm. FIG. 1B illustrates the membrane specifications in roughness is 15.2 nm and the membrane surface thickness is 47.3 nm. FIG. 1C shows the bridge vertically oriented of 51.5 nm, underneath of the bridge is the "breath pore" with pore diameter of 15-20 nm and depth of 0.5 nm and the surface roughness is 0.287 nm. FIG. 1D shows the membrane surface roughness is 17.4 nm. FIG. 1E shows the AFM image of the shining horizontal cross bar associated with the vertical bridge of FIG. 1A. The cross bar channel width is 200-600 nm and height is 44.4 nm, and length is 1100 nm. Underneath of the bridge are "breathing pores" of 0.2 nm in depth and 10-12 nm in diameter with RMS value 0.9 nm. FIG. 1F shows the membrane surface morphology in 17.9 nm. FIG. 1G shows the AFM in a larger window view of 9 $\mu m^2$ and we can see the breathing pores distributed evenly filled inside of each orderly square lattices and the bridges are on top with a vertical fall difference of 50-100 nm.

Figure 2A:
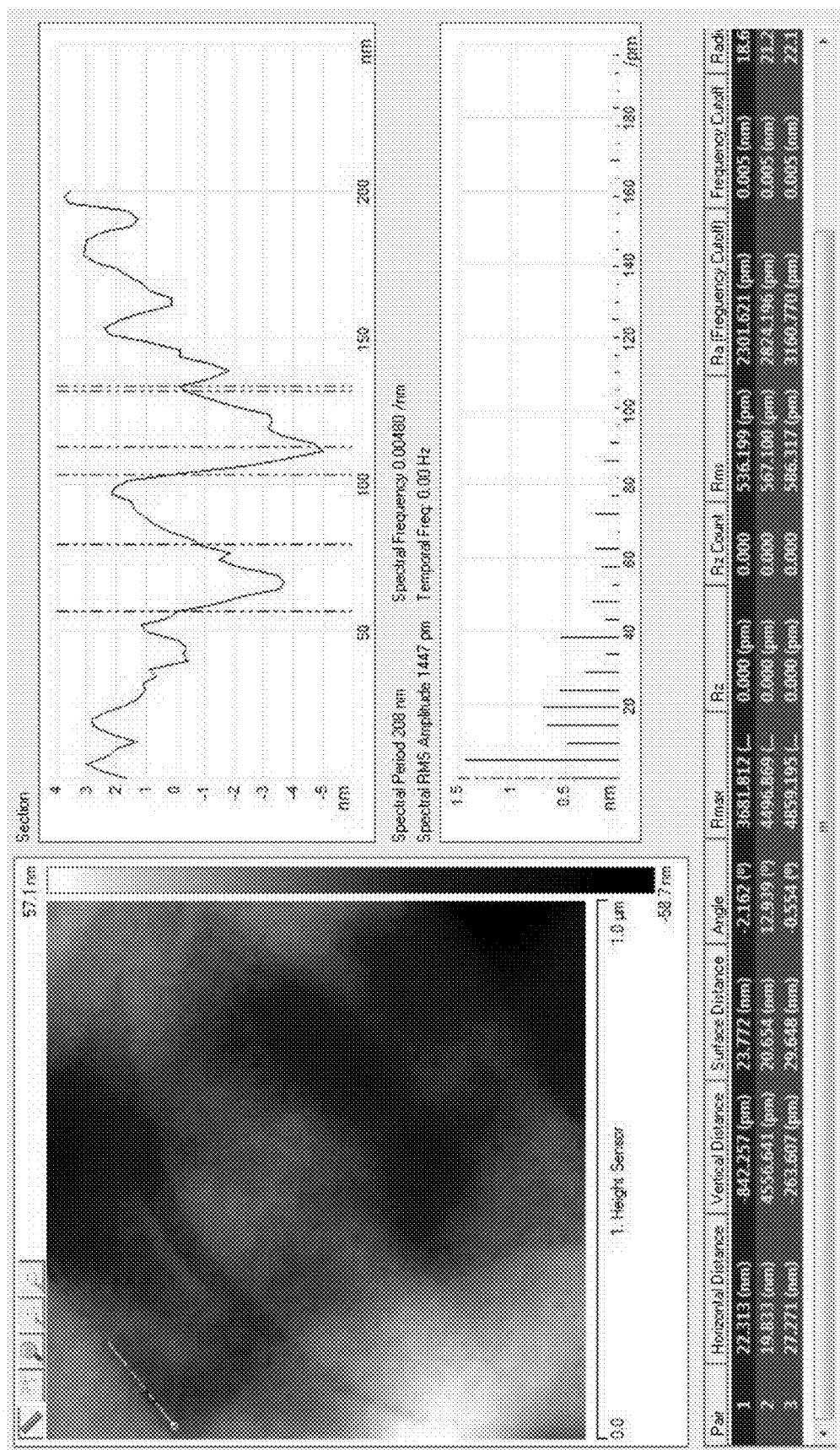
FIG. 2A shows the AFM image of the nanostructured biomimetic "Normal ACHE Gorge" with a flat horizontal bridge and the cross section analysis results were shown in the table listed below.
Figure 2B:
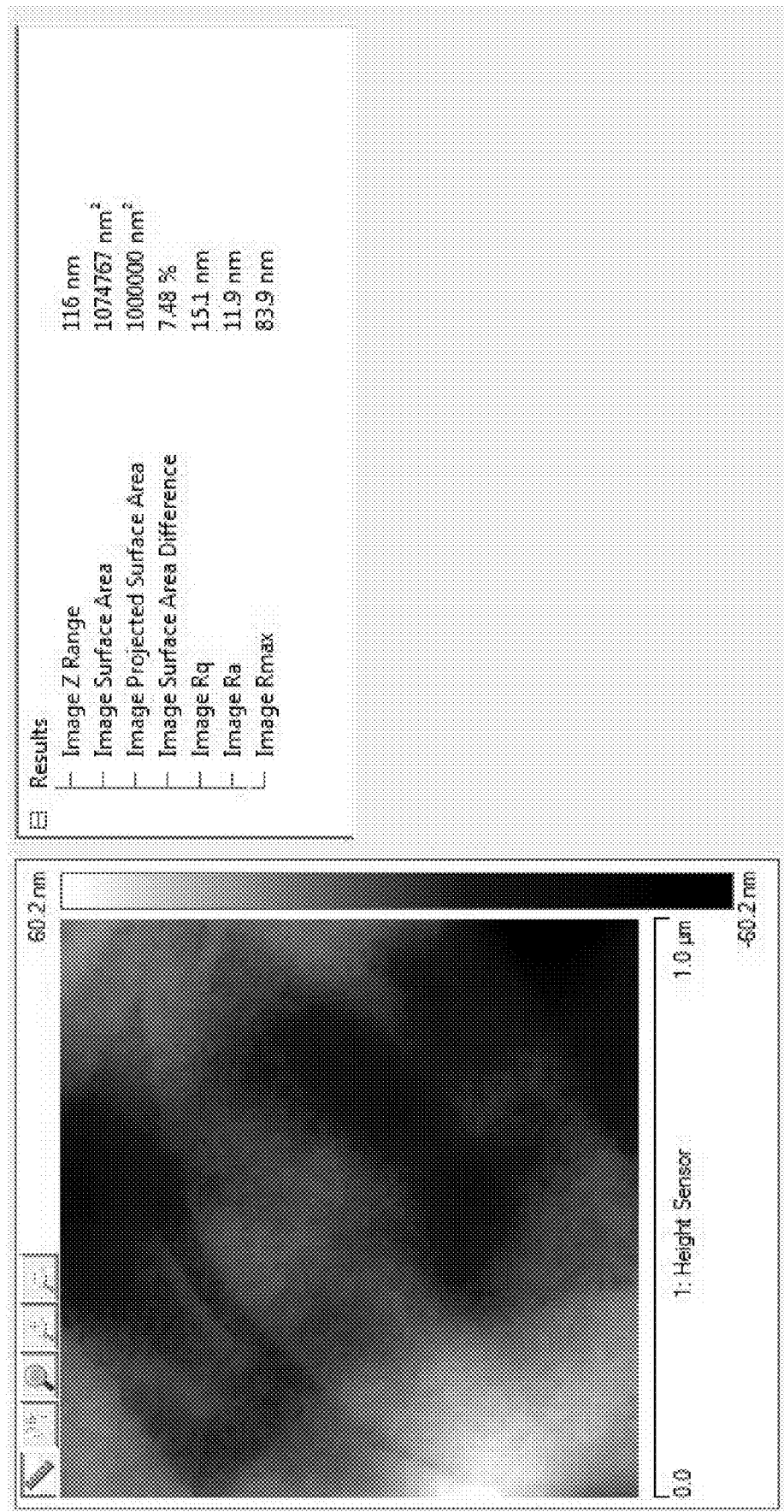
FIG. 2B is the AFM of the biomimetic "Normal ACHE Gorge" flat bridge specifications with the roughness values are also shown for this image.
Figure 2C:
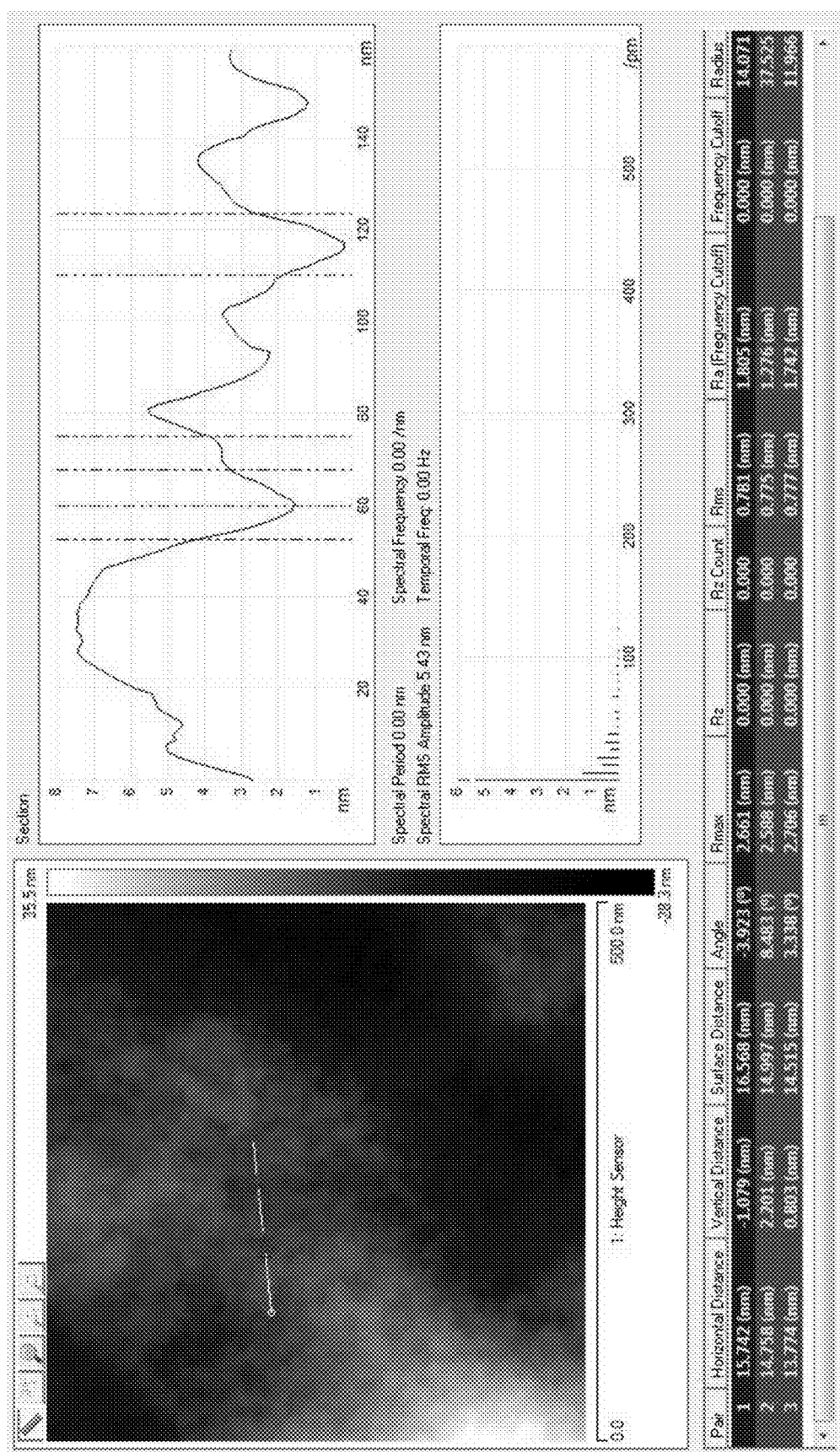
FIG. 2C shows the close look of the bridge surface in cross section analysis.
Figure 2D:
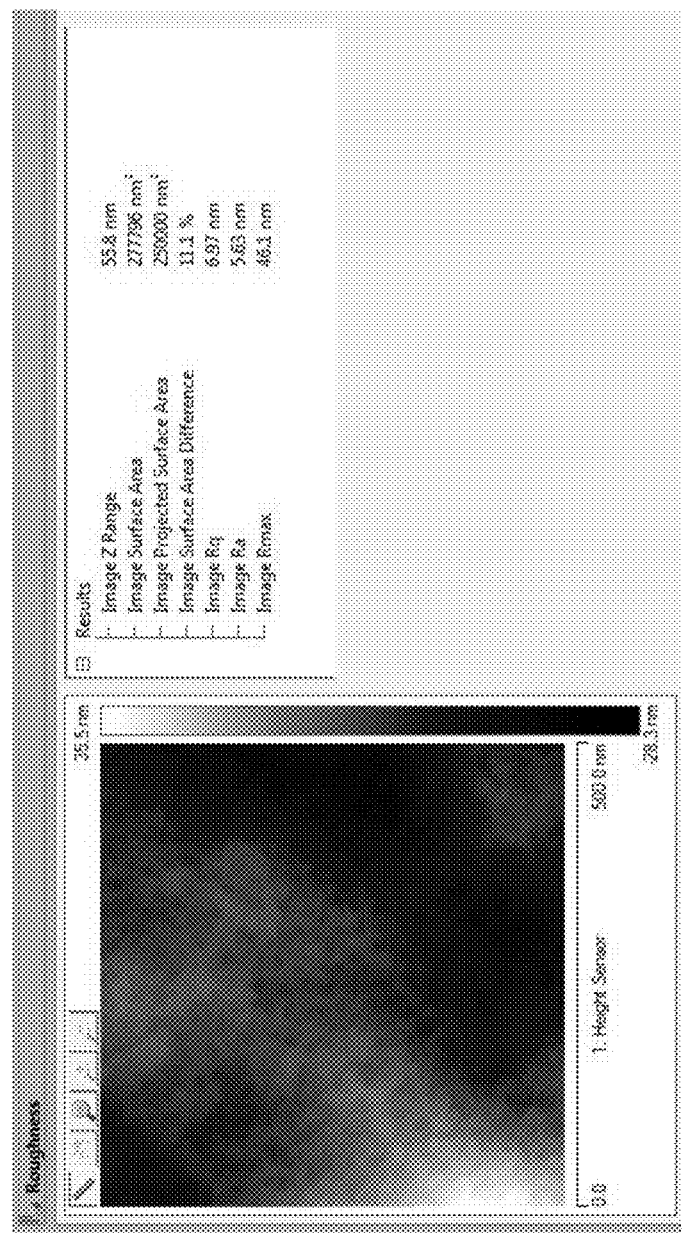
FIG. 2D shows the AFM specification of the surface roughness of the bridge.
Figure 2E:
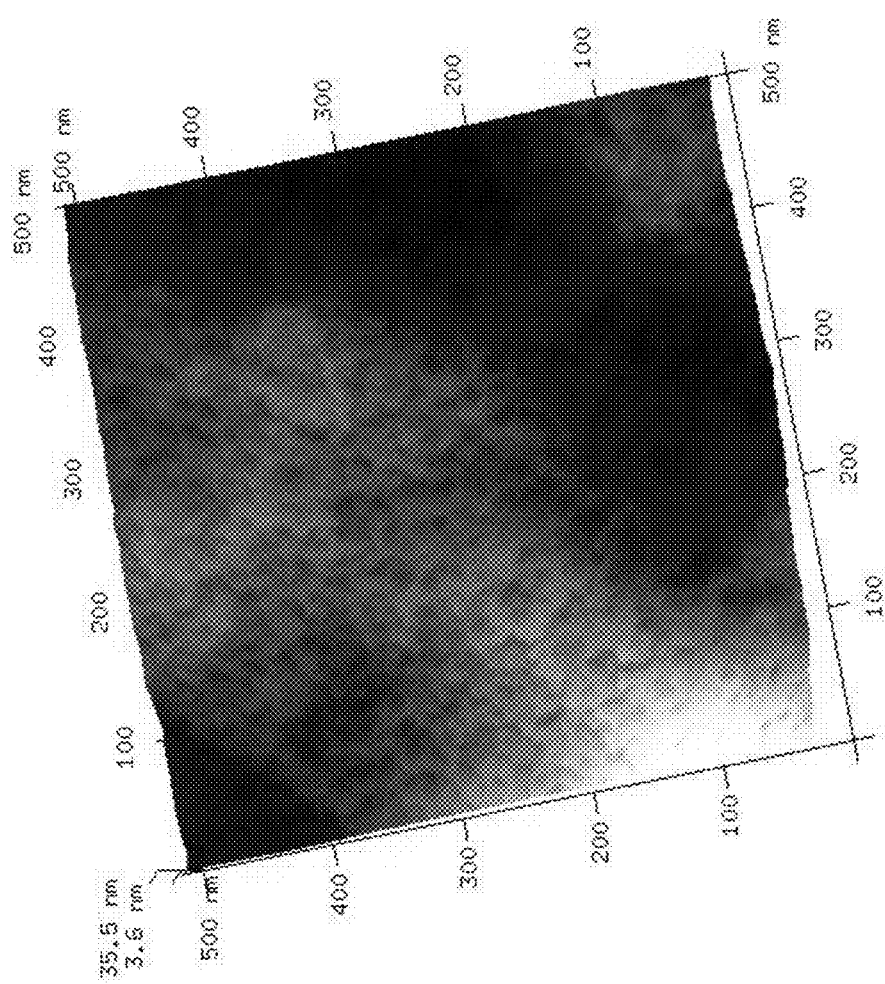
FIG. 2E depicts the body of the horizontal flat bridge was densely covered with thousands uniformly and orderly orientated donuts shaped "fish scales", density of $10^7$ pores/cm$^2$, with the average donuts size of 22 nm in diameter and the pores in the center are 9-10 nm in diameter.
Figure 2F:
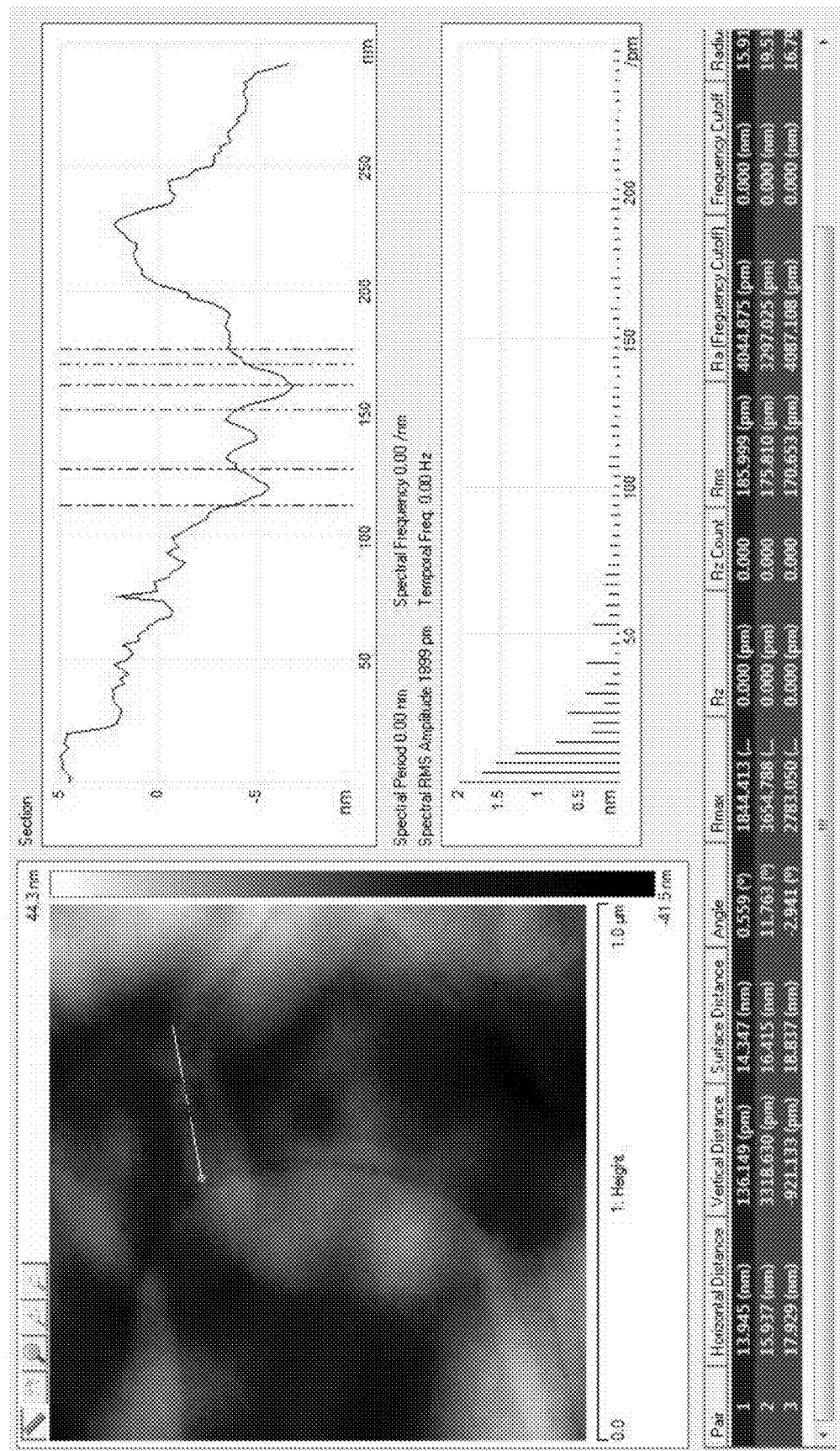
FIG. 2F shows the enlarged AFM of the nanopore nearby the bridge for the cross-section analysis and FIG. 2G depicts the AFM results specifications of the nanoporous.
Figure 2G:
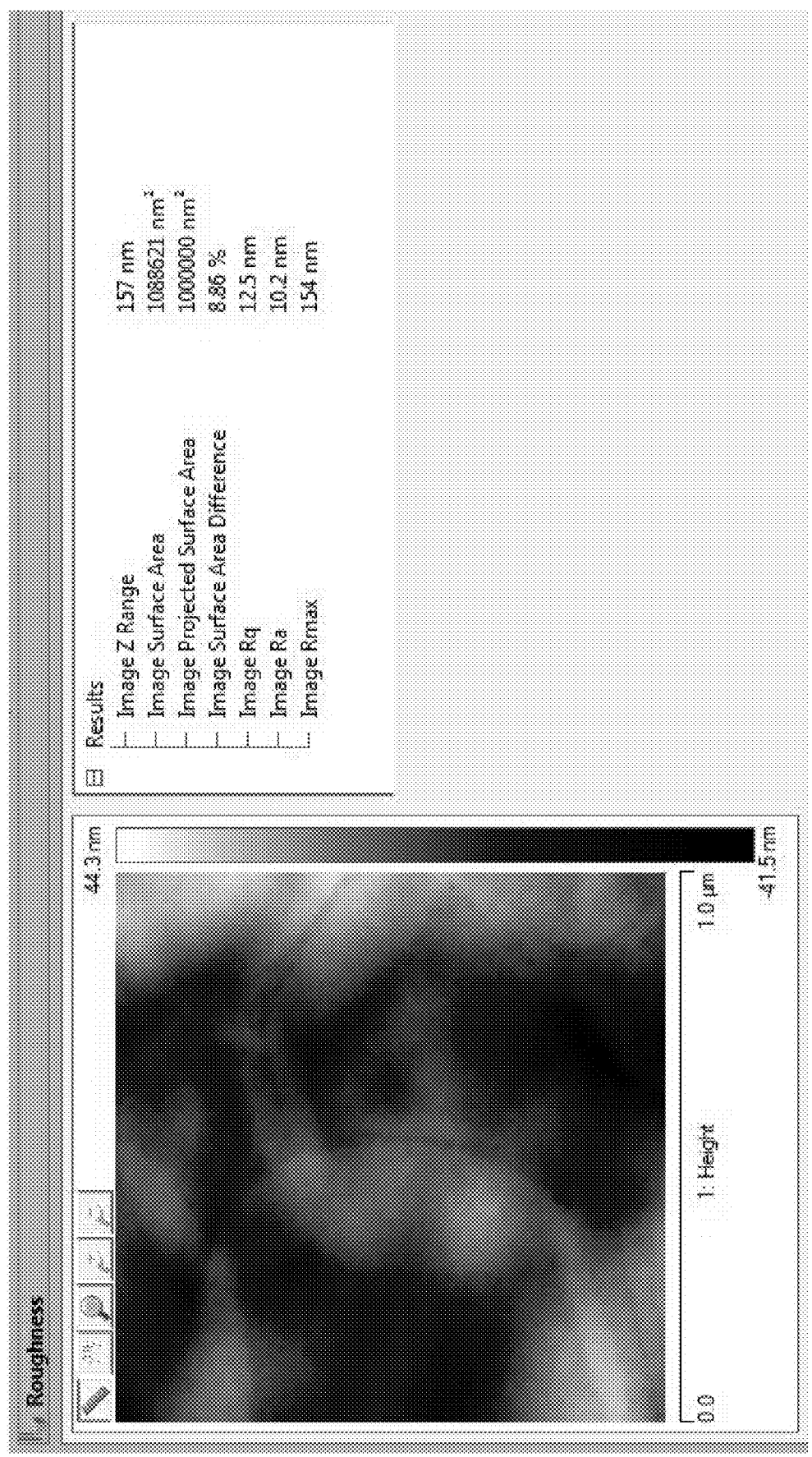

The significant structures difference from figures shown above are the SAM fabricated by added o-NPA in the mixture of mM-β-DMCD, T-CD, PEG and PVP, that formed a flat bridge with nanopores. FIG. 2A shows the flat bridge with width 330 nm and length in 1.4 μm by cross section analysis with RMS 0.6 nm in the image. Nanopores can be seen on each side of the bridge; the pores on the left side of the bridge have a depth 0.3-0.8 nm and diameter 20-30 nm. FIG. 2B shows the membrane morphology specification in thickness 60.2 nm with the roughness 15.1 nm. FIG. 2C shows the pore size having 14-16 nm diameters on the right hand side of the flat bridge with the pore depth 0.1-2.3 nm by the cross-analysis AFM. The RMS value is 0.8 nm in a small scale view window of 500×500 nm. FIG. 2D is the AFM results of FIG. 2C with the pores in the membrane thickness 55.8 nm. FIG. 2E depicts the body of the horizontal flat bridge was densely covered with thousands uniformly and orderly orientated donuts shaped "fish scales", density of $10^7$ pores/cm$^2$, with the average donuts size of 22 nm in diameter and the pores in the center are 9-10 nm in diameter shown in FIG. 2E. FIG. 2F shows the AFM image of the "breathing pore" near the flat cross bridge with the pore length among 12-18 nm and the vertical pore depth is 0.1-3.0 nm and the RMS is 0.18 nm by the cross section analysis. FIG. 2G shows the AFM results with pores presence with the membrane thickness 157 nm and the membrane roughness is 12.5 nm.

Example 3—Fabrication of the Au/SAM Nano-Island Membrane

Figure 3A:
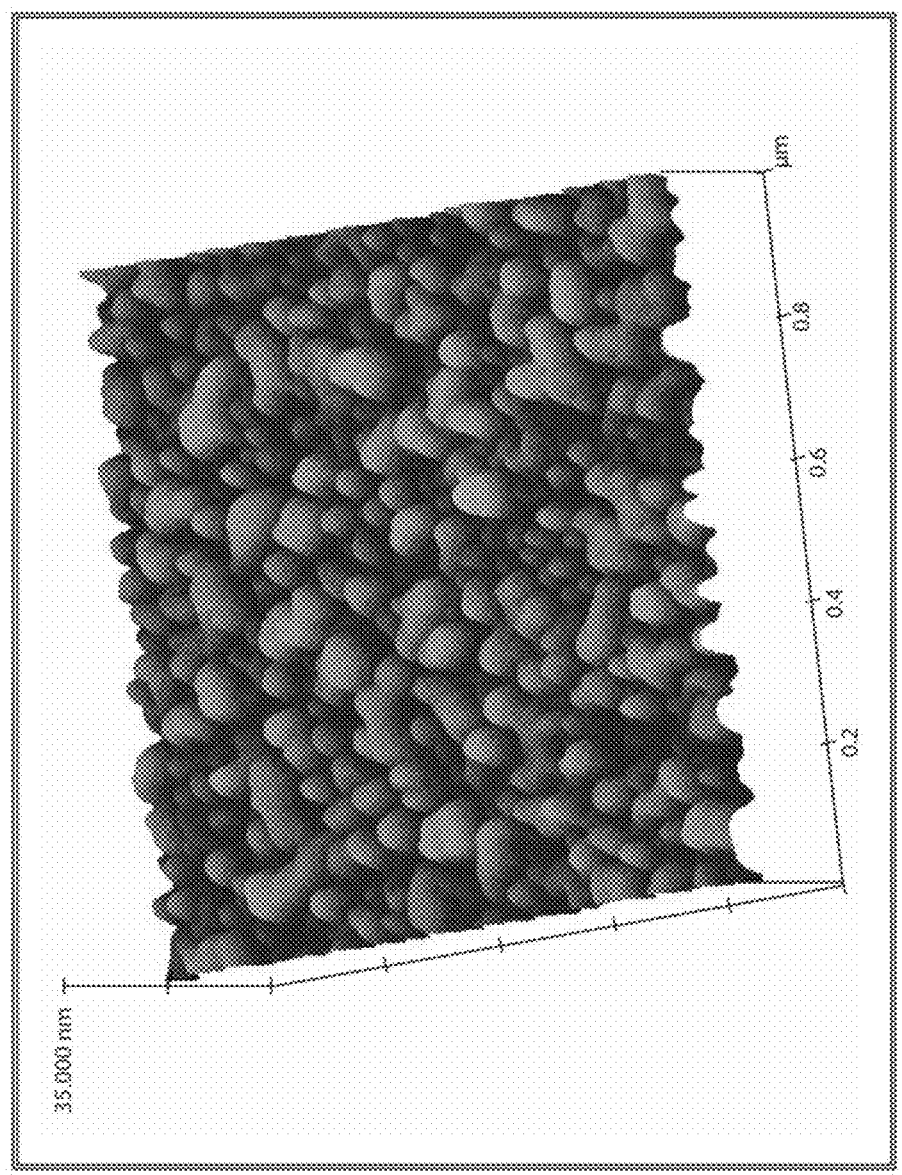
FIG. 3A depicts an AFM images for a Au/MEA with TCD/PVP/PEG/β-CD copolymer with 3D islands structure.
Figure 3B:
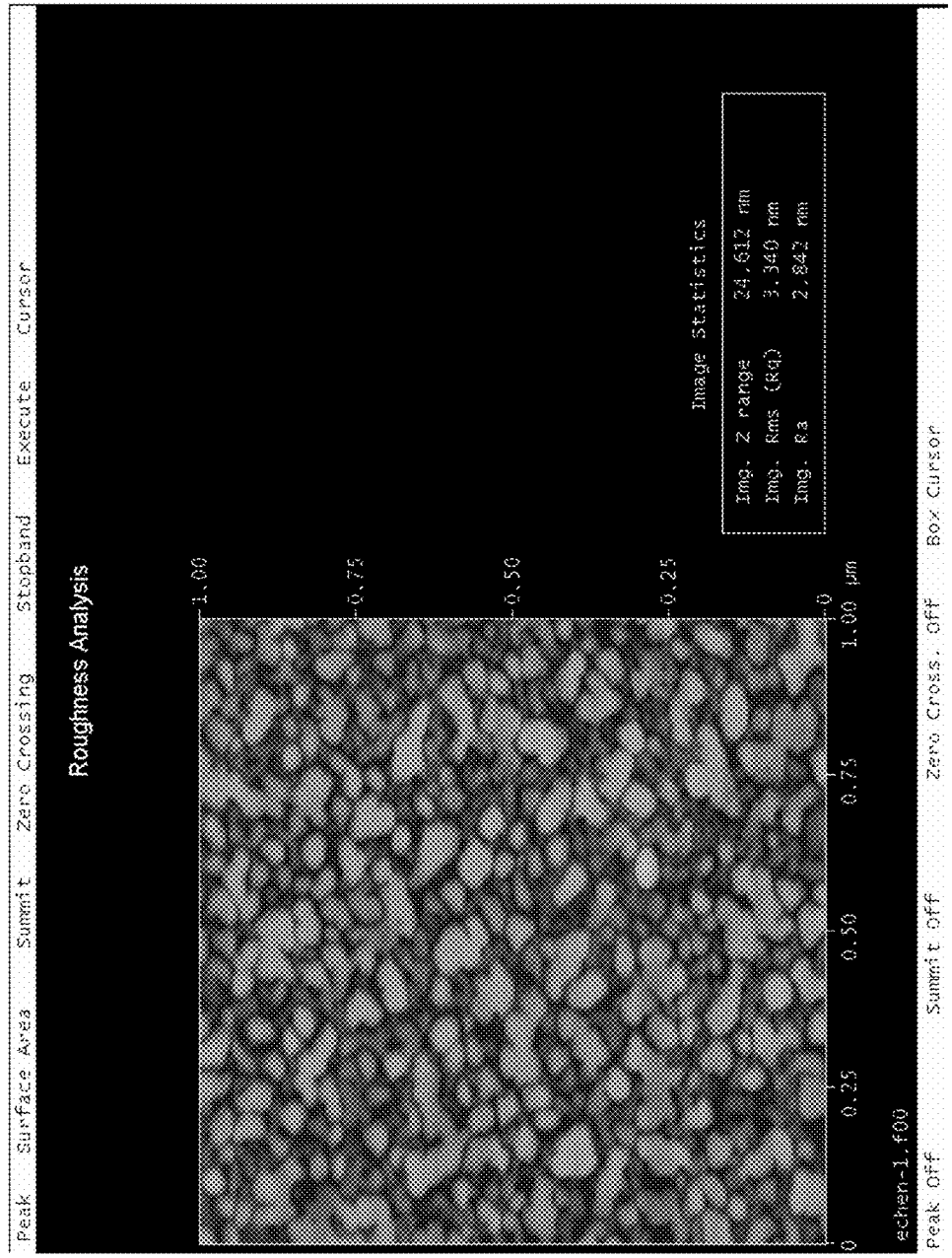
FIG. 3B depicts the AFM images results of Z range, RMS and Ra results.

The nano-island Au/SAM compromised with Au/triacetyl-β-cyclodextrin (T-CD), poly(4-vinylpyridine) (PVP) and Polyethylene glycol diglycidyl ether (PEG)/copolymer β-CD. The procedures of making were disclosed in the U.S. Pat. No. 8,083,926 and the references were included. FIG. 3A depicts the AFM nano-island structure on a pure gold chip and FIG. 3B depicts the membrane thickness is 24.6 nm, the surface smoothness in RMS is 3.3 nm, and the Ra value is 2.84 nm.

Example 4—Mimicking the Active ACHE Gorge and its Linen (Literature is √)

Figure 4B:
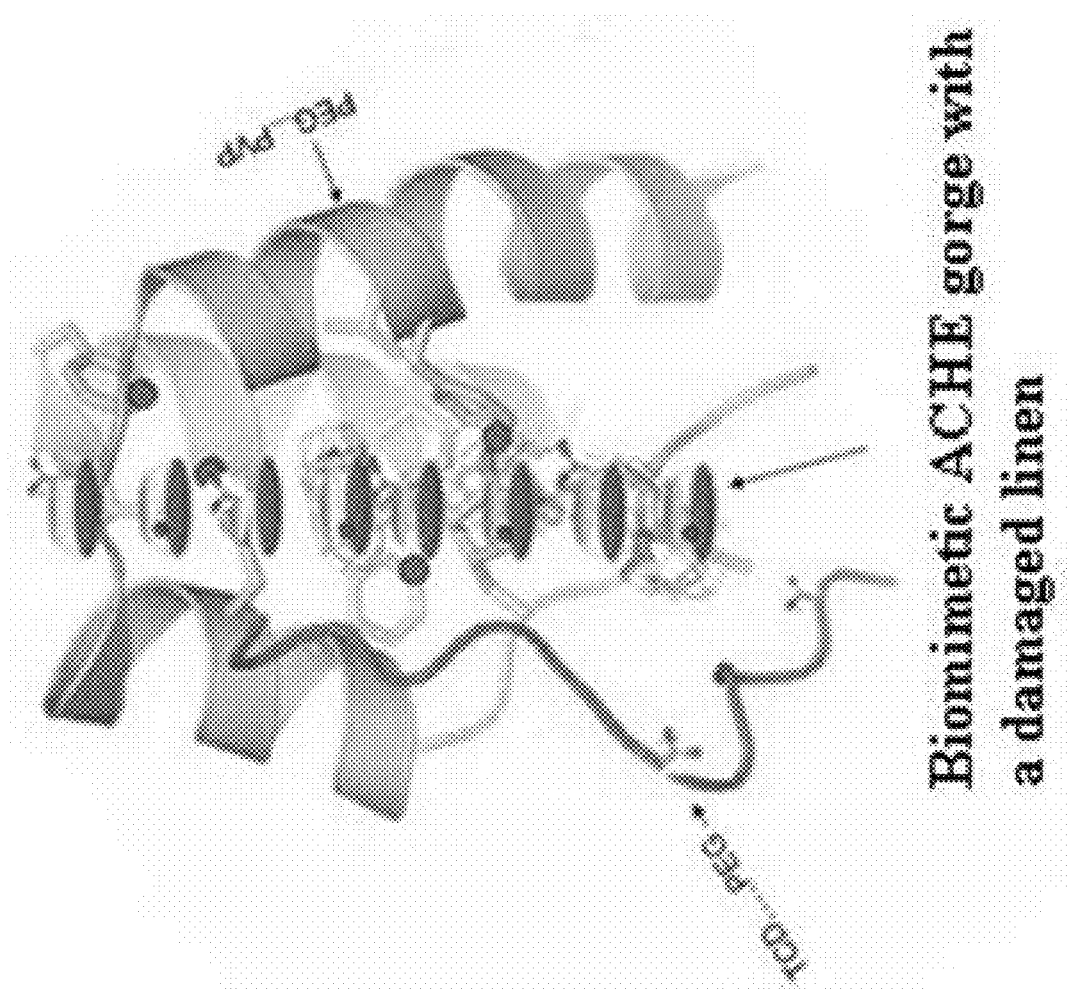
FIG. 4B depicts the art illustration of the SAM molecular polymer architecture for memristor sensor 2 as the model for a "Mutated ACHE Gorge".

A "Normal Active Site ACHE Gorge" was defined as a linen-cylinder consists of a bipolar dome with two poles. (1): the positive isopotential pole: esteratic site of five residues containing the catalytic triad (Ser-200, Glu-327, His-440), acyl pocket Phe 288 and Phe-290 [6-8], that was mimicked by polyethylene glycol diglycidyl ether (PEG) (for Ser 200) . . . imidazolyl-dimethyl-β-cyclodextrin (M-CD) (for His 440) . . . triacetyl-β-cyclodextrin (T-CD) (for Glu327). Phe288 and 290 were mimicked by o-NPA. (2) The 14 aromatic residues for gorge lining were mimicked by excess amount of o-NPA (1:500-1000 of T-CD/o-nithophenyl acetate (o-NPA)) and W84 were mimicked by poly(4-vinylpyridine) (PVP). (3) the negative isopotential pole: the Asp-72, Tyr-121, Tyr-70, Tyr-354, and Trp-279 are the residues of the peripheral and were mimicked by TCD . . . PEG polymer and TCD . . . PVP polymers as anionic site (PAS), F330, Y121 were mimicked by o-NPA, and Trp279 was mimicked by PVP. By knock out all o-NPA out of the network, we define the second device as "Mutated Active Site ACHE Gorge" based on our hypothesis: Lacking of hydrophobic lining in the gorge might be the key issue caused diseases, because the nature of the ACHE gorge might be mem-ristive, mem-capacitive and meminductive in nature. FIG. 4A and FIG. 4B depict the Biomimetic ACHE gorge of a "normal brain" and a "mutated brain" gorges, respectively.

Figure 6:
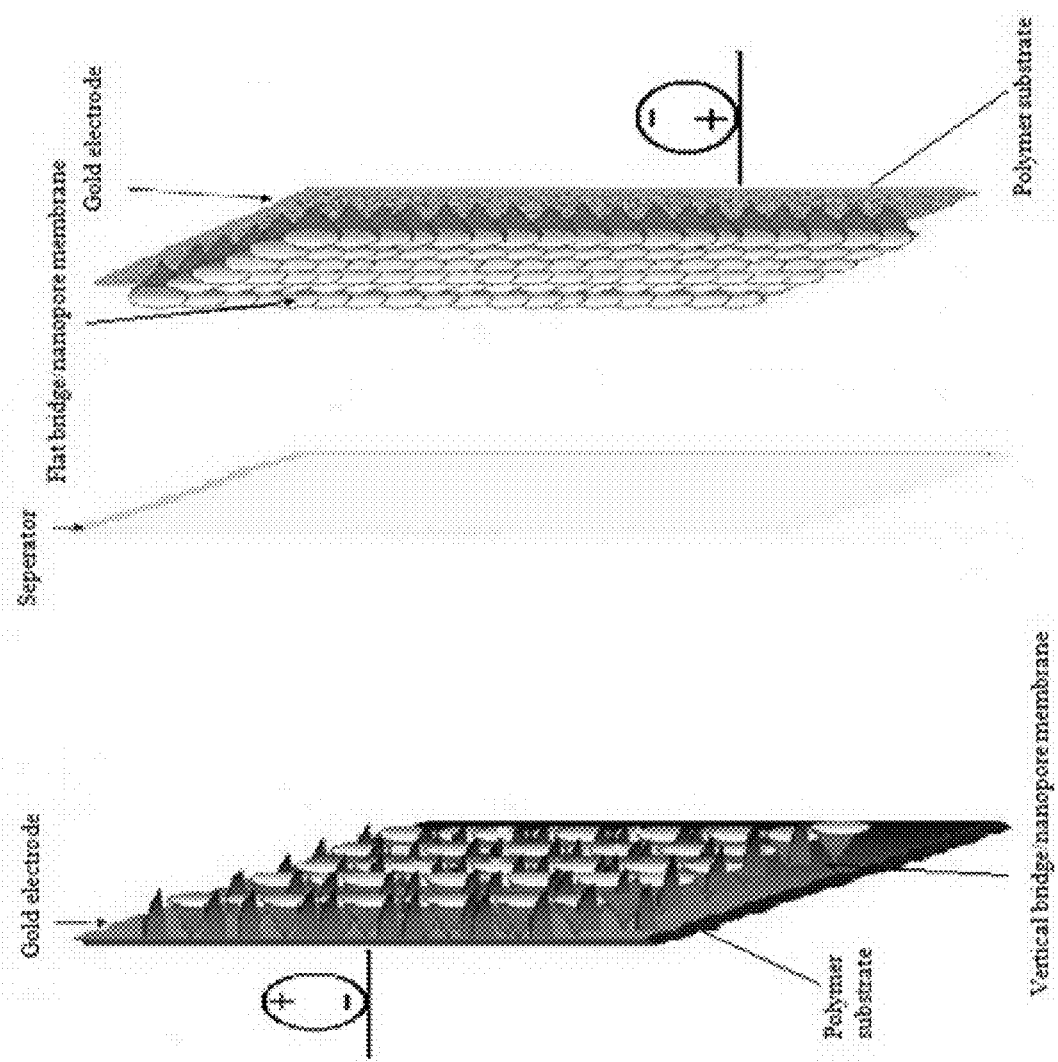
FIG. 6 depicts Memcapacitor 2 as a neuron network for the "Predator".
Figure 7A:
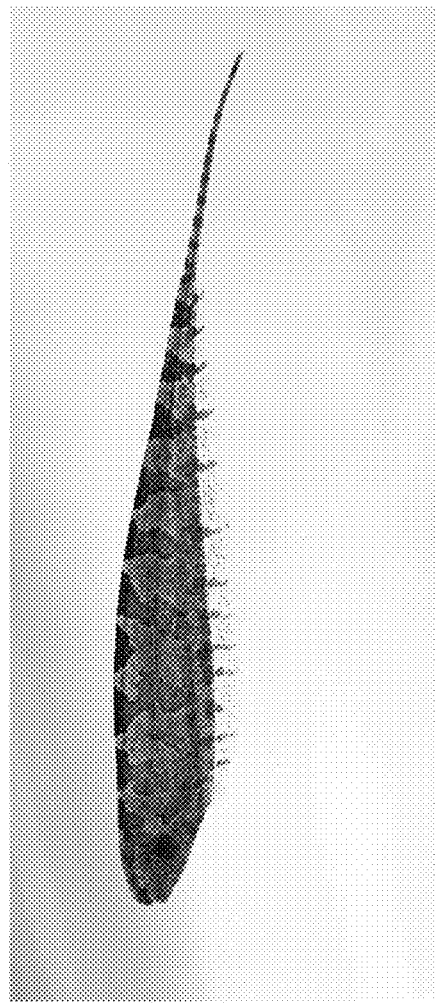
FIG. 7A depicts the image of the BHE fish.
Figure 7B:
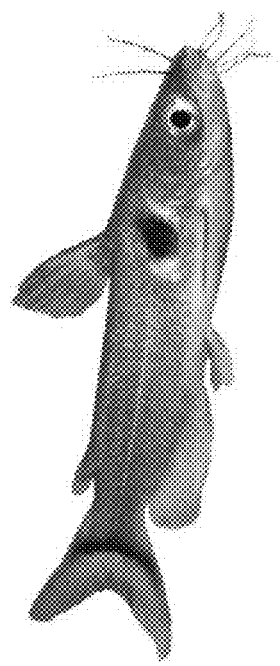
FIG. 7B depicts the image of the catfish as "Predator".

Example 5—Asymmetric Engineering Design of the Organic Memristor/Memcapacitor Devices The morphology of the AU/SAM was characterized using an Atomic Force Microscope (AFM) (model Multimode 8 ScanAsyst, Bruker, Pa.). Data Collected in PeakForce Tapping Mode. Probes used were ScanAsyst-air probes (Bruker, Pa.) and the nanostructured SAMs were published in literature [21]. An asymmetric design for the biomimetic ACHE neuronal memristor/memcapacitor of BHE mimicking fish was illustrated in FIG. 5 and the mimicking predator catfish of the memristor/memcapacitor was depicted in FIG. 6. It was defined as "BHE fish" as shown in FIG. 7A, and it consists of a nanoisland self-assembling Membrane (SAM) Au/triacetyl-β-cyclodextrin (T-CD), poly(4-vinylpyridine) (PVP) and Polyethylene glycol diglycidyl ether (PEG)/ copolymer β-CD as one Membrane Electrode Assembling (MEA) separated by a insulator and connected with another MEA of Au. The monoimidazolyl derivative dimethyl β-cyclodextrin (M-CD)/TCD/PVP/PEG/embedded with o-nitrophenyl acetate (o-NPA) through Pt current collectors at two ends. The insulator absorbed 1M methanol as model 1. The Atomic Force Microscopy (AFM) images and membrane fabrication methods were reported in literature [8, 20]. An asymmetric design for the Biomimetic "Predator Fish", the Catfish, shown in FIG. 7B. The memcapacitor consisted of Au/MCD/TCD/PVP/PEG with structure of vertical bridge/nanopore MEA separated by an insulator and connected with a Au/MCD/TCD/PVP/PEG embedded with o-NPA forming flat bridge/nanopopore memcapacitor as model 2 shown in FIG. 6. The AFM images were reported in literature 20.

Example 6—Characteristics of the Memristors

Memristor's characteristic i-V curves and the diverging frequency were studied using CV method at 20 mV/s scan rate in room temperature. Memristors are devices made of nanolayers that have the capability to mimic neuronal synapse with a characteristic of hysteresis loop in the i-V curve [22-26]. A memristor is a semiconductor whose resistance varies as a function of flux and charge. This allows it to "remember" what has passed through the circuit [22-26]. $G(\{x\},t)$ which is state dependent $$I(t)=G(\{x\},V,t)V(t) \quad (1)$$

Figure 8:
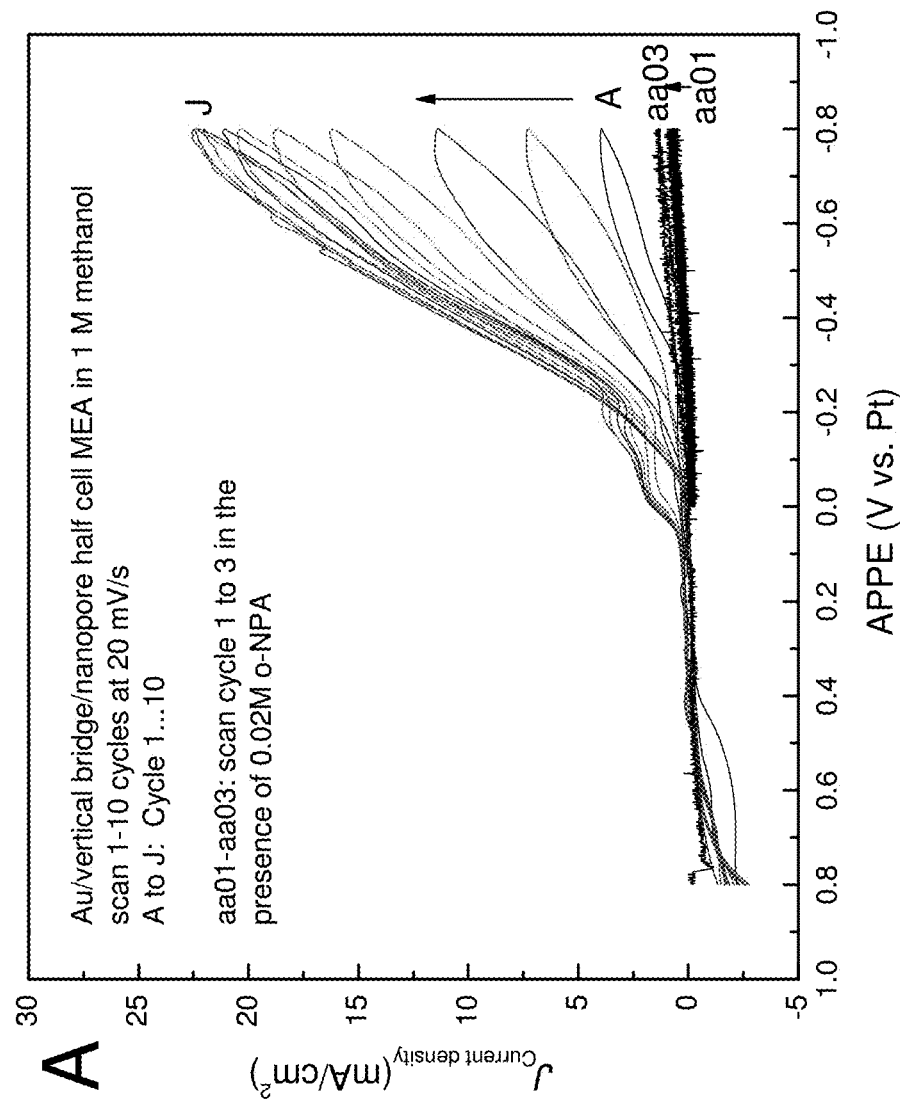
FIG. 8 depicts the AU/"vertical nanopore"/Pt half cell MEA with 10 cycle as curves from A to J with scan rate 20 mV/s and the switch cross-point in 1 M methanol compared the curves in the presence of 0.02M o-NPA in 1M methanol from aa01 to aa03.
Figure 9:
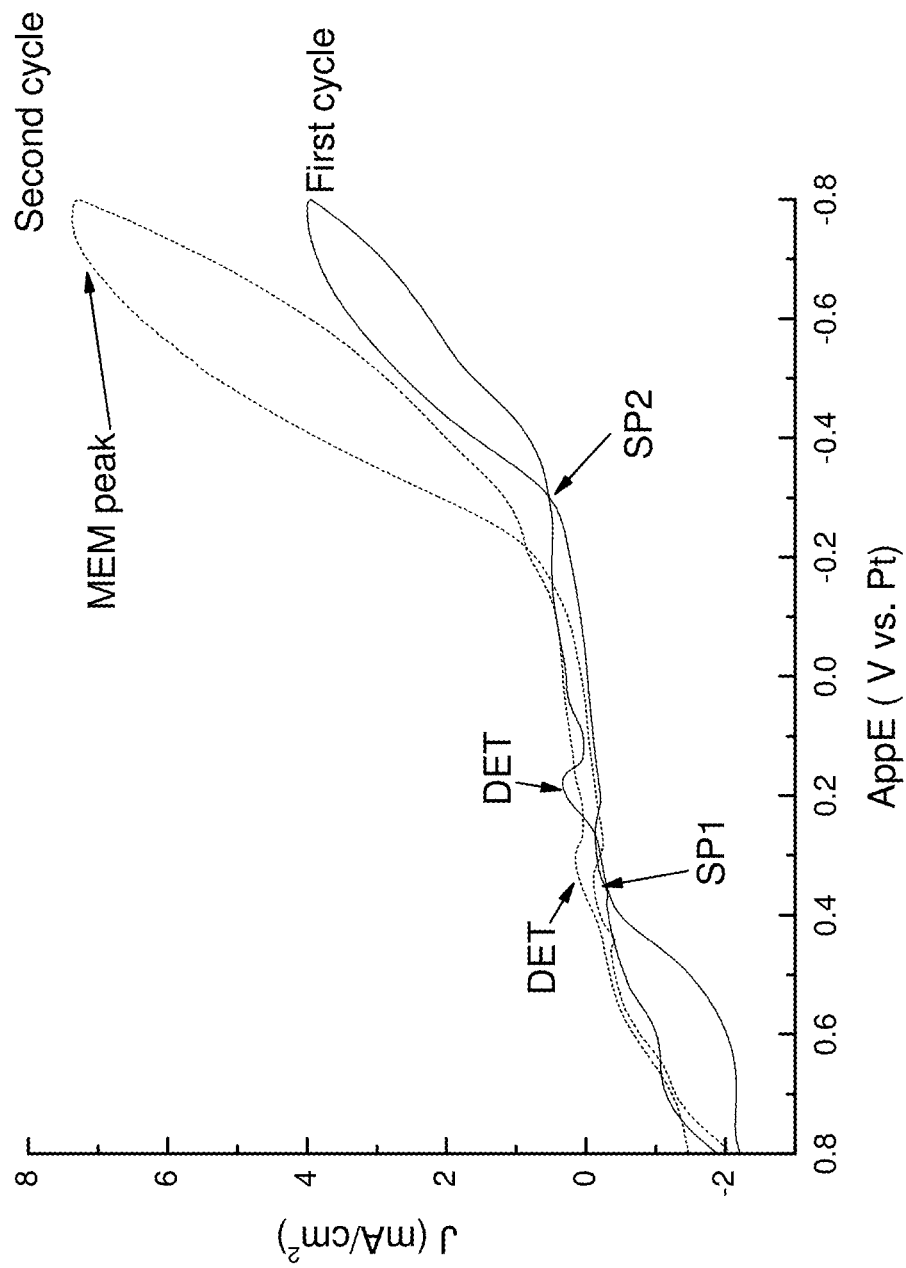
FIG. 9 illustrates the DET peak and the switch point (SP) signed from the first and second cycle in FIG. 8 and signed the DET peak and the Sp locations.
Figure 10:
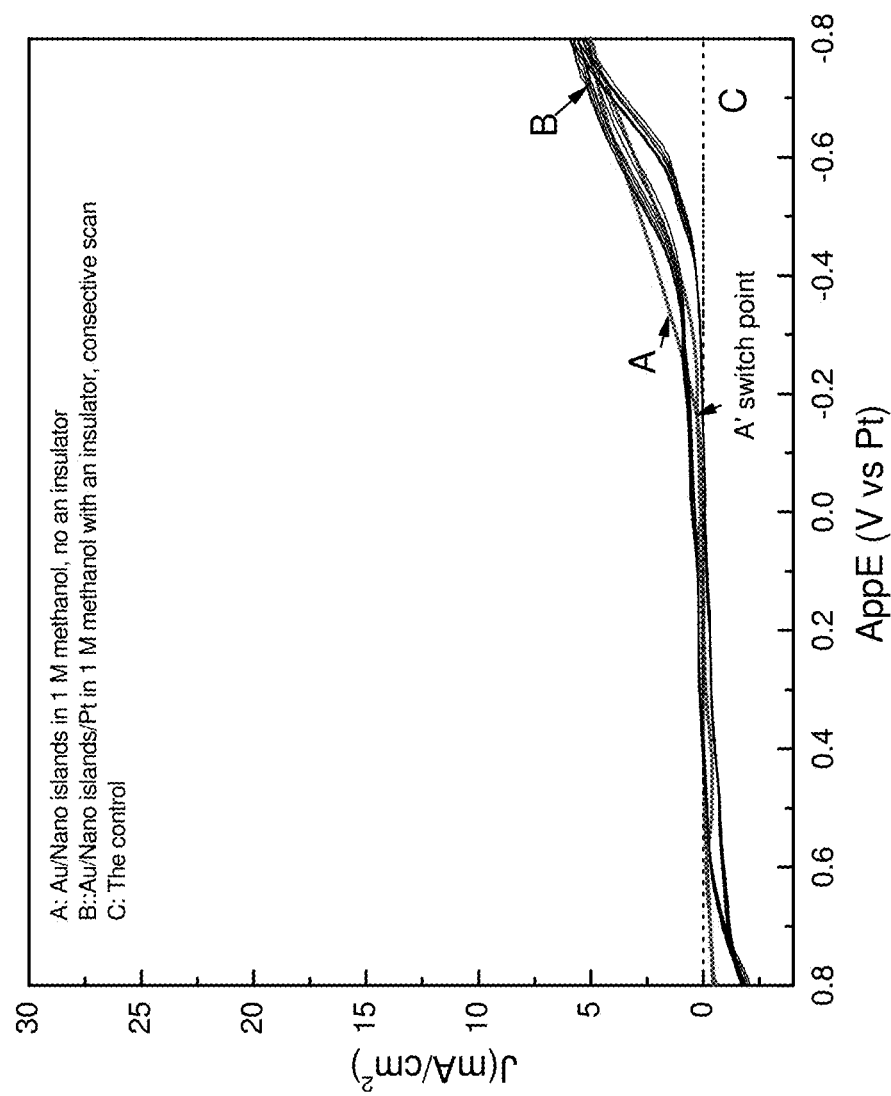
FIG. 10 depicts the half cell of Au/nano-island/Pt MEA with an insulator (black) as "A" for consecutive scans, and the half cell without an insulator (red) as B in 1M methanol, scan rate 20 mV/s at room temperature.

The normal ACHE neuronal BHE Device 1's hysteresis i-V profiles measured by the cyclic voltammetry (CV) method are presented in FIG. 8, the Au/mutated ACHE gorge with "vertical bridge/nanopore" MEA-insulator/Pt half cell's peak increased dramatically over curves "a" to curve "j" as the total scan time increased over the 10 cycles and the DET peak and the switch point (SP) are signed for the first 2 cycles as shown in FIG. 9. In contrast, when o-NPA is present, the current reduced to zero from curve aa01 to aa03 shown in FIG. 8, that indicates o-NPA played a role in the event. The i-V curves were switched and the DET peaks were observed. In FIG. 10 the red line shows the typical memcapacitor i-V curve with a switch point near −0.2V, and the half cell of Au/nano island-insulator/Pt has a quarter of the peak intensity compared with that in FIG. 8. The memristor's switch point was observed in the red line without an insulator. The exponential increase of the current in FIG. 11 may be caused by an abnormal electric field disturbing (17). The prefect hysteresis loops in the presence o-NPA and ACH using memristor #2 was observed in our report [21].

Data Acquisitions were conducted by connecting the memristor chips with an electrochemical station (Epsilon, BASi, IN) with the BASi software package in the computer. The center circle gold electrode as the working electrode with the Biomimetic membrane attached immersed in the cell culture solution in a vial connected to the anode and a pure Pt electrode without a membrane at one end was connected to the cathode and another end was immersed in the same quiet cell culture solution vial, and the Ag/AgCl reference electrode was immersed in the cell culture solution. Data was collected at a fixed scan rate under an applied electrochemical potential.

Example—6 Circular Current (CC)

Circular current was identified through a continuous scan of each of the half memcapacitor cells for multiple cycles using CV method at a fixed scan rate. From the CV profiles results constructed a 3D contour mapping between the location of Direct Electron Transfer peaks (Z), switch point location (X) and peak current (Y).

Figure 11:
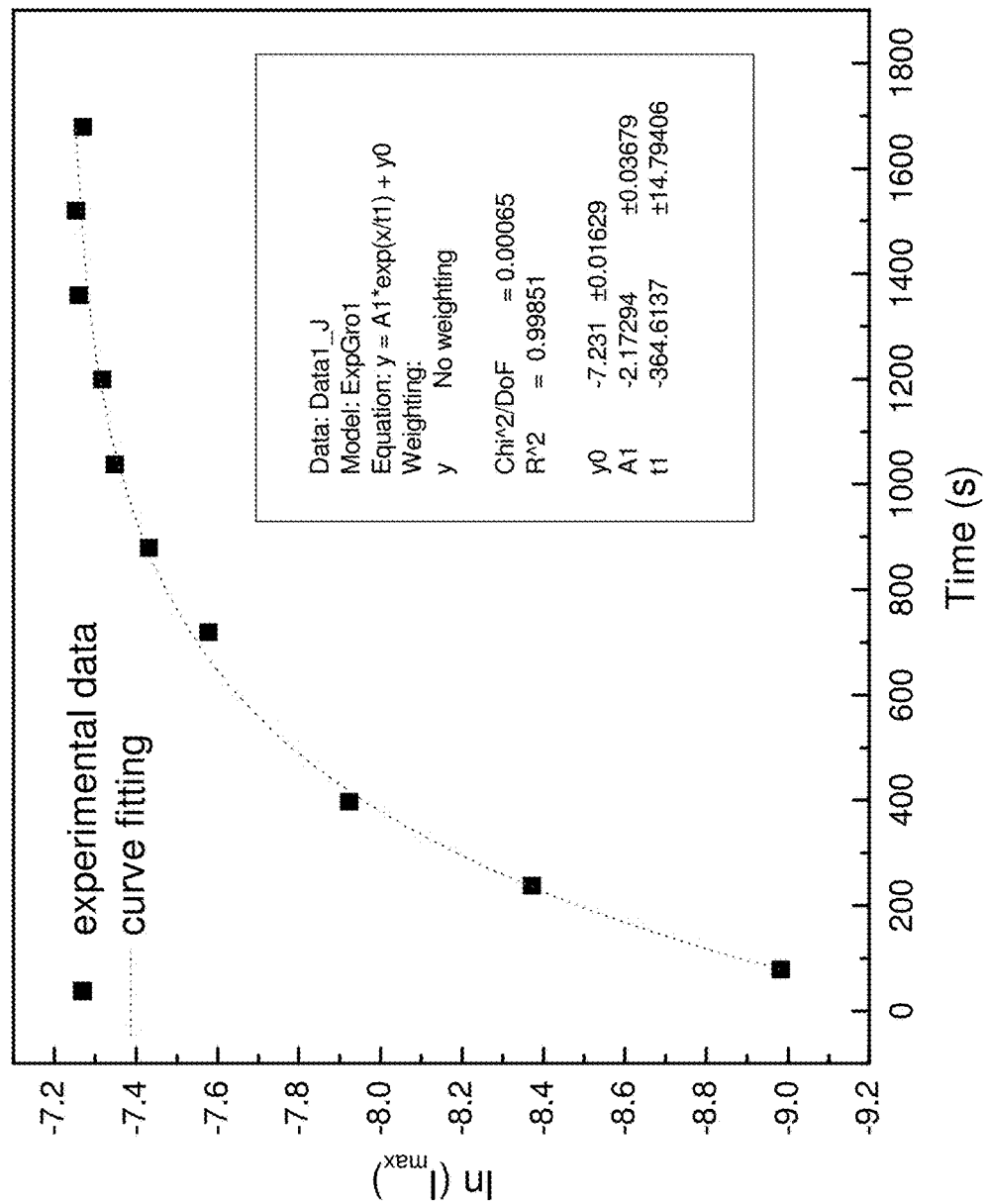
FIG. 11 depicts the plot of current vs. time of the 10 cycle scans as shown in FIG. 9 (curve A to J) of the half cell of Au/"vertical bridge/nanpore" memcapacitor in 1M methanol. The squires are the experimental data and the dotted curve is the fitted data.
Figure 12:
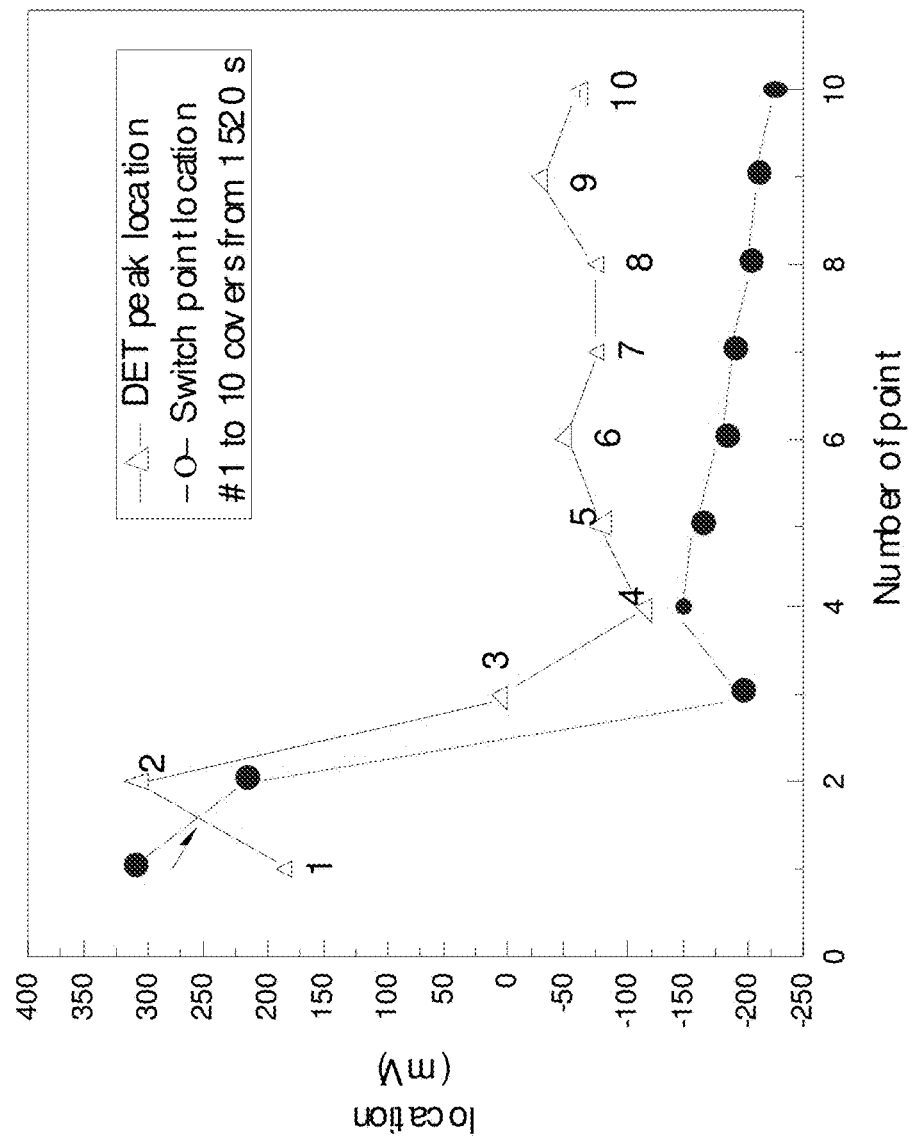
FIG. 12 illustrates the plot of DET peak location and the hysteresis switch point location vs. number of cycles. The triangle represents the DET peak and the circles represent the switch point. The number #1 to #10 represent the time sequence from the first scan to the last scan.
Figure 13:
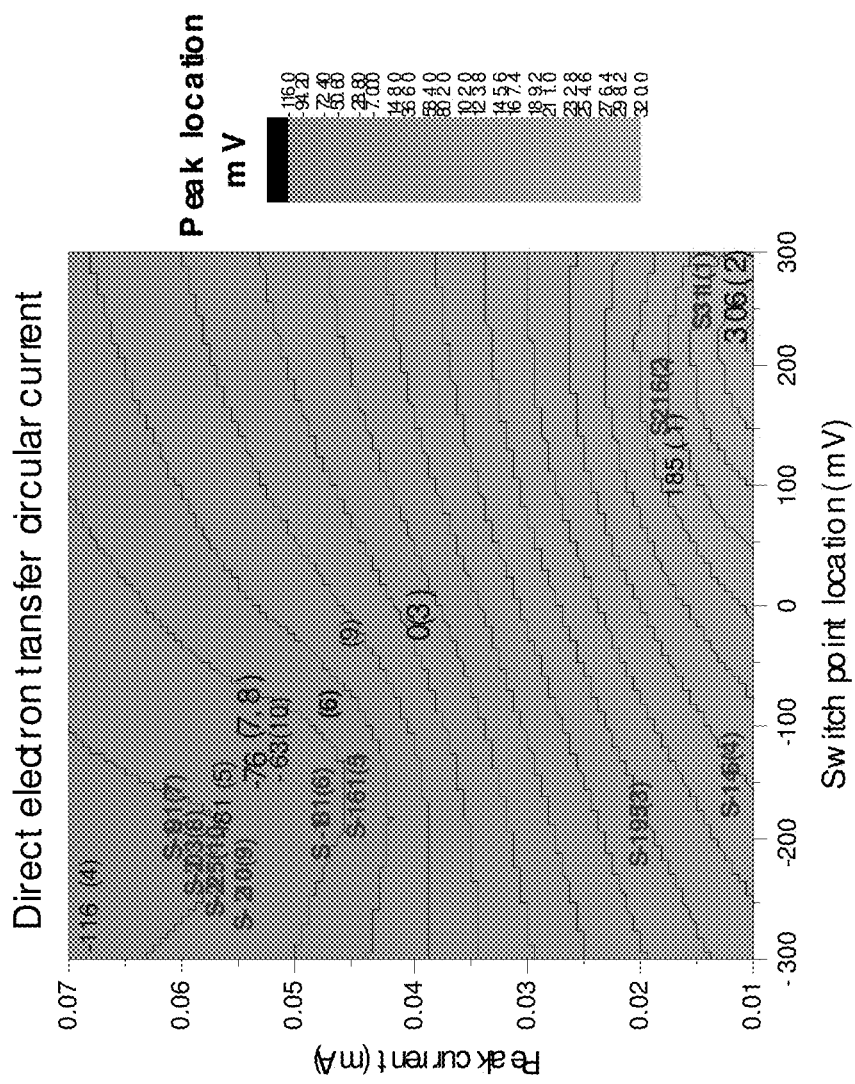
FIG. 13 depicts the contour map between switch point location (X), DET peak current (Y) and the DET peak location (Z).

The exponential increase of the current in FIG. 11 indicates its Schottky diode behavior, i.e., a small potential drop at 0.1V from the origin and then increased nonlinearly that provides higher switching speed and system efficiency [27]. In contrast, CV curves from aa01 to aa03 are flat lines after added 0.02 M o-NPA. The larger peak from "a" to "j" was signed as the diode peak, i.e., here in this invention, refers to the MEM peak, and the peak located near 0.175V was signed as the direct electron transfer (DET) peak in FIG. 9. The observations of CC was shown in FIG. 12 through the plot of current vs. cycle numbers of DET peak and Switch point, respectively. Delocalized electron relay through the multiple residue groups, hydrogen bounding and hydrophobic π-π staking could be the driving force [21]. The heterogeneous surface controlled electron transfer process in terms of DET constant Ks was calculated according to E. Laviron's method at 107/s, and the diode peak is 192.5/s, and it may reach 220.2/s from the vector contributions from our calculation [28-30]. FIG. 13 depicts a 4-demention dynamic contour map of DET peak current as X vs. switch point location as Y and related to DET peak location as Z moving along from first scan cycle data point "1" to last $10^{th}$ cycle data point, the red color associated with the switch point, the blue color associated with the DET, as the fourth dimension W. The map clearly demonstrates a disturbance of the CC momentum appearing at the left side corner of the map with both the DET negative electric field location and the switch point location move toward more negative electric potential field associated with higher positive DET peak current, that occupied 70% data (red and blue) against 30% data at which in the switch point at the positive electric potential location, that indicates an eternal power source is pushing the switch point and the DET peak moving uncontrollably until it reached the s-s. It was worthy to mention that only one DET peak associated with the third scan cycle with a switch point at origin, zero mV. The significant 95% all data points are far away from the origin, they were not alignment with origin at the predator memcapacitor, it makes the significant difference from the BHE memcapacitor.

Example—7 Electromagnetic Field Induced by CC

Figure 14A:
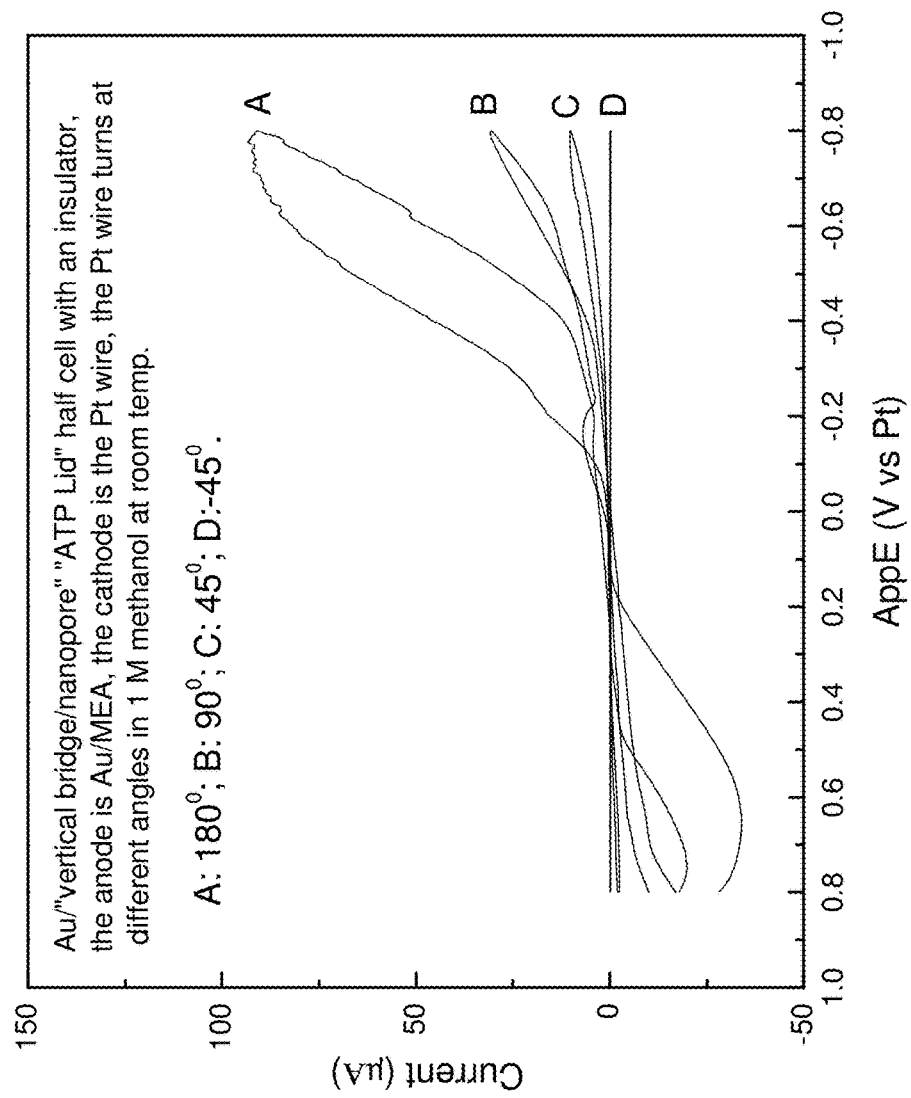
FIG. 14A depicts the AU/"vertical bridge/nanopore" "Predator" memcapacitor i-V profile during horizontally terning the connect angle over 45-180° in 1 M methanol at 20 mV/s scan rate.
Figure 15:
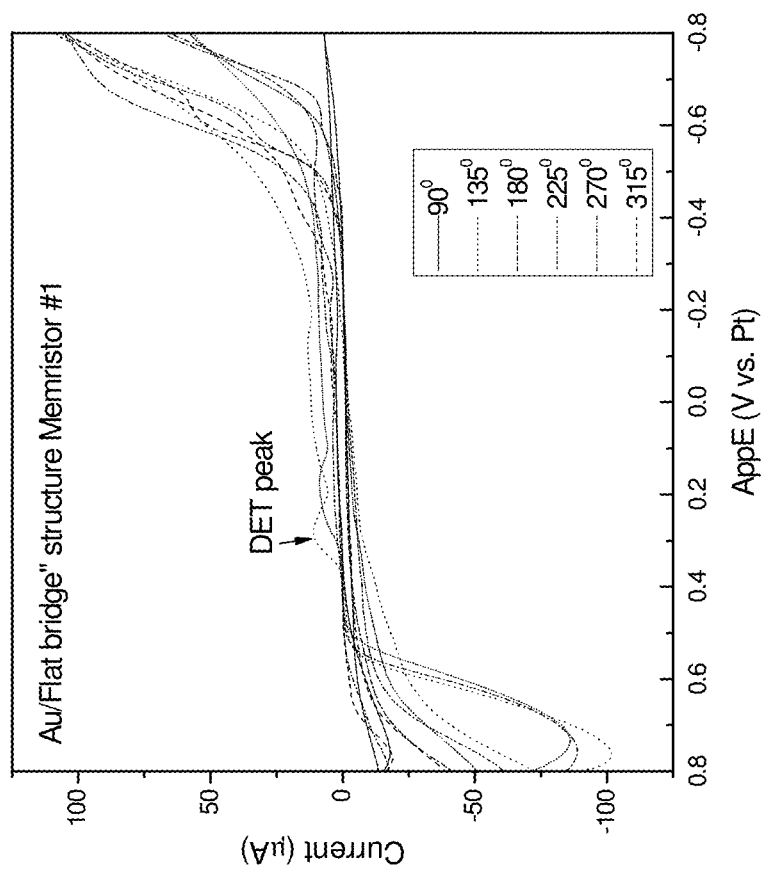
FIG. 15 depicts the i-V curves of AU/normal ACHE gorge with flat bridge/nanopore membrane/insulator/Pt memcapacitor 1 with the hysteresis profiles at different turning angles from 90 to 315° in 1 M methanol.

Evaluation of electromagnetic field induced by CC was conducted by changing the connect angles between the anode separated by an insulator and the cathode (Pt) within the AU/MEA of mutated ACHE vertical bridge/Nanopore cell from 45, 90, 180, 225, 270 to 315° clockwise horizontally in 1 M methanol at room temperature using a CV method at 20 mV/s compared with a AU/MEA of normal ACHE gorge with flat bridge/nanopore membrane as anode separated by an insulator and connected with Pt as cathode as shown in FIG. 14 and FIG. 15 respectively. A modified Biot-Savert equation was used to calculate the overall magnetic field strength at each of the 6 angle changes.

Changing the connect angles between the anode and cathode within the AU/MEA of mutated ACHE gorge with vertical bridge/nanopore from 45, 90, 180, 225, 270 to 315°, induced changes of current reflected in CV curves as shown in FIG. 14A and FIG. 14B that confirmed CC's induction. The largest current is at 225° of 435 µA compared with other angles were much smaller. The total magnitude of magnetic field can be calculated by using the Biot-Savart law [18]:

$$\vec{B} = \vec{B}_{inner} + \vec{B}_{outer} = \frac{\mu_0 I \theta}{4\pi}\left(\frac{1}{a} - \frac{1}{b}\right)\text{(into page)}$$

Consider the current charging loop formed from radial lines and segments of circles whose centers are at point P, a is the inner radius, b is the out radius of the arc. θ is the angle of the current carrying arc. $\mu_0$ is the permeability of free space, and I is current pass the arc. The induced magnetic field values are 0.00736, 0.0465, 0.2852, 1.683, 0.4644 and 0.0514 Tesla, at angles of 45, 90, 180, 225, 270 and 315°, respectively. The overall magnetic field strength induced by switch angels and by circular current can be calculated according to a modified equation:

$$B_{total} = B_c + B_{arc} = \mu_0 NI(2\pi r)^{-1} + B_{arc}$$

The Biot-Savert law, and $B_c$ were defined by Ampere's law. Herein, the highest total value of magnetic field induced is 3.53 Tasla at 225°. The highest total value of magnetic field induced is at 225°. As shown in FIG. 14B, the quick raised current is at the quantum Fermi Resonance point [18] at 225°. This is the first reported instance of an electromagnetic field induced by non ferromagnetic materials. Using NIST's SRM965A human sera at glucose level 2 followed the same procedures applied onto this device, we confirmed the finding. For comparison, FIG. 15 does not have a Fermi Resonance point observed.

Example—8 Embedding a Low-to-High Frequency Switch for Energy Saving

SC behavior was studied using whole memcapacitor cell for the two models at frequencies of 25 and 1000 Hz compared at room temperature. Ratio of action potential at 1 kHz vs. at that of 25 Hz at the head and at the tail was compared for the power saving advantage of SC behavior compared with the two models.

Figure 16:
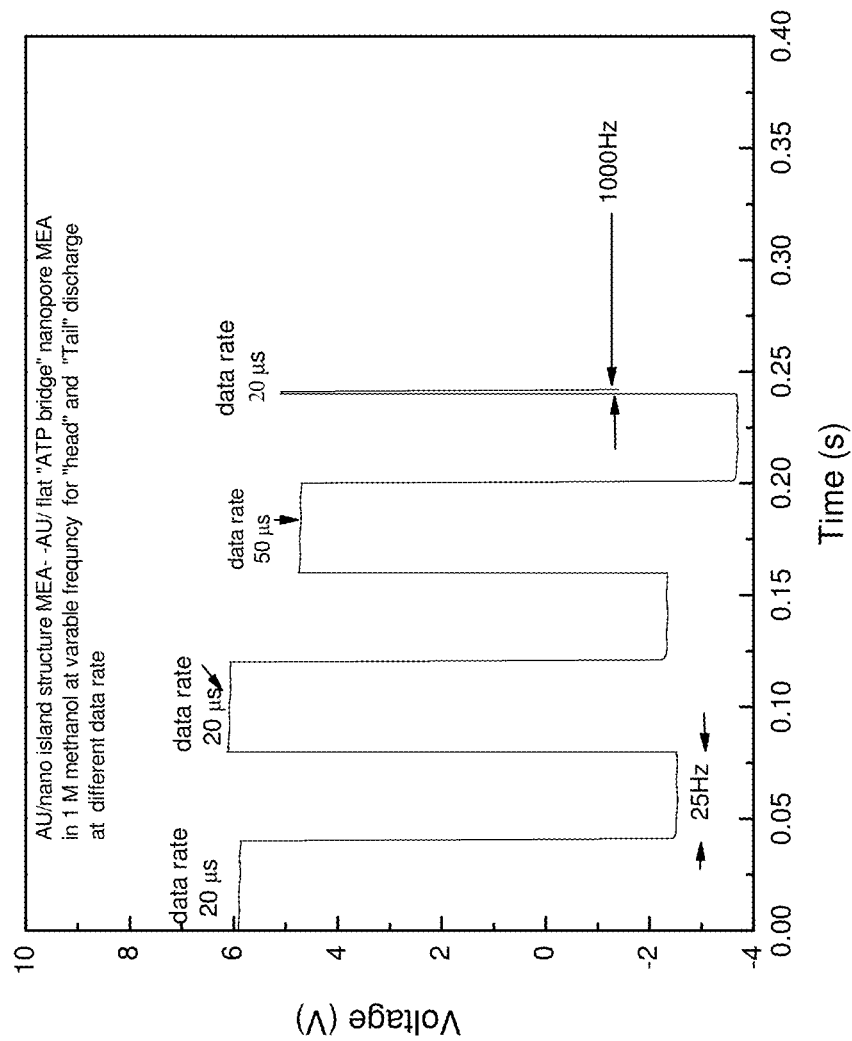
FIG. 16 depicts the "Healthy BHE fish" memcapacitor discharges at diverging frequency over 25 Hz-1 KHz in 1 M methanol at room temperature.
Figure 17:
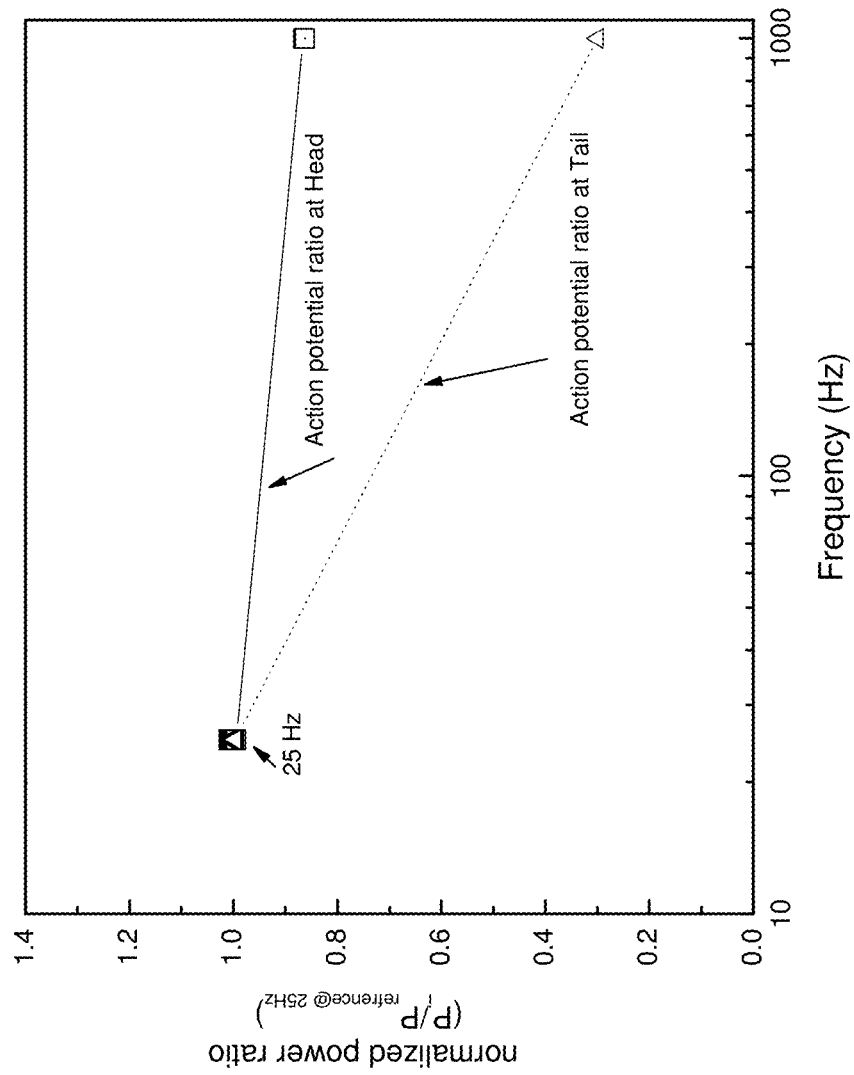
FIG. 17 depicts the BHE device in FIG. 16 has an energy saving from 16% up to 33% for discharge ratio at head and tail at 1 KHz compared with the discharge ratio at 25 Hz, respectively.

BHE fish's flexibility of signal-cloaking jumping from low to high frequency was mimicked by our Biomimetic BHE fish as shown in FIG. 16 from 25 Hz to 1000 Hz, and the energy saving at high frequency was demonstrated in FIG. 17 by 16-33% compared at 25 Hz at head and tail discharge, respectively.

Example—9 Characterizations of Memcapacitor

A total charge of a memcapacitor is a function of a state dependent of capacitance and the potential across it, where q(t) is the total charge on the capacitor, and V(t) is the potential across it. A capacitance C({x}, t) which is state dependent [31].

$$q(t) = C(\{x\}, V, t)V(t)$$

Figure 5:
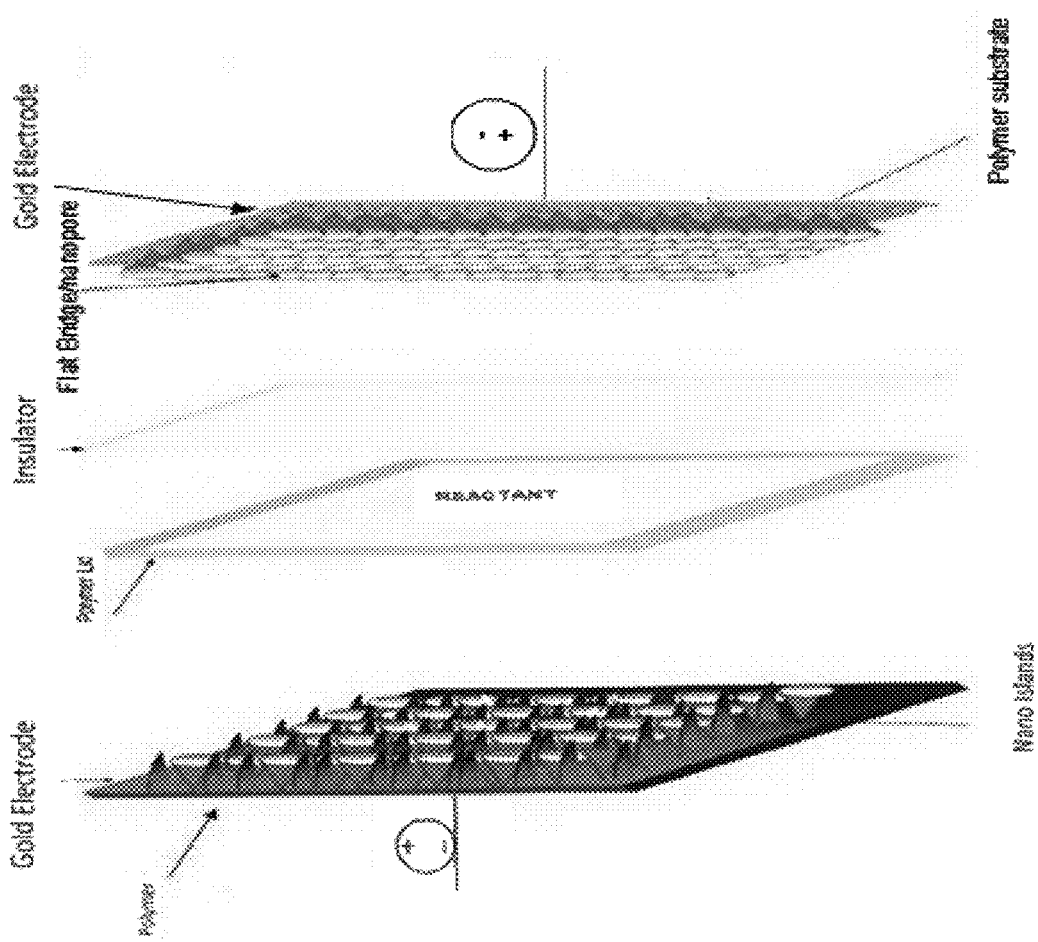
FIG. 5 illustrates the Memcapacitor 1 model as a neuron network of "BHE".

The memcapacitors' charge/discharge energy profiles data acquisitions were conducted by connecting the memcapacitor chips at the two ends separated by a mobile dopant barrier dielectric material. One side of the membrane has structure formed flat horizontal nano-bridges with array larger vertical nanopores underneath the bridge; and another side of the MEA comprising of an electrode/membrane has a negative mobile dopant polymer network forming arrays nano-islands with the membrane thickness is one third of the opposite MEA in order to be feasible conducting "head-tail" biphase discharge at wide range of frequencies as seen in FIG. 5, after that then the cable was connected to an electrochemical station (Epsilon, BASi, IN) with the BASi software package in the computer. The double step chronopotentiometry (DSCPO) method was used to measure the voltage change upon applied a current under ±30 mA with data rate 2 µs at 1 kHz were chosen under the room temperature. The predator memcapacitor device with the same AU/normal ACHE forge with flat horizontal nano-bridges with array larger vertical nanopores underneath the bridge MEA at one end separated by an insulator, but another end MEA was configured with AU/mutated ACHE gorge with vertical array bridge-flat bridge associated with array nanopores connected instead of the nano-island membrane under the same experimental conditions. The real time data was acquainted using the Origin 9.0 software.

Figure 18:
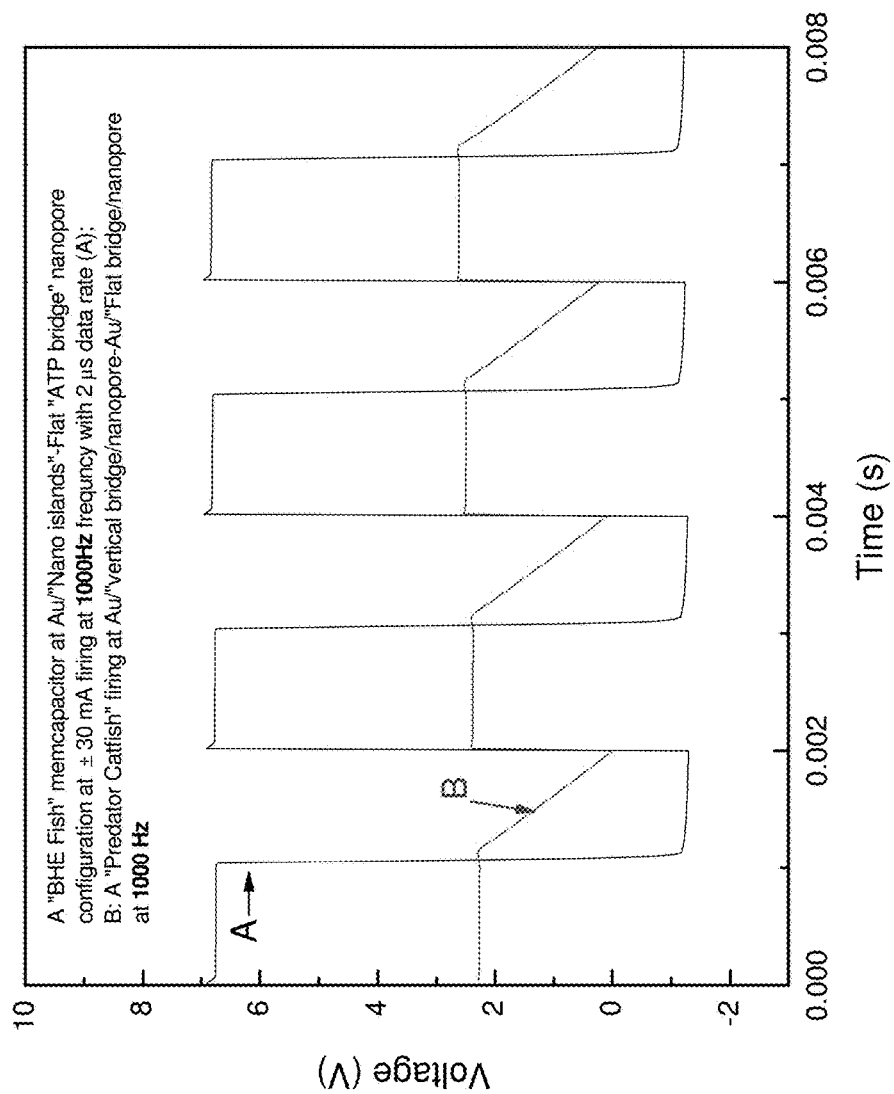
FIG. 18 illustrates the "Predator catfish" discharges at 1 KHz with monophase firing (red) with ±30 mA; but the "BHE fish" can use head-tail biphase firing (black) at 1 KHz under same condition.

FIG. 18 depicts the "Predator catfish" discharges at 1 KHz with monophase firing but the "BHE fish" can use head-tail biphase firing at 1 KHz at ±30 mA.

Figure 19:
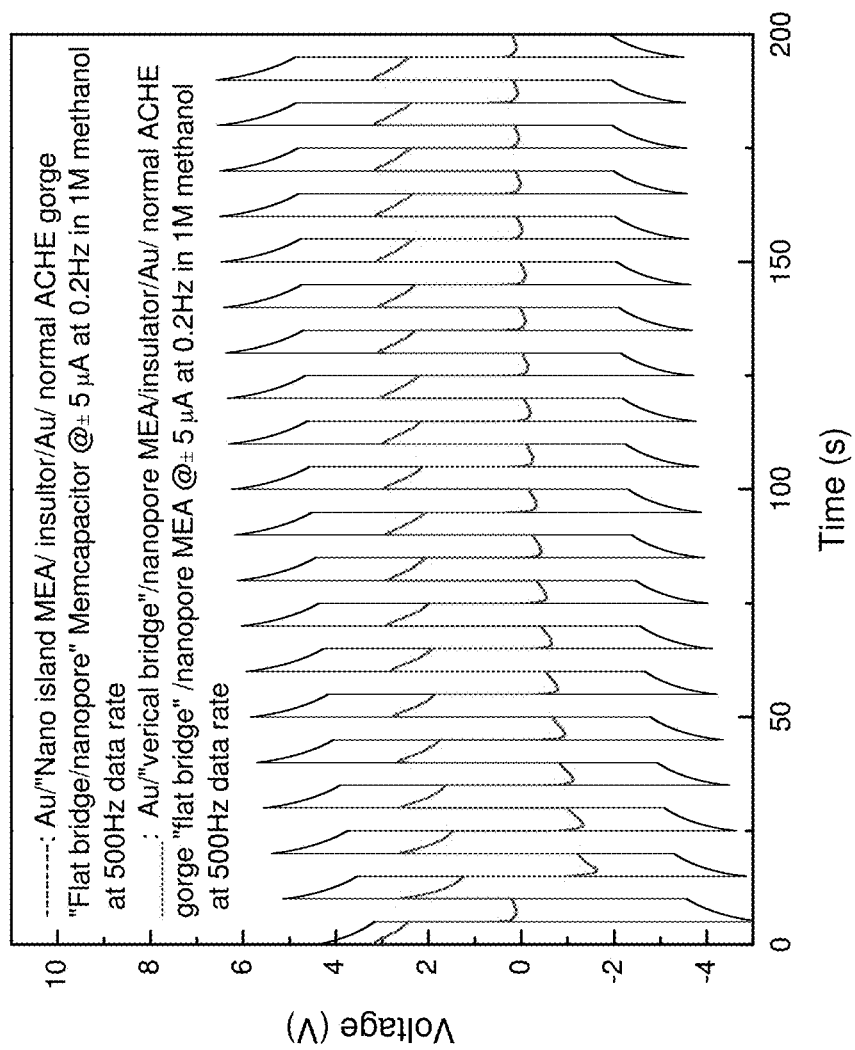
FIG. 19 depicts the comparison of discharge/charge profiles between "BHE" fish (black) and "Predator" fish (red) at Delta SWS (0.2 Hz) in 1M methanol at ±5 µA.

The whole cell synapse profiles during "Slow-Wave-Sleeping" (SWS) at 0.2 Hz at ±5 µA were studied at room temperature in 1 M methanol. The electric synapse profiles between the two memcipacitors were presented in FIG. 19. It is evidenced that the BHE fish has a great declarative memory consolidation with the highest biphase wave intensity than the predator at night.

Example—10 Assessing Stability and Efficiency

Figure 20:
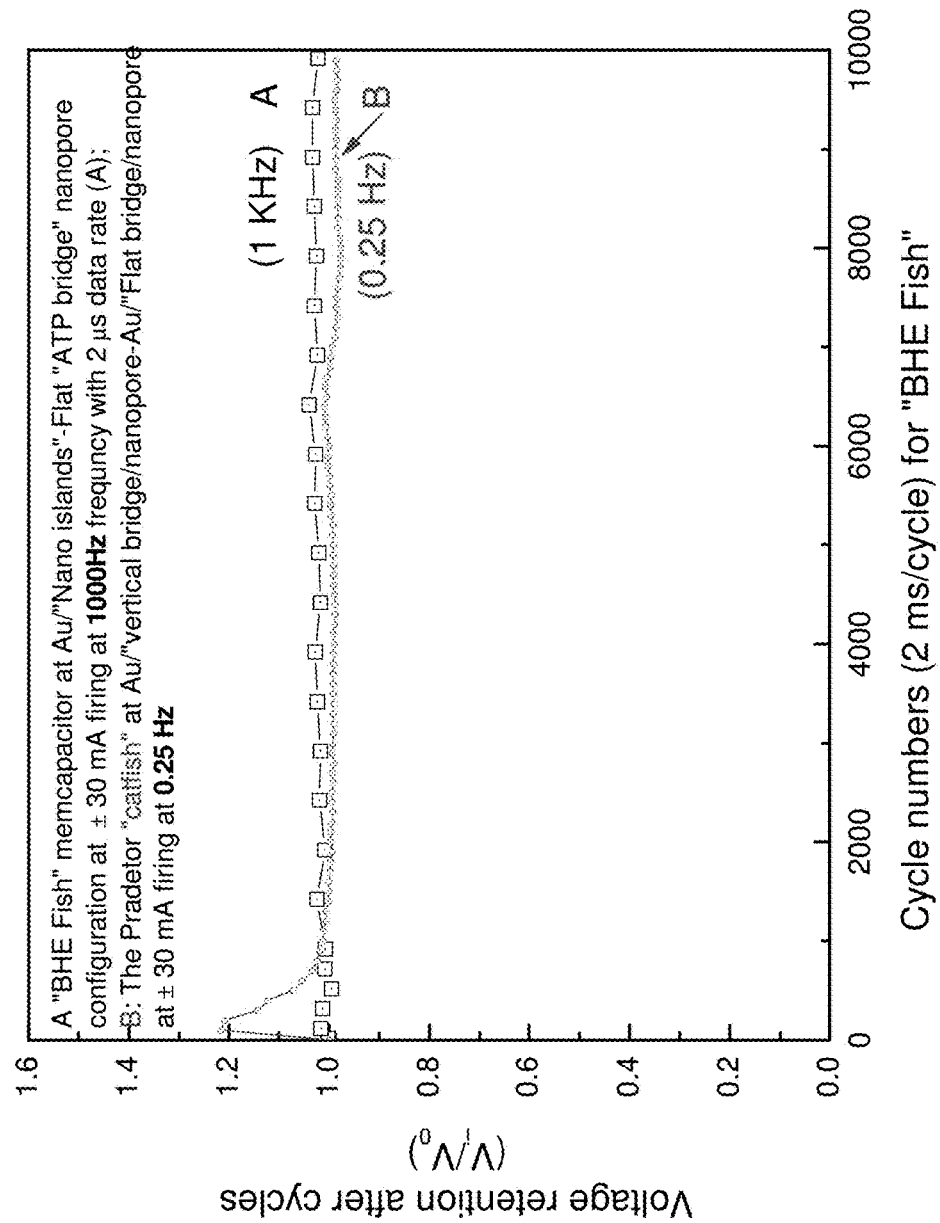
FIG. 20 illustrates the efficiency of the discharge/charge cycle by comparing between the "BHE fish" (black curve) and the "Predator fish" (red curve) over 9999 cycles at ±30 mA at 1 KHz for BHE, 0.25 Hz for the predator fish.

The Double Step Chronopotentiometry (DSCPO) method was used for assessing utility of the newly developed memcapacitors in assessing stability and efficiency of the 9,999 discharge/charge cycles in 1M methanol at ±30 mA using the best performing frequency of 1 KHz for BHE, and best frequency of 0.25 Hz for the predator as shown in FIG. 20. In FIG. 20, the curve A referred to the "BHE fish", it illustrates the stability and efficiency of model 1 memcapacitor for 9,999 cycles firing with 2 ms/cycle at ±30 mA at 1 KHz. It reached an average 100.0±0.01% efficiency against the original starting point (as 100.0) compared with curve B of 98%, except starting several cycles are above 100%. Curve B refers to "predator" had 4s/cycle at ±30 mA at 0.25 Hz.

Figure 21:
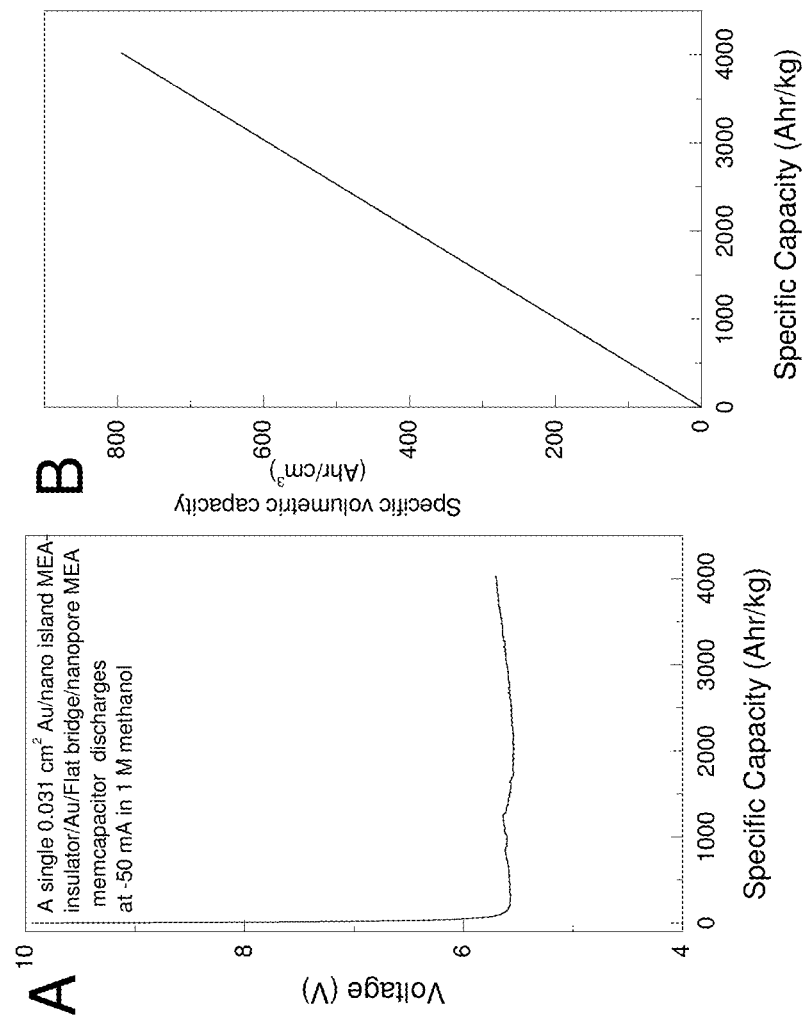
FIG. 21 depicts the memcapacitor model 1 as the "BHE" fish, its discharge profiles of voltage vs. specific capacity at −50 mA in 1 M methanol (A) and the plot of specific volumetric capacity vs. specific capacity of mass (B).

FIG. 21A and FIG. 21B demonstrates the BHE memristor/memcapacitor has capability to effectively discharge energy at −50 mA and store energy, respectively. The specific capacity is up to 4000 Ahr/kg, and the specific volumetric capacity up to 800 Ahr/cm$^3$ for memcapacitor 1. Memcapacitor 1 has current density of 1.6 A/cm$^2$ due to the asymmetric engineering design and the flat bridge/nanopore structured membrane.

Figure 22:
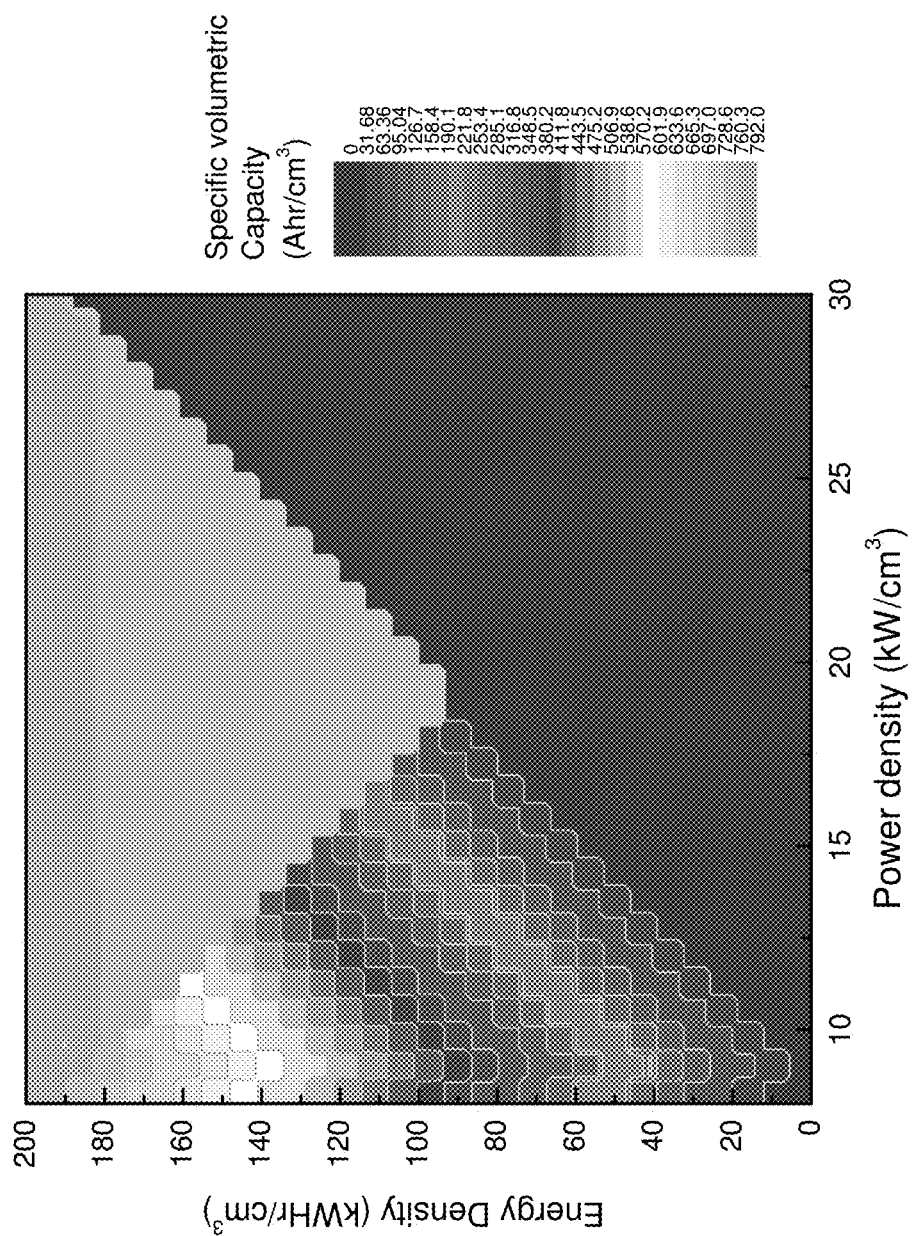
FIG. 22 depicts the contour map of BHE memristor/memcapacitor specific energy density as Y axis vs. Power density as X axis and specific volumetric capacity as Z.

FIG. 22 depicts the contour map between the BHE memristor/memcapacitor energy density vs. power density and the specific volumetric capacity. It demonstrated the highest power density 30 kW/cm$^3$ associated at 200 KWhr/cm$^3$ with 792 Ahr/cm$^3$.

The Biomimetic "BHE fish" avoidance of the "predator" by signal-cloaking was demonstrated.

REFERENCES

1. Stoddard P K and Markham M R, *Signal cloaking by electric fish, Bioscience*, 58(5), 415-425, 2008.
2. Stoddard P K, *Predation enhances complexity in the evolution of electric fish signals*, Nature 400, 254-256, 1999.
3. Herberholz J and Marquart G D, *Decision Making and Behavioral Choice during Predator Avoidance*, Neurosci. 6, 125, 2012.
4. Sussman J L, Harel M, Frolow F, Oefner C, Goldman A, Toker L, Silman I, Science 253, 872-879, 1991;

5. Whyte K A. Greenfield S A. Exp Neurol 184, 496-509. 2003.
6. Chen E T, Ngatchou C, *An electron-relay prototype supercapacitor mimics electrophorus electricus's reversible membrane potential for a high rate discharge pulse*, Sensors and Transducers J. 15, special. 42-48, 2012.
7. Chen E T, Ngatchou C, *An electron-relay prototype supercapacitor mimics electrophorus electricus's reversible membrane potential for multiple-organ discharge*, Clean Tech, 202-205, 2012.
8. Thornton J T, Christelle C, Chen E T, *Flexible and turnable biomimetic pyruvate dehydrogenase complex (PDC) supercapacitors*, Cleantech, 356-359, 2013.
9. Martinez-Rincon J and Pershin Y V, *Bistable non-volatile elastic membrane memcapacitor exhibiting chaotic behavior*, Electron Devices, IEEE Transactions 58 (6), 1809-1812, 2011.
10. Martinez-Rincon J, Ventra M D, Pershin Y V, *Solid-State memcapacitive system with negative and diverging capacitance*, Physical Review B, 81(19), 195430-1-195430-7, 2010.
11. Pickett M D, Medeiros-Ribeiro G and Williams R S, *A scalable neuristor built with Mott memristors*, Nature Materials, DOI: 10.1038/NMAT3510, 2012.
12. Kozma, Pino R E, Pazienza G E, *Advances in neuomorphic memristor science and applications*, Springer publisher, 2012.
13. Ventra M D, Pershin Y V, *On the physical properties of memristive, memcapacitive, and meminductive systems*, Nanotechnology 24, 255201, 2013.
14. Ohno T, Hasegawa T, Tsuruoka T, Terabe K, Gimzewski J K, *Short-term plasticity and long-term potentiation mimicked in single inorganic synapses*, Nature Materials, 10, 591-595, 2011
15. Yang J J, Strukov D B, Stewart D R, *Memristive devices for computing*, Nature Nanotechnology 240, 2012. DOI: 10.1038.
16. http:en.wikipedia.org, Negative resistance.
17. Martinez-Rincon J, Ventra M D, Pershin Y V, *Solid-State memcapacitive system with negative and diverging capacitance*, Physical Review B, 81(19), 195430-1-195430-7, 2010.
18. Rai D, Hod O and Nitzan A, J. Physical Chemistry Letters, 2, 2118, 2011.
19. Islas R, Heine T and Merino G, Accounts of Chemical Research, 45(2), 215, 2012.
20. Chen E T, Nanopore structured electrochemical biosensor, U.S. Pat. No. 8,083,926, Dec. 27, 2011.
21. Chen E T, Thornton J, Ngatchou C, Duh S H, *Nanostructured memristor sensor mimics acetylcholinesterase (ACHE) active sites in the gorge for fM detection of acetylcholine*, NSTi-Nanotech 2014, 2, 200-203.
22. J. Martinez-Rincon and YV Pershin, Bistable nonvolatile elastic-membrane memcapacitor exhibiting a chaotic behavior, *Electron Devices, IEEE Transactions* 2011, 58 (6), 1809-1812.
23. J. Martinez-Rincon, M D Ventra, Y V Pershin, Solid-state memcapacitive system with negative and diverging capacitance, *Physical Review B*, 2010, 81(19), 195430-195437.
24. M D Pickett, G. Medeiros-Ribeiro and R S Williams, A scalable neuristor built with Mott memristors, *Nature Materials*, 2013, 12, 114-117.
25. M. Suri and B. Desolvo, Advances in neuomorphic memristor science and applications, Editors R. Kozma, R E Pino, G E Pazienza, *Springer publisher*, 4, 2012.
26. M D Ventra, Y V Pershin, On the physical properties of memristive, memcapacitive, and meminductive systems, *Nanotechnology* 2013, 24, 255201.
27. Idea Diode, http:en.wikipedia.org
28. E. Laviron, J. Electroanal Chem., 101, 19-28, 1979.
29. E. T. Chen, J. Thornton, C. Ngatchou, S-H. Duh, P. T. Kissinger, NSTi-Nanotech (3), 115-118, 2013.
30. Chen E T, *first volume, Third Edition*, Lyshevski S E Dekker Encyclopedia of Nanoscience and Nanotechnology, *CRC*, Mar. 20, 2014.
31. Ventra M D and Pershin Y V, *On the physical properties of memristive and memcapacitive and meminductive systems*, J of Physics D, arXiv:1302.7063v2, 2013.

Followings are the Specifications in CIP Application

DETAILED DESCRIPTION OF THE INVENTION

Example 1—Fabrication of the Nanostructured Biomimetic Self-Assembling Membranes (SAM)

The nanostructured biomimetic ACHE SAM with the vertical bridged conformational "Mutated ACHE Gorge" was freshly prepared. Polyethylene glycol diglycidyl ether (PEG), triacetyl-β-cyclodextrin (T-CD), poly(4-vinylpyridine) (PVP) were purchased from Sigma. PVP was purified before use. The mono derivative dimethyl β-cyclodextrin named as (mM-β-DMCD) was generally synthesized according to the published procedures [19]. The appropriate amount of solutions of individual polymer and reagents were prepared [20]. The mixture solution was made up by mM-β-DMCD (2 g/L to 2.5 g/L, T-CD 2-3 mM, PEG 2 g/L-3 g/L and PVP (40 mg/dL-80 mg/dL), the mixture was incubated in 37 C for 2-3 hrs, then added 0.02M o-NPA with the molar ratio to TCD in the range of (500-1000):1 to the mixture for the device having a flat membrane with nanopores. The Au electrode has 50 nm thicknesses and 3 mm in diameter. The mixture solution was injected onto the surface of the electrode and was incubated for 48 hrs at incubation [20]. After that, the further clean and incubating procedures were followed by literature 20-22.

The nanostructured biomimetic "Normal ACHE Gorge" neuronal network SAM with the flat bridged conformation, naopores and lattices was freshly prepared by adding appropriate amount of o-nitrophenyl acetate (o-NPA) into the above described mixture solution for construction of the cross bar toroidal matrix ACHE SAM. All other procedures were followed by literature 20-22. Adjusting the concentration of o-NPA leads to the air gaps thinner or thicker between the flat bridge bars and the vertical cross bars was suggested.

Example 2—AFM Measurements

The morphology of the cyclodextrin (CD) derivatives SAMs were characterized by using an instrument (model Multimode 8 ScanAsyst, Bruker, Pa.). Data collected in PeakForce Tapping Mode. Probes used were ScanAsyst-air probes (Bruker, Pa.). The silicon tips on silicon nitride cantilevers have 2-5 nm radius. The nominal spring constant 0.4 N/m was used. NanoScope Analysis v1.40r2 software was used. FIG. 23 illustrates the 3D memcapacitor blocks serve as the dual sensor, where sits on a 50 nm pure gold substrate plate attached onto a flexible plastic plate. The model consists of green balls and sticks in the top and bottom layer covered with conductive cross-linked polymers; the oranges represent the inner "ACHE Gorge" neuronal axons in narrow cylinders connected through the neuronal terminals and dendrites as truncated donuts in a compact flat metrics by forming toroidal matrix. The SAM fabricated by added o-NPA in the mixture of mM-β-DMCD, T-CD, PEG and PVP, that formed a flat bridge with nanopores. FIG. 24A shows the flat bridge with width 330 nm and length in 1.4 µm by cross section analysis with RMS 0.6 nm in the image. Nanopores can be seen on each side of the bridge; the pores on the left side of the bridge have a depth 0.3-0.8 nm and diameter 20-30 nm. FIG. 24B is the AFM image with the body of the horizontal flat bridge densely covered with thousands uniformly and orderly orientated donuts shaped "fish scales", density of $10^7$ pores/cm$^2$, with the average donuts size of 22 nm in diameter and the pores in the center are 9-10 nm in diameter. The AFM image in FIG. 24B shows the membrane thickness is about 35.5 nm and the membrane roughness is 12.5 nm.

Example 3—Mimicking the Active ACHE Gorge and its Linen

A "Normal Active Site ACHE Gorge" was defined as a linen-cylinder consists of a bipolar dome with two poles. (1): the positive isopotential pole: esteratic site of five residues containing the catalytic triad (Ser-200, Glu-327, His-440), acyl pocket Phe 288 and Phe-290 [23-26], that was mimicked by polyethylene glycol diglycidyl ether (PEG) (for Ser 200) . . . imidazolyl-dimethyl-β-cyclodextrin (M-CD) (for His 440) . . . triacetyl-β-cyclodextrin (T-CD) (for Glu327). Phe288 and 290 were mimicked by o-NPA. (2) The 14 aromatic residues for gorge lining were mimicked by excess amount of o-NPA (1:500-1000 of T-CD/o-nithophenyl acetate (o-NPA)) and W84 were mimicked by poly(4-vinylpyridine) (PVP). (3) the negative isopotential pole: the Asp-72, Tyr-121, Tyr-70, Tyr-354, and Trp-279 are the residues of the peripheral and were mimicked by TCD . . . PEG polymer and TCD . . . PVP polymers as anionic site (PAS), F330, Y121 were mimicked by o-NPA, and Trp279 was mimicked by PVP. FIG. 25 depicts the biomimetic ACHE gorge of a "normal neuronal cell" prosthesis on the left. On the right hand side is an illustration of the cross bar layout and it led to form the toroidal matrix.

Example 4—Engineering the Organic Memristor/Memcapacitor Device as the "Normal ACHE Gorge" Neuronal Network Device The "Normal ACHE Gorge" Neuronal Network Device (NND) was built by arrays of 3D cross bars by self-assembling technology with the above section mentioned membrane in FIG. 25. The FIG. 25 on the right-hand side is the illustration of the 3D cross bar, the vertical green bar presented here was made by the architecture of a vertical double-layer cylinder with an inner core cylinder consists of a chain of cyclodextrin chunked "donuts" shape, hollow in the center, as pendants and the nanometer air gap serves as the dielectric substance was located between the two electron-relay circuits and the PEG as the necklace chain passes through; the basement bar was made of the gold; The horizontal bar was made by the o-NPA formed hydrogen bounding or hydrophobic interaction with the TCD . . . PEG//TCD . . . PVP wrapped around the flat bridge structure. This is a partial illustration of the cross bar essential block, as shown the coil wrapped in a toroid. On the surface of the pure gold plate, the toroidal matrix conductive membrane was self-assembled through the imidazolyl derived mono-substitute 13-dimethylcyclodextrin (m-β-DMCD, in short, MCD) cross-linked with PEG, PVP and TCD with positive and negative electron-relay circular current flow inside the cavity; the nano air gap between two chucked CD "donuts-like" cavity; and the o-NPA formed ACHE gorge linen with other residue groups through hydrogen bonding wrapped around the cross bars with the TCD . . . PEG// TCD . . . PVP polymers; the vertical nano air gap exists between the NPA linen and the polymer TCD . . . MCD . . . PEG . . . PVP; and the horizontal cross bars are of NPA linen with polymer TCD . . . PEG//TCD . . . PVP. The air gap between the CD cavity is much smaller than the air gap between the flat NPA mash bridge and the rim of the CD cavity. Herein, this device compromises the variations air gaps reflected the essence of the flexibility and neuronal plasticity necessary.

Sample 5—Characterization of the Organic Memristor/Memcapacitor

Memristors are devices made of nanolayers that have the capability to mimic neuronal synapse with a characteristic of hysteresis loop in the i-V curve [27-32]. A memristor is a semiconductor whose resistance varies as a function of flux and charge. This allows it to "remember" what has passed through the circuit [33, 27-29]. $G(\{x\},t)$ which is state dependent $$I(t)=G(\{x\},V,t)V(t) \quad (1)$$

The memristor's hysteresis i-V profiles measured by the cyclic voltammetry (CV) method and the i-V hysteresis curve with 0.4 mM Aβ in aqueous solution was demonstrated in FIG. 26 with a switch point at the origin (0, 0) against the control at 20 Hz scan rate indicating Aβ has the power to alternating a normal neuronal circuitry to pathologically dysfunction and alternating the brain cell's reversible membrane potential. FIG. 27A in NIST SRM965A human serum without Aβ. Data Acquisitions were conducted by connecting the memristor chips with an electrochemical station (Epsilon, BASi, IN) with the BASi software package in the computer. The gold chip consists of three gold leads, the center circle gold chip with the Biomimetic membrane is connected to the anode, and the pure gold electrode without a membrane is connected to the cathode electrode, and the gold electrode is connected to the reference electrode at a fixed scan rate under an applied electrochemical potential, the current was recorded due to the change of a direct electron-relay (DET) either in oxidation or reduction direction. DET phenomenon is a key event in sensing and energy storage that led to our several inventions [34-38]. Literature reported electric synapse is one tenth of that of chemical synapse [39]. The frequency change affecting on the memristor/memcapacitor was depicted in FIG. 27A using NIST serum without Aβ. At low frequencies, the sensor has the highest *Direct Electron-relay Transfer* (DET) [10-12, 40] peak intensity than at high frequencies and all curves have hysteresis characters.

The intensity of the DET peak was reduced by a hundred times, and the cross-point locations were moved nonlinearly toward to negative field as frequency increased in the presence of 3.8 nM and 76 nM Aβ as shown in FIGS. 27B and 27C, respectively compared to FIG. 27A without Aβ. Various concentrations of Aβ reduced the DET peak intensity by 94-99% in SWS frequency more than at any other frequencies as shown in FIGS. 27B and 27C. This mem-device showed significant bipolar nonlinear hysteresis through the CV curves at low frequency, and linear hysteresis at high frequency.

A total charge of a memcapacitor is a function of a state dependent of capacitance and the potential across it, where q(t) is the total charge on the capacitor, and V (t) is the potential across it. A capacitance C({x}, t) which is state dependent [28].

$$q(t)=C(\{x\},V,t)V(t) \quad (1)$$

The synapse energy profiles data Acquisitions were conducted by connecting the memcapacitor chips, the gold lead with nano-biomimetic membrane was connected to the anode, the bare gold lead was connected to the cathode, so was the reference connected to the pure gold lead, then the cable was connected with an electrochemical station (Epsilon, BASi, IN) with the BASi software package in the computer. The double step chronopotentiometry (DSCPO) method was used to measure the voltage change upon applied an alternative small current under ±10 nA with data rate 0.001s at 0.25 Hz and $2\times10^{-5}$s data rate over the frequency range of 40 Hz-1 kHz were chosen under the room temperature. The time for action potential and resting potential (discharge vs. charge steps) have to be settled in a desired time frame. The real time data was acquainted under this program. In this invention, the OriginPro 9.0 software was used for data analysis and plotting figures.

Sample 6—Overcome the Sample Instability of Aβ

Instability of Aβ in various media has been reported in the literature [4-6], and our own experiments confirmed the instability in aqueous solution. The CV curves shown in FIG. 28 illustrate the peaks were instable in water evidenced by the curve's cross-point moving more than 0.55V from negative potential toward positive potential direction between 500 ng/mL Aβ and 2 μg/mL Aβ. After 0.1 mg/mL TCD presences in the media, the CV curves are stabilized over the Aβ concentration ranges from 3.8 nM, 15 nM to 380 nM and the signal intensity was inversely proportional to the concentration against the control as shown in FIG. 29. It is noticed that the cross-point disappearing over the Aβ concentration ranges in the newly presented TCD indicates TCD may play a positive role in blocking Aβ forming a twisted neuronal circuitry.

Sample 7—Quantitation of Aβ

The CA Method.

The CA method was used for quantitation of Aβ. Aβ$_{25-35}$ was purchased from Sigma. The data were acquired at room temperature under two-step fixed potentials in 8 concentration levels covering Aβ final concentrations ranging from $10^{-11}$M to $10^{-7}$M, with triplicates in DDH$_2$O with 0.1 mg/mL TCD and using an electrochemical work station (Epsilon, BASi, IN) with the companied software package. Origin 9.0 was used for all statistic data analysis and figure plotting.

FIG. 30 illustrates CA curve profiles in the presence of Aβ in aqueous solutions over the range of 0.037 to 151 nM Aβ. FIG. 31 illustrates the calibration curve with a linear regression equation Y=0.59+0.63X, r=0.998 (n=23), P<0.0001, Sy/x=1.96. The value of Detection of Limit (DOL) is $5.0\times10^{-11}$M per cm$^2$ with a pooled relative standard deviation of 0.2% related to that at the mean concentration. Because this sensor is only 0.031 cm$^2$, hence, its DOL is 1.6 pM Aβ.

The Voltage Method.

The characterization of the memcapacitor serving as a voltage sensor was conducted by the DSCPO method in ±10 nA and 0.25 Hz in DDH$_2$O with 0.1 mg/mL TCD, with spiked Aβ final concentrations from 0.038 nM to 60.8 nM, and with triplicates for a calibration curve. The NIST SRM 965A human reference serum, with controlled blood glucose 70 mg/dL, spiked with Aβ having 4 levels from 3.8 to 417 nM with a single run at the same experimental conditions as in water media, and measurements without spiking Aβ were also taken for comparison.

The magnitude of voltage change was in the highest when Aβ was not presence as shown in FIG. 32A$_1$ having the curves averaged from triplicate runs. The Aβ affects on synapse discharge voltage curves were depicted in FIG. 32A$_2$ with signal intensity inversely proportional to Aβ concentration. The volumetric energy density in the calibration curves as shown in FIG. 32B$_2$ was inversely proportional to Aβ concentrations with a linear regression curve in water (in black) equation Y=1.48−0.018X, r=−0.992, S$_{y/x}$=0.058, n=12, p<0.0001 over volumetric energy density from 0.41 to 1.50 μWHr/cm$^3$. The Detection of Limit (DOL) is $2.63\times10^{-9}$M per cm$^3$ with a pooled relative standard deviation of 5% related to that at the mean concentration. Because this sensor is only $3.11\times10^{-7}$ cm$^3$, hence, its DOL is $8.2\times10^{-16}$M Aβ. FIG. 32B$_1$ illustrates the experimental data points of volumetric energy density vs. Aβ concentration from zero to 471 nM in NIST serum (Red) without a stabilizer TCD, and in water with 0.1 mg/mL stabilizer TCD (black), respectively. The Aβ calibration curve using NIST's reference human serum is shown in FIG. 32B$_2$ in red. The experimental DSCPO curve's control profile is shown in FIG. 32C$_1$ in NIST SRM965A serum samples for without spiking Aβ at ±10 nA at 0.25 Hz. FIG. 32C$_2$ depicts synapse voltage profiles covering clinically useful range between 3.8 to 471 nM Aβ. The linear regression equation of Y=7.51−0.014X, r=−0.995, Sy/x=0.36, N=4, p<0.005. The DOL value is $7.0\times10^{-13}$M/cm$^3$.

Sample 8—Media Affects on the Sensitivity of Detection of Aβ

The difference between −0.018±7.5×10$^{-4}$ and −0.014±0.001 μWHr/cm$^3$/nM is statistically negligible in comparing of the device sensitivity to Aβ in water and in human serum based on a two-tailed Student t test at t$_{0.025}$. It is simply states that there is no protein interference on the sensitivity to detect Aβ in different media using this device, wherein the proportional systematic error is statistically negligible.

Our results demonstrated Aβ is a strong inhibitor agent in blocking memory consolidating at Slow-Wave-Sleeping (SWS) at 0.25 Hz with the initial energy intensity decrease by 94% in 3.8 nM Aβ in serum. It was observed in the insert of FIG. 32B that the synapse energy density signal at Aβ=0 is 8.5-fold higher in the serum than in the aqueous solution at 0.25 Hz indicating the serum is more suitable to the neuronal memcapacitor sensor without instability observed. The synapse energy DSCPO profiles in the presence of Aβ using NIST serum samples were depicted in FIG. 32C. The insert shows the curve without Aβ.

Sample 9—Factors Affect Sensors' Performance

Peak duration time and Aβ concentrations were factors that affect on sensor's performance using the CA method. A healthy subject's fresh finger stick capillary whole blood (CPWB) specimens were collected, then immediately spiked Aβ in various concentrations in less than 4% water content to the blood volume without anticoagulant and without stabilizer. All measurements were in triplicates against controls at room temperature and finished in a half hour. Peak duration time had three levels: 4 ms, 25 ms and 4s. The same factors were used for the voltage sensor under conditions of ±10 nA and 0.25 Hz with data rate 1 kHz, 40, 250 Hz (both had data rate 50 kHz) for action potential peak or resting potential peak, respectively. The subject has gone through consent and was approved with the IRB.

FIG. 33 revealed the high energy density values were associated with specific capacitance values between 1.2-2.2 F/cm$^3$ around zero Aβ compared with the negligible energy density at high Aβ level based on the calculations on the literature [41-42] using n=27 fresh human CPWB specimens with the voltage method. FIG. 34 depicts a map revealed the results obtained by another CA method using the same fresh human CPWB specimens with the larger current density correlated with the highest Aβ concentration that located in the higher frequency at 250 Hz.

Sample 10—Assessing Precision and Accuracy

Precision was evaluated by the two methods using fresh human CPWB specimens with triplicates at two levels of Aβ at 2.3 and 92 nM and three levels of frequencies at 0.25, 40 and 250 Hz in triplicates. Accuracy results were assessed by the "Point Accuracy" using signal means of the CPWB specimens against the calibration curves with the reference results that are traceable to NIST reference serum with the standard addition of the Aβ concentrations.

The imprecision was measured by the CPWB samples for the two sensors with the Pooled RSD of 3.2% (n=18) vs. 6.0% (n=15) over the studied ranges for the CA and the DSCPO method, respectively. The inaccuracy error was 0.1% with a recovery of 100.15±1.2% for CA method after corrected metrics ratio. The average inaccuracy error obtained from the DSCPO method are 0.01% and 1.4% in water and in serum, respectively, that were traceable to the NIST's reference with 99.99±0.01% and 98.6±1.1% recovery.

Sample 11—Signal to Noise Ratio

The ratio of Signal to Noise (S/N) values accessed by the CA method and the DSCPO methods, respectively, were calculated based on the conventional teaching [43]. The results have S/N values of 11.63 vs. 12.5 for the CA and DSCPO method, respectively.

CONCLUSION

An organic nanobiomimetic memristor/memcapacitor dual sensing apparatus comprising arrays of memcapacitors forming 3D cross-bar blocks of a biomimetic neuronal network membrane, plus this invention utilized TCD as a stabilizer for stabilizing Aβ from aggradations and promoted Aβ bio-communication with the neuronal network apparatus, hence make direct detect sub pM Aβ with near 100% recoveries and 3-6% imprecision under antibody-free and tracer-free conditions was demonstrated. The technology may find wide applications for early monitoring of Alzheimer's disease.

REFERENCES

[1]. Reitz C, Brayne C and Mayeux R, *Epidemiology of Alzheimer disease*, Nature Reviews Neurology 7, 137-152, 2011.

[2]. John E. Morleya J E and Farr S A, Biochemical Pharmacology, 88(4), 479-485, 2014.

[3]. Jia Q, Deng Y, and Qing H, BioMed Research International Article ID 837157, 22 pages, 2014.

[4]. Toledo J B, Shaw L M and Trojanowski J Q, Alzheimer's Research & Therapy 5, 8, 2013.

[5]. Lachno D R, Emerson J K, Vanderstichele H, et al, J Alzheimers Dis 32, 905-918, 2012.

[6]. Bibl M, Welge V, Esselmann H, Wiltfang J, Electrophoresis 33, 445-450, 2012.

[7]. Esparza T J, Zhao H, Cirrito J R, Cairns N J et al., Ann Neurol, 73(1), 104-119, 2013.

[8]. Fiandaca M S, Mapstone M E, Cheema A K, Federoff H J, Alzheimer's & Dementia, 10, S196-S212, 2014.

[9]. Zlokovic B V, Neuron, 57(2), 178-201, 2008.

[10]. Chen E T, Duh S H, Ngatchou C, Thornton J T, and Kissinger P T, Nanotech (3), 101-104, 2011.

[11]. Chen E T. U.S. Pat. No. 6,582,583, Jun. 24, 2003.

[12]. Chen E T, U.S. Pat. No. 8,083,926, Dec. 27, 2011.

[13]. Chen E T, Thornton J T, Ngatchou C, Duh S H and Kissinger P T, NSTi-Nanotech (3), 115-118, 2013.

[14]. Chen E T, Thornton J T, Ngatchou C, Duh S H and Kissinger P T, NSTI—Nanotech (2), 107-110, 2013.

[15]. Chen E T, Thornton J, Ngatchou C and Duh S-H., NSTi-*Nanotech*, 2, 169-172, 2014.

[16]. Chen E T, Thornton J and Mulchi Jr C. Sensors & Transducers, 183(12), 72-83, 2014.

[17]. Nordberg A, Rinne J O, Kadir A and Långström B, Nature Reviews, 6, 78-87, 2010,

[18]. Yan J J, Cho A-Y, Kim H-S, Kim K-L, Jung J-S, British J of Pharmacology 133(1). 89-96, 2001

[19]. Chen E T and Pardue H L, *Anal Chem,* 5, 2563-7, 1993.

[20]. Chen E T, Thornton J T, Ngatchou C, Duh S H and Kissinger P T, NSTi—NanoTech (2), 107-110, 2013.

[21]. Chen E T, Thornton J T, Ngatchou C, Duh S H, NSTi-Nanotech, 2, 200-203, 2014.

[22]. Szejtli, *Cyclodextrin and Their Industrial Uses*, Editions Sant'e, Paris, 1987.

[23]. Sussman J L, Harel M, Frolow F, Oefner C, Goldman A, Toker L, Silman I, *Atomic structure of acetylcholinesterase from Torpedo californica: a prototypic acetylcholine-binding protein. Science* 253, 872-879, 1991;

[24]. Gilson M K, Straatsma T P, McCammon J A, Ripon D R, Faerman C H, Silman I, Sussman J L, *Open "back door" in a molecular dynamics simulation of acetylcholinesterase*, Science 263, 1276-1278, 1994.

[25]. Silman I, Sussmana J L, *Acetylcholinesterase: How is structure related to function?* Chem Biol Interact. 175, 3-10, 2008.

[26]. Mira A, Yamashita S, Katakura Y, and Shimizu K. *In vitro neuroprotective activities of compounds from angelica shikokiana makino*, Molecules 20, 4813-4832, 2015.

[27] Biolek D, Di Ventra M, Pershin Y V, *Reliable SPICE Simulations of Memristors, Memcapacitors and Meminductors*, Radioengineering 22 (4), 945-968, 2013.

[28] Martinez-Rincon J and Pershin Y V, *Electron Devices, IEEE Transactions* 58 (6), 1809-1812, 2011.

[29] Martinez-Rincon J, Ventra M D, Pershin Y V, *Solid-State Memcapacitive System with Negative and Diverging Capacitance Physical Review B,* 81(19), 195430-1-195430-7, 2010.

[30] Pickett M D, Medeiros-Ribeiro G and Williams R S, A Nature Materials, DOI: 10.1038/NMAT3510, 2012.

[31] Kozma R, Pino R E, Pazienza G E, *Advances in neuomorphic memristor science and applications*, Springer publisher, 2012.

[32] Ventra M D, Pershin Y V, Nanotechnology 24, 255201, 2013.

[33] Ventra M D and Pershin Y V, *On the physical properties of memristive and memcapacitive and meminductive systems*, J of Physics D, arXiv:1302.7063v2, 2013.

[34] Chen E T, Nanopore Array Structured Devices for Biosensing and Energy Storage, U.S. Pat. No. 8,641,876, Feb. 4, 2014.

[35] Chen E T, Nanopore Structured Electrochemical Biosensor, U.S. Pat. No. 8,083,926, Dec. 27, 2011.

[36] Chen E T, Apparatus and Methods for Making High Performance Fuel Cell, U.S. Pat. No. 8,632,925 issued by USPTO, Jan. 21, 2014.

[37] Chen E T, *Nanostructured Biomimetic Device with Contour Map of Multiple Variable Correlation Method to Visually Display the Cancer Progresses*, U S 20,140,178,925, Jun. 26, 2014.

[38] Chen E T, *Nanobiomimetic Supercapacitors with High Rate High Energy Storage*, U S 20,140,104,751, Apr. 17, 2014.

[39]. Buzsáki G et al., Nature Reviews 13, 407-420, 2012.

[40] Chen E T, *Nanobiomimetic sensing and energy storage* in the first volume of the book series of *Dekker Encyclopedia of Nanoscience and Nanotechnology* edited by Lyshevski S E, CRC *Press*, 2013.

[41] Hu L, Choi J W, Yang Y, Jeong S, Mantia F L, Cui L-F and Cui Y, PNAS 106 (51), 21490-21494, 2009.

[42]. Thornton J, Christelle C and Chen E T, NSTi-Nanotech (2), 672-675, 2013.

[43]. Skoog D A and Leary J J, *Principles of Instrumental Analysis*, Fourth Edition, Saunders College Publishing, 1992.

What is claimed is:

1. An organic nanobiomimetic memristor/memcapacitor dual sensing apparatus comprising arrays of memcapacitors forming 3D cross-bar blocks of a biomimetic neuronal network membrane through self-assembly affixed onto an electrode; the membrane comprises active sites of a biomimetic normal cylindrical confined acetylcholinesterase (ACHE) gorge as an "artificial brain" prosthesis with a "biomimetic linen" lining an inner ACHE gorge, and mimicking neuronal axons.

2. An organic nanobiomimetic memristor/memcapacitor dual sensing apparatus according to claim 1, wherein the inner core biomimetic neuronal axons comprising cyclodextrin (CDs) in chunked "donuts" shape by forming a toroidal matrix.

3. An organic nanobiomimetic memristor/memcapacitor dual sensing apparatus according to claim 2, wherein an array toroial matrix comprises a dipole electron-relay circuit and a flat nanostructure bridge.

4. An organic nanobiomimetic memristor/memcapacitor dual sensing apparatus according to claim 3, wherein the arrayed toroidal matrix membrane thickness with the flat bridges thickness 35.5 nm and the perpendicular bars comprising nanopores in height of 50-60 nm.

5. An organic nanobiomimetic memristor/memcapacitor dual sensing apparatus according to claim 1, wherein a nanometer air gap serves as the dielectric substance located between two bipolar electron-relay circuits.

6. An organic nanobiomimetic memristor/memcapacitor dual sensing apparatus according to claim 5, wherein the nanometer air gaps are adjustable by adjusting the concentration of o-nitrophenyl acetate (NPA) forming vertical larger nano air gaps between linen and the polymer triacetyl-β-cyclodextrin (TCD) . . . . mono imidazol derivative dimethyl β-cyclodextrin (mM-β-DMCD, in short, MCD) . . . . glycol diglycidyl ether (PEG) . . . . poly (4-vinylpyridine) (PVP) against smaller air gaps between CD cavities.

7. An organic nanobiomimetic memristor/memcapacitor dual sensing apparatus according to claim 1, wherein the array cross bars comprise o-nitrophenyl acetate (NPA) formed hydrogen bounding or hydrophobic interaction with triacetyl-β-cyclodextrin (TCD) . . . . glycol diglycidyl ether (PEG)/TCD . . . . poly (4-vinylpyridine) (PVP) wrapped around a flat bridge structure.

8. An organic nanobiomimetic memristor/memcapacitor dual sensing apparatus according to claim 7, wherein the flat bridges densely covered with uniformly and orderly orientated "fish scales" having a density of $10^7$ scales /cm$^2$, with the average donuts size of 22 nm in diameter and the pores in the center are 9-10 nm in diameter.

9. The use of an organic nanobiomimetic memristor/memcapacitor dual sensing apparatus further including the use for direct measuring protein bio-communication in voltage change comprising:
   a) obtaining a sample immersed in a medium which can be detected;
   b) contacting the sample with a device, and the device comprises arrays of memcapacitors forming 3D cross-bar blocks of a biomimetic neuronal network membrane affixed onto said an electrode;
   c) setting up a fixed current and apply the current between a cathode and an anode electrode;
   d) setting up a pulse stepping time in order to measure voltage;
   e) measuring the voltage outcome in the media.

10. An organic nanobiomimetic memristor/memcapacitor dual sensing apparatus according to claim 1, wherein protein β-amyloid (Aβ) is a biomarker for neurodegenerative disease Alzhermer.

11. An organic nanobiomimetic memristor/memcapacitor dual sensing apparatus according to claim 1, wherein a biological media in human blood specimens has negligible interference on the device performance in detecting Aβ.

12. An organic nanobiomimetic memristor/memcapacitor dual sensing apparatus according to claim 1, wherein TCD is a stabilizer for stabilizing Aβ in aqueous solution.

13. An organic nanobiomimetic memristor/memcapacitor dual sensing apparatus according to claim 1, wherein the device is for current and voltage sensing.

14. An organic nanobiomimetic memristor/memcapacitor dual sensing apparatus according to claim 1, wherein the performance by a chronoamperometric (CA) method has a value of Detection of Limit (DOL) of $1.6 \times 10^{12}$ M Aβ in aqueous solutions over the range of 0.037 to 151 nM Aβ.

15. An organic nanobiomimetic memristor/memcapacitor dual sensing apparatus according to claim 1, wherein the performance by a Double Step chronopotentiometry (DSCPO) method has a DOL value of $8.2 \times 10^{16}$M in aqueous solutions over clinically useful range between 3.8 to 471nM Aβ.

16. An organic nanobiomimetic memristor/memcapacitor dual sensing apparatus according to claim 1, wherein fresh human capillary whole blood (CPWB) specimens used to verify the accuracy traceable to NIST standards produced recoveries of 100.15±1.2% and 98.6±1.1% for CA and DSCPO method, respectively.

17. An organic nanobiomimetic memristor/memcapacitor dual sensing apparatus according to claim 1, wherein the imprecision errors are 3.2% vs. 6.0% (n=18, n=15) over the studied Aβ concentrations in CPWB for the CA and DSCPO method, respectively.

18. An organic nanobiomimetic memristor/memcapacitor dual sensing apparatus according to claim 1, wherein signal to noise ratio results for the CA and DSCPO method are similar, 11.63 vs. 12.5 for the CA and DSCPO method, respectively.

19. An organic nanobiomimetic memristor/memcapacitor dual sensing apparatus according to claim 1, wherein the dual functioning sensors' sensitivity to detect Aβ caused either by current increase or by energy decrease are 0.63 82 A/cm$^2$/nM vs. −0.018±0.001 μWHr/cm$^3$/nM, respectively in aqueous solutions.

20. An organic nanobiomimetic memristor/memcapacitor dual sensing apparatus according to claim 1, wherein TCD is a molecular chaperone helping Aβ protein bio-communicating with neuronal network apparatus, wherein avoiding aggradations.

21. An organic nanobiomimetic memristor/memcapacitor dual sensing apparatus according to claim 1, wherein TCD has benefit for helping protein normal folding.

22. The use of an organic nanobiomimetic memristor/memcapacitor dual sensing apparatus further including the use for direct measuring protein bio-communication in electric current change comprising:
 a) obtaining a sample immersed in a medium which can be detected;
 b) contacting the sample with a device, and the device comprises arrays of memcapacitors forming 3D crossbar blocks of a biomimetic neuronal network membrane affixed onto said an electrode;
 c) setting up an appropriate fixed DC electric potential pulse and apply the potential pulse onto the device;
 d) setting up an appropriate pulse stepping time in order to measure the current;
 e) measuring the current outcome in the media.

* * * * *